US012747219B2

(12) United States Patent
Johnson et al.

(10) Patent No.: US 12,747,219 B2
(45) Date of Patent: Sep. 29, 2026

(54) COMPOUNDS AND METHODS OF INHIBITING BACTERIAL CHAPERONIN SYSTEMS

(71) Applicants: THE TRUSTEES OF INDIANA UNIVERSITY, Bloomington, IN (US); ARIZONA BOARD OF REGENTS ON BEHALF OF THE UNIVERSITY OF ARIZONA, Tucson, AZ (US)

(72) Inventors: Steven Johnson, Indianapolis, IN (US); Eli Chapman, Tucson, AZ (US)

(73) Assignees: THE TRUSTEES OF INDIANA UNIVERSITY, Bloomington, IN (US); ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 598 days.

(21) Appl. No.: 18/251,452

(22) PCT Filed: Oct. 26, 2021

(86) PCT No.: PCT/US2021/056565

§ 371 (c)(1),
(2) Date: May 2, 2023

(87) PCT Pub. No.: WO2022/103572

PCT Pub. Date: May 19, 2022

(65) Prior Publication Data

US 2023/0406831 A1 Dec. 21, 2023

Related U.S. Application Data

(60) Provisional application No. 63/113,297, filed on Nov. 13, 2020.

(51) Int. Cl.

| | |
|---|---|
| ***C07D 277/74*** | (2006.01) |
| ***A01P 1/00*** | (2006.01) |
| ***A61P 31/04*** | (2006.01) |
| ***C07C 235/64*** | (2006.01) |
| ***C07C 255/44*** | (2006.01) |

(52) U.S. Cl.

CPC .............. *C07D 277/74* (2013.01); *A01P 1/00* (2021.08); *A61P 31/04* (2018.01); *C07C 235/64* (2013.01); *C07C 255/44* (2013.01)

(58) Field of Classification Search

CPC .... C07D 277/74; C07C 235/64; C07C 255/44
See application file for complete search history.

(56) References Cited

U.S. PATENT DOCUMENTS

2018/0207179 A1 7/2018 Sommer
2018/0360799 A1 12/2018 Wang
2022/0009914 A1 1/2022 Johnson
2025/0319056 A1 10/2025 Johnson

FOREIGN PATENT DOCUMENTS

WO 2006132583 12/2006
WO 2018013890 1/2018
WO 2020/092947 A1 5/2020
WO 2024081714 4/2024

OTHER PUBLICATIONS

Klee, et al. U.S. Pat. No. 8,709,811 (abstract); Apr. 29, 2014, retrieved from STN; Accession No. 2016:1866534.*
PCT International Search Report and Written Opinion completed by the ISA/US on Feb. 2, 2022 and issued in connection with PCT/US2021/056565.
Pubchem, Substance Record for SID 385643875, Available Date: Sep. 23, 2019 [retrieved on Nov. 30, 2021). Retrieved from the Internet: <URL: https://pubchem.ncbi.nlm.nih.gov/substance/385643875> entire document.
Kunkle, Antibiotic Discovery Targeting Bacterial GROEUGROES Chaperonin Systems, Department of Biochemistry and Molecular Biology Indiana University, Master's Thesis, Aug. 2018 [retrieved Feb. 1, 2022). Retrieved from the internet: <URL: https ://scholarworks.iupui .edu/bitstream/handle/1805/17 427 /Thesis%20for%20MS%20Trent%20A%20Kunkle.pdf?isAllowed=y&sequence=3> entire document.
Extended EP Search Report completed by the ISA/EP on Sep. 30, 2024 and issued in connection with EP Application No. 21892560.0.
Kunkle, Trent, et al., "Hydroxybiphenylamide GroEL/ES Inhibitors Are Potent Antibacterials against Planktonic and Biofilm Forms of *Staphylococcus aureus*", Journal of Medicinal Chemistry, vol. 61, No. 23, Nov. 4, 2018 (Nov. 4, 2018), pp. 10651-10664.
Palace-Berl, F. et al., "Investigating the structure-activity relationships of N'-[(5-nitrofuran-2-yl) methylene] substituted hydrazides against Trypanosoma cruzi to design novel active compounds," European Journal of Medicinal Chemistry, 2018, pp. 29-40, 144.
Park, H. K., Lee, J. E., Lim, J., Jo, D. E., Park, S. A., Suh, P. G., and Kang, B. H. (2014) Combination treatment with doxorubicin and gamitrinib synergistically augments anticancer activity through enhanced activation of Bim. BMC Cancer 14, 431.
PCT International Search Report and Written Opinion completed by the ISA/US on Feb. 3, 2020 and issued in connection with PCT/US2019/059458.
PCT International Search Report and Written Opinion completed by the ISA/US on Mar. 7, 2024 and issued in connection with PCT/US2023/076571.
Pence, M. A., Haste, N. M., Meharena, H. S., Olson, J., Gallo, R. L., Nizet, V., and Kristian, S. A. (2015) Beta-Lactamase Repressor Blal Modulates *Staphylococcus aureus* Cathelicidin Antimicrobial Peptide Resistance and Virulence. PLoS One 10, e0136605.
Piper, P. W., and Millson, S. H. (2012) Spotlight on the microbes that produce heat shock protein 90-targeting antibiotics. Open Biol 2, 120138.
PubChem-SID-107783417, Modify Date: May 31, 2019 (May 31, 2019), p. 2, figure.
PubChem-SID-108392949, Modify Date: May 31, 2019 (May 31, 2019), p. 2, figure.

(Continued)

*Primary Examiner* — Shawquia Jackson
(74) *Attorney, Agent, or Firm* — Barnes & Thornburg LLP

(57) ABSTRACT

The present disclosure relates to compounds and methods of killing or inhibiting the growth of bacteria by disrupting chaperonin-mediated refolding of proteins.

20 Claims, No Drawings

(56) References Cited

OTHER PUBLICATIONS

Pubchem, Substance Record for SID 341146615. Available Date: Sep. 13, 2017. [retrieved on Dec. 4, 2019]. Retrieved from the Internet: <https://pubchem.ncbi.nlm.nih.gov/substance/341146615>. entire document.
Salton, M. R. J., and Kim, K. S. (1996) Structure. in Medical Microbiology (Baron, S. ed.), 4th Ed., Galveston (TX).
Singh, R., Ray, P., Das, A., and Sharma, M. (2010) Penetration of antibiotics through *Staphylococcus aureus* and *Staphylococcus epidermidis* biofilms. J Antimicrob Chemother 65, 1955-1958.
Stefani, M., and Dobson, C. M. (2003) Protein aggregation and aggregate toxicity: new insights into protein folding, misfolding diseases and biological evolution. J Mol Med (Berl) 81, 678-699.
Stewart, P. S., and Costerton, J. W. (2001) Antibiotic resistance of bacteria in biofilms. Lancet 358, 135-138.
Stromberg, B. E., Schlotthauer, J. C., and Conboy, G. A. (1984) The efficacy of closantel against Fascioloides magna in sheep. J Parasitol 70, 446-447.
Talon, D. (1999) The role of the hospital environment in the epidemiology of multi-resistant bacteria. J Hosp Infect 43, 13-17.
Wang et al., Design, synthesis and antibacterial activities of vanillic acylhydrazone derivatives as potential B-ketoacyl-acyl carrier protein synthase III (FabH) inhibitors. European Journal of Medicinal Chemistry, 2012, 57, 373-382.
Wang, Q., Buckle, A. M., and Fersht, A. R. (2000) From minichaperone to GroEL 1: information on GroEL-polypeptide interactions from crystal packing of minichaperones. J Mol Biol 304, 873-881.
Whitesell, L., and Lindquist, S. L. (2005) HSP90 and the chaperoning of cancer. Nat Rev Cancer 5, 761-772.
Wright, G. D., and Sutherland, A. D. (2007) New strategies for combating multidrug-resistant bacteria. Trends Mol Med 13, 260-267.
Yarlagadda, V., Manjunath, G. B., Sarkar, P., Akkapeddi, P., Paramanandham, K., Shome, B. R., Ravikumar, R., and Haldar, J. (2016) Glycopeptide Antibiotic To Overcome the Intrinsic Resistance of Gram-Negative Bacteria. ACS Infect Dis 2, 132-139.
Abdeen, S. et al., "GroEL/GroES inhibitors as potential antibiotics," Bioorganic & Medicinal Chemistry Letters, 2016, pp. 3127-3134, 26(13).
Alsaeedi, H. S. et al. Synthesis and Investigation of Antimicrobial Activity of Some Nifuroxazide Analogues. Asian Journal of Chemistry, 2015, 27, pp. 3639-3646.
Armstrong, G. L., Conn, L. A., and Pinner, R. W. (1999) Trends in infectious disease mortality in the United States during the 20th century. Jama-J Am Med Assoc 281, 61-66.
Baig, U. I., Bhadbhade, B. J., Mariyam, D., and Watve, M. G. (2014) Protein aggregation in *E. coli* : short term and long term effects of nutrient density. PLoS One 9, e107445.
Bao, Y. P., Cook, L. J., O'Donovan, D., Uyama, E., and Rubinsztein, D. C. (2002) Mammalian, yeast, bacterial, and chemical chaperones reduce aggregate formation and death in a cell model of oculopharyngeal muscular dystrophy. J Biol Chem 277, 12263-12269.
Bjarnsholt, T. (2013) The role of bacterial biofilms in chronic infections. APMIS Suppl, 1-51.
Boucher, H. W., Talbot, G. H., Bradley, J. S., Edwards, J. E., Gilbert, D., Rice, L. B., Scheld, M., Spellberg, B., and Bartlett, J. (2009) Bad bugs, no drugs: no ESKAPE! An update from the Infectious Diseases Society of America. Clin Infect Dis 48, 1-12.
Brotz-Oesterhelt, H., Beyer, D., Kroll, H. P., Endermann, R., Ladel, C., Schroeder, W., Hinzen, B., Raddatz, S., Paulsen, H., Henninger, K., Bandow, J. E., Sahl, H. G., and Labischinski, H. (2005) Dysregulation of bacterial proteolytic machinery by a new class of antibiotics. Nat Med 11, 1082-1087.
Brown, A. G., Butterworth, D., Cole, M., Hanscomb, G., Hood, J. D., Reading, C., and Rolinson, G. N. (1976) Naturally-occurring beta-lactamase inhibitors with antibacterial activity. J Antibiot (Tokyo) 29, 668-669.
CAPLUS printout of "Shi et al., Green synthesis and antitumor activities of 18-hydroxyquinoline-7-carbaldehyde aroylhydrazone Schiff bases. Huaxue Tongbao, 2013, 76, p. 72-76.".
Carmichael, J., Chatellier, J., Woolfson, A., Milstein, C., Fersht, A. R., and Rubinsztein, D. C. (2000) Bacterial and yeast chaperones reduce both aggregate formation and cell death in mammalian cell models of Huntington's disease. Proc Natl Acad Sci U S A 97, 9701-9705.
CDC. (2013) Antibiotic Resistance Threats in the United States Centers for Disease Control and Prevention.
Chapman, E., Farr, G. W., Usaite, R., Furtak, K., Fenton, W. A., Chaudhuri, T. K., Hondorp, E. R., Matthews, R. G., Wolf, S. G., Yates, J. R., Pypaert, M., and Horwich, A. L. (2006) Global aggregation of newly translated proteins in an *Escherichia coli* strain deficient of the chaperonin GroEL. Proc Natl Acad Sci U S A 103, 15800-15805.
Chemical Abstract Registry No. 300732-09-6, indexed in the Registry File on STN CAS Online Nov. 1, 2000.
Chemical Abstract Registry No. 340203-83-0, indexed in the Registry File on STN CAS Online Jun. 10, 2001.
Chemical Abstract Registry No. 351983-85-2, indexed in the Registry File on STN CAS Online Aug. 20, 2001.
Chemical Abstract Registry No. 414897-53-3, indexed in the Registry File on STN CAS Online May 13, 2002.
Chemical Abstract Registry No. 870981-92-3, indexed in the Registry File on STN CAS Online Jan. 3, 2006.
Chemical Abstract Registry No. 904050-35-7, indexed in the Registry File on STN CAS Online Aug. 24, 2006.
Cheng, M. Y., Hartl, F. U., Martin, J., Pollock, R. A., Kalousek, F., Neupert, W., Hallberg, E. M., Hallberg, R. L., and Horwich, A. L. (1989) Mitochondrial heat-shock protein hsp60 is essential for assembly of proteins imported into yeast mitochondria. Nature 337, 620-625.
Chiappori, F., Fumian, M., Milanesi, L., and Merelli, I. (2015) DnaK as Antibiotic Target: Hot Spot Residues Analysis for Differential Inhibition of the Bacterial Protein in Comparison with the Human HSP70. PLoS One 10, e0124563.
Dalbey, R. E., Wang, P., and van Dijl, J. M. (2012) Membrane proteases in the bacterial protein secretion and quality control pathway. Microbiol Mol Biol Rev 76, 311-330.
Davies, J., and Davies, D. (2010) Origins and evolution of antibiotic resistance. Microbiol Mol Biol Rev 74, 417-433.
De Groot, N. S., and Ventura, S. (2010) Protein aggregation profile of the bacterial cytosol. PLoS One 5, e9383.
Eaves, D. J., Randall, L., Gray, D. T., Buckley, A., Woodward, M. J., White, A. P., and Piddock, L. J. (2004) Prevalence of mutations within the quinolone resistance-determining region of gyrA, gyrB, parC, and parE and association with antibiotic resistance in quinolone-resistant *Salmonella enterica*. Antimicrob Agents Chemother 48, 4012-4015.
Enright, M. C. (2003) The evolution of a resistant pathogen—the case of MRSA. Curr Opin Pharmacol 3, 474-479.
Fujikawa, Fukujiro et al., "Studies on chemotherapeutics for *Mycobacterium tuberculosis*. XVIII. Synthesis and antibacterial activity on Mycobacterium tuberculosis of Formyl-8-hydroxyquinoline derivatives," Yakugaku Zasshi : Journal of the Pharmaceutical Society of Japan, Jul. 1, 1967, pp. 844-849, 87(7), DOI: 10.1248/yakushi1947.87.7_844.
Giedraitiene, A., Vitkauskiene, A., Naginiene, R., and Pavilonis, A. (2011) Antibiotic resistance mechanisms of clinically important bacteria. Medicina (Kaunas) 47, 137-146.
Gonzalez-Zorn, B., and Courvalin, P. (2003) VanA-mediated high level glycopeptide resistance in MRSA. Lancet Infect Dis 3, 67-68.
Hancock, R. E. (2005) Mechanisms of action of newer antibiotics for Gram-positive pathogens. Lancet Infect Dis 5, 209-218.
Hartl, F. U., Bracher, A., and Hayer-Hartl, M. (2011) Molecular chaperones in protein folding and proteostasis. Nature 475, 324-332.
Hiramatsu, K., Hanaki, H., Ino, T., Yabuta, K., Oguri, T., and Tenover, F. C. (1997) Methicillin-resistant *Staphylococcus aureus* clinical strain with reduced vancomycin susceptibility. J Antimicrob Chemother 40, 135-136.

(56) References Cited

OTHER PUBLICATIONS

Horwich, A. L., Fenton, W. A., Chapman, E., and Farr, G. W. (2007) Two families of chaperonin: physiology and mechanism. Annu Rev Cell Dev Biol 23, 115-145.
Intelligence, B. H. (2017) The Health of America Report: Antibiotic Prescription Fill Rates Declining in the U.S., 27.
Jacob, A. E., and Hobbs, S. J. (1974) Conjugal transfer of plasmid-borne multiple antibiotic resistance in *Streptococcus faecalis* var. zymogenes. J Bacteriol 117, 360-372.
Johnson, S. et al., "A biochemical screen for GroEL/GroES inhibitors," Bioorganic & Medicinal Chemistry Letters, 2014, pp. 786-789, 24(3).
Johnson, S., et al. "A biochemical screen for GroEL/GroES inhibitors" Bioorg Med Chem Lett (2014) 24, 786-789.
Kim, S., Lieberman, T. D., and Kishony, R. (2014) Alternating antibiotic treatments constrain evolutionary paths to multidrug resistance. Proc Natl Acad Sci U S A 111, 14494-14499.
Kroemer, G., and Reed, J. C. (2000) Mitochondrial control of cell death. Nat Med 6, 513-519.
Kumar, C. M., Mande, S. C., and Mahajan, G. (2015) Multiple chaperonins in bacteria—novel functions and non-canonical behaviors. Cell Stress Chaperones 20, 555-574.
Kwasny, S. M., and Opperman, T. J. (2010) Static biofilm cultures of Gram-positive pathogens grown in a microtiter format used for anti-biofilm drug discovery. Curr Protoc Pharmacol Chapter 13, Unit 13A 18.
Lewis, K. (2013) Platforms for antibiotic discovery. Nat Rev Drug Discov 12, 371-387.
Lowy, F. D. (2003) Antimicrobial resistance: the example of *Staphylococcus aureus*. J Clin Invest 111, 1265-1273.
Maisonneuve, E., Ezraty, B., and Dukan, S. (2008) Protein aggregates: an aging factor involved in cell death. J Bacteriol 190, 6070-6075.
Musk, D. J., Jr., and Hergenrother, P. J. (2006) Chemical countermeasures for the control of bacterial biofilms: effective compounds and promising targets. Curr Med Chem 13, 2163-2177.
Nakae, T. (1986) Outer-membrane permeability of bacteria. Crit Rev Microbiol 13, 1-62.
Nathan, C. (2004) Antibiotics at the crossroads Nature 431, 3.
Navarre, W. W., and Schneewind, O. (1999) Surface proteins of gram-positive bacteria and mechanisms of their targeting to the cell wall envelope. Microbiol Mol Biol Rev 63, 174-229.
Nikaido, H. (1996) Multidrug efflux pumps of gram-negative bacteria. J Bacteriol 178, 5853-5859.
Palace-Berl, et al., Designing and exploring active N'-[(5-nitrofuran-2-yl) methylene] substituted hydrazides against three Trypanosoma cruzi strains more prevalent in Chagas disease patients. European Journal of Medicinal Chemistry, 2015, 96, 330-339.

* cited by examiner

COMPOUNDS AND METHODS OF INHIBITING BACTERIAL CHAPERONIN SYSTEMS

CROSS REFERENCE TO RELATED APPLICATIONS

This application is a U.S. national counterpart application of international application serial No. PCT/US2021/056565 filed Oct. 26, 2021, which claims priority to U.S. Provisional Patent Application No. 63/113,297 filed on Nov. 13, 2020, the disclosures of which are hereby expressly incorporated herein by reference in their entireties.

STATEMENT OF US GOVERNMENT SUPPORT

This invention was made with government support under GM120350 awarded by the National Institutes of Health. The government has certain rights in the invention.

BACKGROUND

While disrupting protein homeostasis has proven an effective antibacterial strategy in the context of inhibiting the assembly of ribosomal or transcriptional machinery, perturbing protein folding pathways has gone largely unexplored. To facilitate newly synthesized polypeptides folding to their active/native structural conformations, cells have evolved a class of accessory proteins termed molecular chaperones. Molecular chaperones, also known as Heat Shock Proteins (HSPs), are divided into 5 general classes based on the molecular weights of their subunits: HSP100, HSP90, HSP70, HSP60 chaperonins, and small HSPs. When molecular chaperone functions are compromised, non-native polypeptides misfold and aggregate, which is detrimental to cell viability. Thus, targeting molecular chaperones with small molecule inhibitors may be an effective strategy for killing bacteria that is unique from the mechanisms of current antibiotics.

While research is underway to target HSP70 and HSP90 chaperones as antibiotic strategies, targeting HSP60 chaperonin systems, called GroEL chaperonins in bacteria, has gone largely unexplored. GroEL functions to refold substrate polypeptides through a mechanism unique from other molecular chaperones. GroEL is a homo-tetradecameric protein that consists of two, seven-membered rings that stack back-to-back with each other. To facilitate the folding of substrate polypeptides, GroEL requires binding of ATP and a co-chaperone, called GroES. GroES binding to the GroEL apical domains encapsulates the unfolded polypeptide, where it can attempt to fold within the ring and is sequestered from the outside environment.

It is now apparent that bacteria have intrinsic mechanisms to evade the effects of antibiotics. For instance, many bacteria can surround themselves in a highly impermeable matrix made up of proteins and polysaccharides, known as biofilm. While vancomycin is effective at treating planktonic (free-floating) *Staphylococcus aureus*, it cannot penetrate biofilms; thus, *S. aureus* bacteria are able to hide out within these reservoirs until drugs are systemically cleared. Biofilm formation has been associated with poor prognosis in diseases such as cystic fibrosis, and enhances persistence and spread of infection by adhering to tissues and medical devices. Continued presence of these biofilms has been a hallmark of cases of chronic infection, demonstrating increased resistance to treatments through time as they persist.

While innate mechanisms predispose some bacteria to being naturally resistant to various classes of antibiotics, a striking observation was noted just a few short years after introduction of the early antibiotics: bacterial strains were identified that were resistant to what were previously effective drug dosages. Scientists began to realize that antibiotic-specific resistance was stemming from two primary mechanisms. In the first mechanism, bacteria were accumulating mutations in their own genes to prevent drugs from binding to their targets. An example of this is resistance to quinolone antibiotics, where bacteria accumulate mutations in topoisomerases including GyrA, GyrB, ParA, and ParC (Eaves 2004). This process raises fitness in cultures exhibiting this genotype, thriving where wild-type (WT) strains do not.

In the second mechanism of acquired resistance, it was found that bacteria can acquire new genes from other bacteria through a process called conjugal transfer. For example, strains of *S. aureus* have become resistant to vancomycin by acquiring the vanA operon from *Enterococcus faecalis*. In the acquisition of this operon, *S. aureus* can synthesize peptide intermediates that are not susceptible to vancomycin. These peptide intermediates can then cross-link forming peptidoglycan, thus continuing growth.

To circumvent pre-disposed resistance mechanisms, there is a need for new antibacterials that function through new mechanisms of action and against previously unexploited pathways.

SUMMARY

In some embodiments, the disclosure relates to a compound of the formula I

I

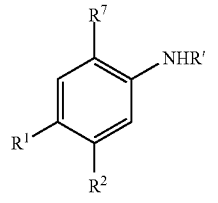

wherein

R' is $C_1$-$C_6$ alkyl or

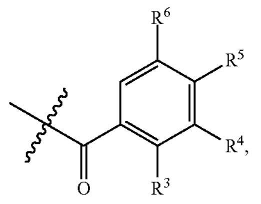

$R^1$ is H, —OH, —$OC_1$—$C_6$ alkyl, —NHC(O)$C_1$-$C_6$ alkyl, —C(O)P$C_1$—$C_6$ alkyl, —C(O)OH, $C_1$-$C_6$ alkyl, —S-heteroaryl, or

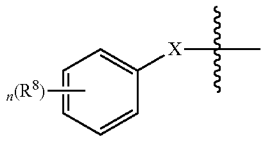

, wherein each hydrogen atom in $C_1$-$C_6$ alkyl is optionally substituted by —CN, $R^2$ is H or halo, each of $R^3$, $R^4$, $R^5$, and $R^6$ is independently H, —OH, halo, —$C_1$-$C_6$ alkyl, —O—$C_1$-$C_6$ alkyl, —$NO_2$, or —$NH_2$, $R^7$ is H or $C_1$-$C_6$ alkyl, X is —O—, —S—, —$C(R^9)(R^9)_m$—, or —$C(R^9)(R^{10})_m$O—, optionally X is —O—, —S—, or —$C(R^9)$(CN);

$R^8$ is halo, $R^9$ is H or —CN, $R^{10}$ is H or —CN, m is 1 or 2, and n is 0, 1, or 2;

or a pharmaceutically acceptable salt thereof, provided the compound of formula (I) is not

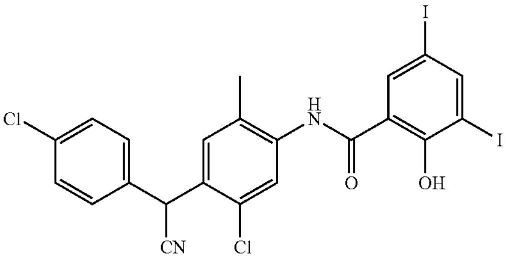

or

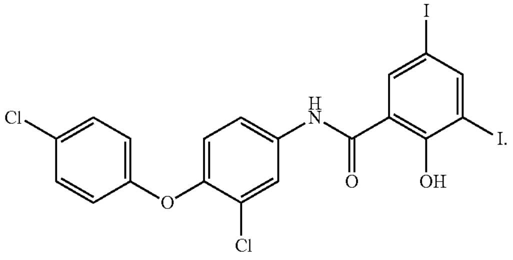

In one embodiment a method of inhibiting chaperonin-mediated refolding is provided wherein GroEL/ES and/or HSP60/10 complexes are contacted with one or more of the compounds disclosed herein, optionally as determined by the assay of Example 76. In one embodiment the compounds have the structure of any one of compounds I, Ia or Ib.

In one embodiment a method of killing or inhibiting the growth of bacteria is provided. In one embodiment the method comprises contacting bacteria with one or more of the compounds disclosed herein, optionally wherein the compounds have activity in inhibiting chaperonin-mediated refolding as measured in the dMDH refolding assay of Example 76. In one embodiment the method of killing or inhibiting the growth of bacteria comprises contacting bacteria with a compound of formula I, Ia or Ib, or a pharmaceutically acceptable salt thereof.

DETAILED DESCRIPTION

Definitions

In describing and claiming the invention, the following terminology will be used in accordance with the definitions set forth below.

The term "about" as used herein means greater or lesser than the value or range of values stated by 10 percent but is not intended to limit any value or range of values to only this broader definition. Each value or range of values preceded by the term "about" is also intended to encompass the embodiment of the stated absolute value or range of values.

As used herein, the term "purified" and like terms relate to the isolation of a molecule or compound in a form that is substantially free of contaminants normally associated with the molecule or compound in a native or natural environment. As used herein, the term "purified" does not require absolute purity; rather, it is intended as a relative definition.

The term "isolated" requires that the referenced material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "treating" includes alleviation of the symptoms associated with a specific disorder or condition and/or preventing or eliminating said symptoms.

As used herein an "effective" amount or a "therapeutically effective amount" of a drug refers to a nontoxic but enough of the drug to provide the desired effect. The amount that is "effective" will vary from subject to subject or even within a subject overtime, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

As used herein the term "patient" without further designation is intended to encompass any warm blooded vertebrate domesticated animal (including for example, but not limited to livestock, horses, cats, dogs and other pets) and humans receiving a therapeutic treatment whether or not under the supervision of a physician.

The term "inhibit" defines a decrease in an activity, response, condition, disease, or other biological parameter. This can include but is not limited to the complete ablation of the activity, response, condition, or disease. This may also include, for example, a 10% reduction in the activity, growth, response, condition, or disease as compared to the native or control level. Thus, the reduction can be a 20, 30, 40, 50, 60, 70, 80, 90, 100%, or any amount of reduction in between as compared to native or control levels.

Embodiments

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Definitions

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, butyl, pentyl, hexyl, iso-propyl, iso-butyl, sec-butyl, tert-butyl, and the like. As used herein, the term "alkylene" refers to a straight or branched, saturated, aliphatic diradical having the number of carbon atoms indicated. For example, $C_1$-$C_6$ alkyl includes, but is not limited to, methylene, ethylene, propylene, butylene, pentylene, hexylene, and the like. It will be appreciated that alkyl and alkylene groups can be optionally substituted with one or more substituents by replacement of one or more hydrogen atoms on the alkyl and alkylene group.

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

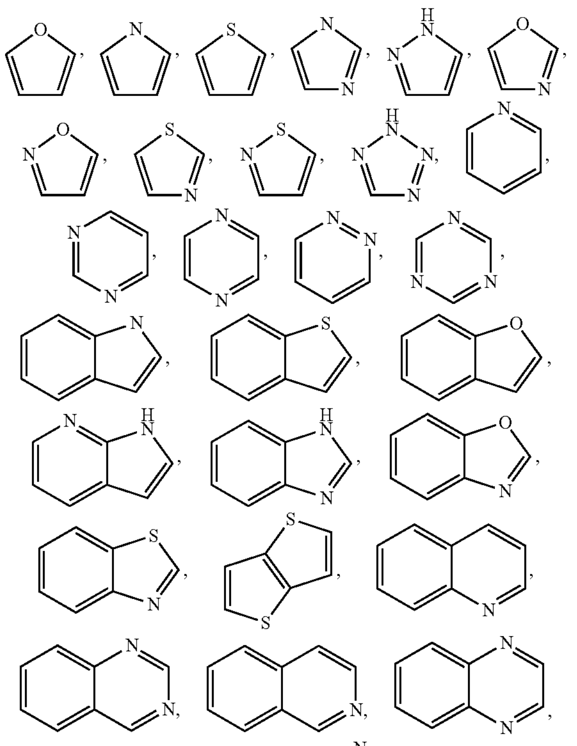

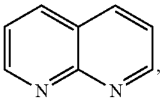, and 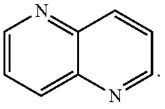.

As used herein, "halogen" or "halo" refers to fluorine, chlorine, bromine, or iodine.

As used herein, "bond" refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. As used herein, "substituted" means that the specified group or moiety bears one, two, or three substituents.

As used herein, "optional" or "optionally" means that the subsequently described event or circumstance may, but need not, occur and that the description includes instances where the event or circumstance occurs and instances in which it does not. For example, "wherein each hydrogen atom in $C_1$-$C_6$ alkyl is independently optionally substituted by —CN" means that a cyano may be, but need not, be present on the $C_1$-$C_6$ alkyl including where each hydrogen atom of the $C_1$-$C_6$ alkyl is substituted with a cyano group, or situations where one or more hydrogens atoms of the $C_1$-$C_6$ alkyl is substituted with a cyano group and situations where the $C_1$-$C_6$ alkyl is not substituted with the cyano group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the term "pharmaceutically acceptable salt" refers to those salts with counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like. Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof. For example, it will be appreciated that compounds depicted by a structural formula containing the symbol "∿∿∿" include both stereoisomers for the carbon atom to which the symbol "∿∿∿" is attached, specifically both the bonds "◀" and "⋯⋯" are encompassed by the meaning of "∿∿∿".

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

Representative Embodiments

In some embodiments, the disclosure relates to a compound of the formula I

I

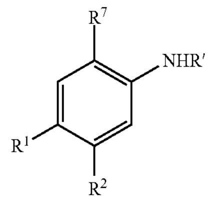

wherein

R' is $C_1$-$C_6$ alkyl or

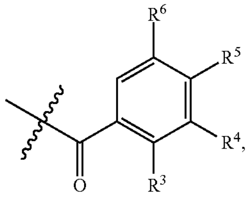

$R^1$ is H, —OH, —$OC_1$—$C_6$ alkyl, —NHC(O)$C_1$-$C_6$ alkyl, —C(O))$C_1$-$C_6$ alkyl, —C(O)OH, $C_1$-$C_6$ alkyl, —S-heteroaryl, or

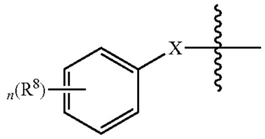

, wherein each hydrogen atom in $C_1$-$C_6$ alkyl is optionally substituted by —CN, $R^2$ is H or halo, each of $R^3$, $R^4$, $R^5$, and $R^6$ is independently H, —OH, halo, —O—$C_1$-$C_6$ alkyl, —$NO_2$, or —$NH_2$, $R^7$ is H or $C_1$-$C_6$ alkyl, X is —O—, —S—, —C($R^9$)($R^{10}$)$_m$—, or —C($R^9$)($R^{10}$)$_m$O—, optionally X is —O—, —S—, or —C($R^9$)(CN);

$R^8$ is halo, $R^9$ is H or —CN, $R^{10}$ is H or —CN, m is 1 or 2, and n is 0, 1, or 2;

or a pharmaceutically acceptable salt thereof, provided the compound of formula (I) is not

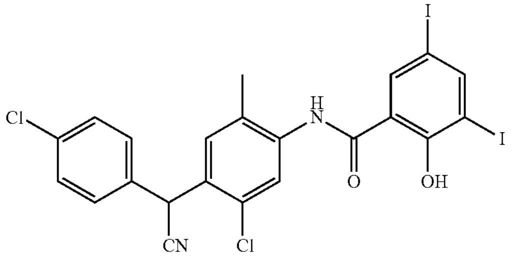

or

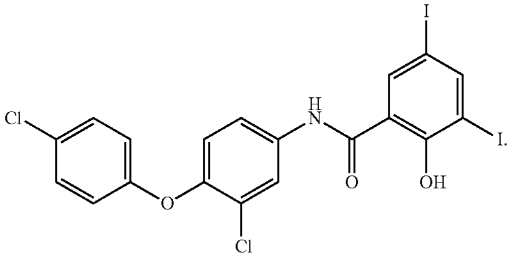

In some embodiments, R' is $C_1$-$C_6$ alkyl or

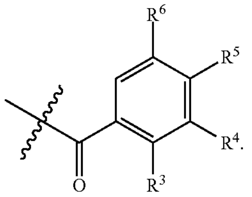

In some embodiments, R' is $C_1$-$C_6$ alkyl. In some embodiments R' is

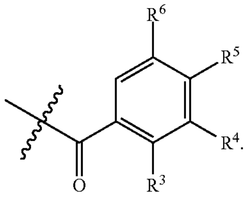

In some embodiments $R^1$ is H, —OH, —$OC_1$—$C_6$ alkyl, —NHC(O)$C_1$-$C_6$ alkyl,

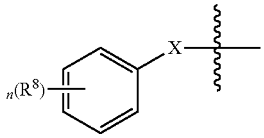

,

—C(O)$OC_1$—$C_6$ alkyl, —C(O)OH, $C_1$-$C_6$ alkyl, —S-heteroaryl, or wherein each hydrogen atom in $C_1$-$C_6$ alkyl is optionally substituted by —CN. In some embodiments, $R^1$ is H. In some embodiments, $R^1$ is —OH. In some embodiments, $R^1$ is —$OC_1$—$C_6$ alkyl. In some embodiments, $R^1$ is —NHC(O)$C_1$-$C_6$ alkyl. In some embodiments, $R^1$ is —C(O)$OC_1$—$C_6$ alkyl. In some embodiments, $R^1$ is —C(O)OH. In some embodiments, $R^1$ is $C_1$-$C_6$ alkyl. In some embodiments, $R^1$ is —S-heteroaryl. In some embodiments, $R^1$ is

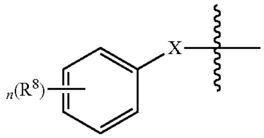

.

In some embodiments, when $R^1$ comprises a $C_1$-$C_6$ alkyl, each hydrogen atom may be optionally substituted by —CN. In some embodiments, $R^1$ is —S-benzothiazole.

In some embodiments, $R^2$ is H or a halo. In some embodiments, $R^2$ is H. In some embodiments, $R^2$ is a halo. In some embodiments, $R^2$ is bromo. In some embodiments, $R^2$ is chloro. In some embodiments, $R^2$ is iodo. In some embodiments, $R^2$ is fluoro.

In some embodiments, each of $R^3$, $R^4$, $R^5$, and $R^6$ is independently H, —OH, halo, $C_1$-$C_6$ alkyl, —O—$C_1$-$C_6$ alkyl, —$NO_2$, or —$NH_2$. In some embodiments, $R^3$ is H. In some embodiments, $R^3$ is —OH. In some embodiments, $R^3$ is a halo. In some embodiments, $R^3$ is selected from the group consisting of fluoro, chloro, bromo, and iodo. In some embodiments, $R^3$ is —O—$C_1$-$C_6$ alkyl. In some embodiments, $R^3$ is —$NO_2$. In some embodiments, $R^3$ is —$NH_2$.

In some embodiments, $R^4$ is H. In some embodiments, $R^4$ is —OH. In some embodiments, $R^4$ is a halo. In some embodiments, $R^4$ is selected from the group consisting of fluoro, chloro, bromo, and iodo In some embodiments, $R^4$ is —O—$C_1$-$C_6$ alkyl. In some embodiments, $R^4$ is —$NO_2$. In some embodiments, $R^4$ is —$NH_2$.

In some embodiments, $R^5$ is H. In some embodiments, $R^5$ is —OH. In some embodiments, $R^5$ is a halo. In some embodiments, $R^5$ is selected from the group consisting of fluoro, chloro, bromo, and iodo. In some embodiments, $R^5$ is —O—$C_1$-$C_6$ alkyl. In some embodiments, $R^5$ is —$NO_2$. In some embodiments, $R^5$ is —$NH_2$.

In some embodiments, $R^6$ is H. In some embodiments, $R^6$ is —OH. In some embodiments, $R^6$ is a halo. In some embodiments, $R^6$ is selected from the group consisting of fluoro, chloro, bromo, and iodo. In some embodiments, $R^6$ is —O—$C_1$-$C_6$ alkyl. In some embodiments, $R^6$ is —$NO_2$. In some embodiments, $R^6$ is —$NH_2$. In some embodiments, $R^6$ is chloro.

In some embodiments, $R^7$ is H or $C_1$-$C_6$ alkyl. In some embodiments, $R^7$ is H. In some embodiments, $R^7$ is $C_1$-$C_6$ alkyl. In some embodiments, $R^7$ is methyl.

In some embodiments, X is —O—, —S—, —$C(R^9)(R^{10})_m$—, or —$C(R^9)(R^{10})_m$O—. In some embodiments, X is —C(H)(CN)—. In some embodiments, X is —O—. In some embodiments, X is —S—. In some embodiments, X is —$C(R^9)(R^{10})_m$—. In some embodiments, X is —$C(R^9)(R^{10})_m$O—. In some embodiments, m is 1 and X is —$C(R^9)(R^{10})$—O—. In some embodiments, m is 1 and X is —$C(R^9)(R^{10})$—. In some embodiments, m is 1 and X is —C(H)(CN)—O—. In some embodiments, m is 1 and X is —C(H)(CN)—.

In some embodiments, $R^8$ is halo. In some embodiments, $R^8$ is bromo. In some embodiments, $R^8$ is chloro. In some embodiments, $R^8$ is fluoro. In some embodiments, $R^8$ is iodo.

In some embodiments, $R^9$ is H or —CN. In some embodiments, $R^9$ is H. In some embodiments, $R^9$ is —CN.

In some embodiments, $R^{10}$ is H or —CN. In some embodiments, $R^{10}$ is H. In some embodiments, $R^{10}$ is —CN.

In some embodiments, m is 1 or 2. In some embodiments, m is 1. In some embodiments, m is 2.

In some embodiments, n is 0, 1, or 2. In some embodiments, n is 0. In some embodiments, n is 1. In some embodiments, n is 2.

In some embodiments, the compound of formula (I) is not

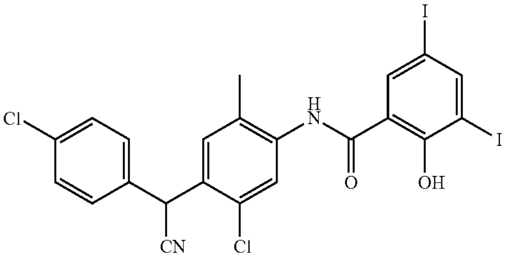

(closantel)

or

-continued

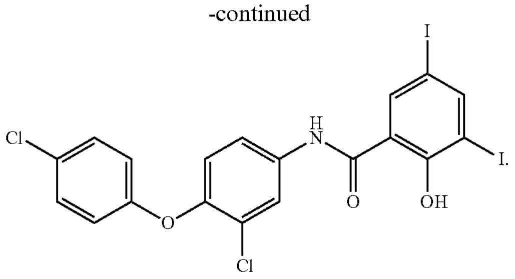

(racoxanide)

In some embodiments, the compound or pharmaceutically acceptable salt of formula I, is formula (Ia)

(Ia)

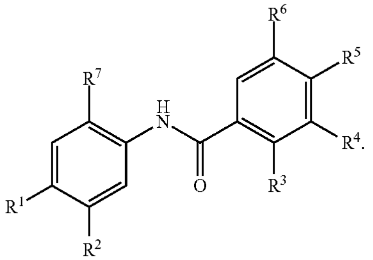

In some embodiments, $R^3$ is —OH or —O—$C_1$-$C_6$ alkyl. In some embodiments, $R^3$ is —OH. In some embodiments $R^3$ is —O—$C_1$-$C_6$ alkyl.

In some embodiments, $R^4$ is halo. In some embodiments, $R^4$ is a bromine. In some embodiments, $R^4$ is a chlorine. In some embodiments, $R^4$ is a fluorine. In some embodiments, $R^4$ is an iodine.

In some embodiments, $R^6$ is halo. In some embodiments, $R^6$ is a bromo. In some embodiments, $R^6$ is a chloro. In some embodiments, $R^6$ is a fluoro. In some embodiments, $R^6$ is an iodo.

In some embodiments, the compound is the formula (Ib)

Ib

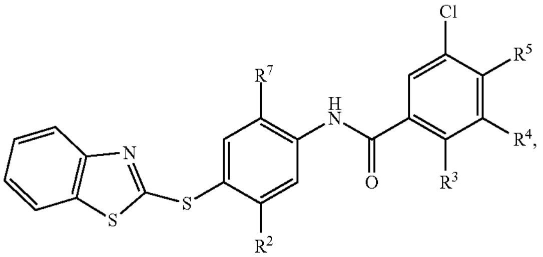

wherein R 2, $R^3$, $R^4$, $R^5$, and $R^7$ are as described herein; or a pharmaceutically acceptable salt thereof.

In accordance with one embodiment a compound of formula II:

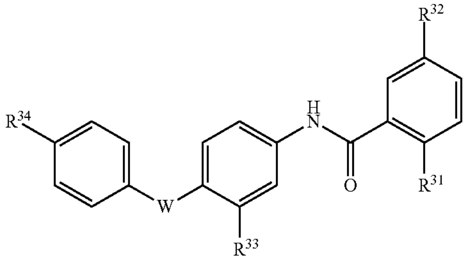

is provided wherein

W is O or CHCN;

$R^{31}$ is OH, or $OCH_3$;

$R^{32}$ is halo, optionally Cl or Br;

$R^{33}$ is H, or halo;

$R^{34}$ is H, or halo. In one embodiment W is O or CHCN, $R^{31}$ is OH, $R^{32}$ is Cl, and $R^{33}$ and $R^{34}$ are independently H, or Cl. In one embodiment W is O, $R^{31}$ is OH, $R^{32}$ is Cl, and $R^{33}$ and $R^{34}$ are independently H, or Cl. In one embodiment the compound has the structure of

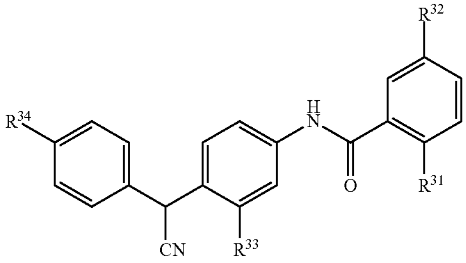

wherein $R^{31}$ is OH, $R^{32}$ is Cl, and $R^{33}$ and $R^{34}$ are independently H, or Cl. In one embodiment the compounds of I, Ia, Ib and II are used as anti-microbial agents to inhibit replication and/or kill microbial organisms, including bacteria, such as *S. aureus* or other gram negative bacteria. In one embodiment the compounds of I, Ia, Ib and II are used to inhibiting chaperonin-mediated refolding as measured in the dMDH refolding assay of Example 76. In one embodiment the method of killing or inhibiting the growth of bacteria comprises contacting bacteria with a compound of formula I, Ia, Ib, or II, or a pharmaceutically acceptable salt thereof.

In one embodiment a compound of formula III:

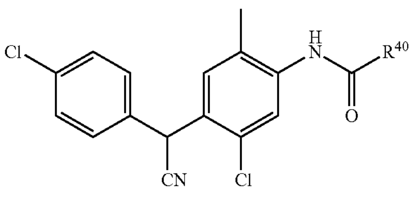

is provided wherein $R^{40}$ is a compound of the formula

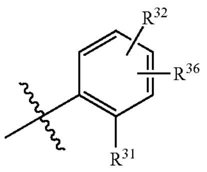

wherein $R^{31}$ is OH or $OCH_3$;

$R^{32}$ and $R^{36}$ are independently H, Br or Cl, with the proviso that $R^{32}$ and $R^{36}$ are not both H. In one embodiment $R^{31}$ is OH, $R^{36}$ is H, and $R^{32}$ is Br or Cl. In one embodiment $R^{40}$ has the structure of

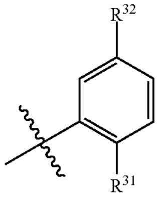

wherein $R^{31}$ is OH, and $R^{32}$ is Br or Cl.

In some embodiments, a method of killing or inhibiting the growth of bacteria comprising contacting the bacteria with a compound of formula I, Ia, Ib, II, or III, or a pharmaceutically acceptable salt thereof, is provided. In some embodiments, the bacteria is Gram-positive. In some embodiments, the bacteria is Gram-negative. In some embodiments, the bacteria comprise Gram-positive bacteria, Gram-negative bacteria, or a combination thereof. In some embodiments, the bacteria are capable of forming a biofilm. In some embodiments, the genus of bacteria are selected from a group consisting of *Enterococcus, Staphylococcus, Klebsiella, Acinetobacter, Pseudomonas*, and *Enterobacter* or a combination thereof. In some embodiments, the bacteria are *Enterococcus faecium, Staphylococcus aureus*, methicillin-resistant *Staphylococcus aureus* (MRSA), *Klebsiella pneumoniae, Acinetobacter baumannii, Pseudomonas aeruginosa, Enterobacter cloacae*, or a combination thereof.

In some embodiments, a method of killing or inhibiting the growth of bacteria forming a biofilm is provided. The method comprises contacting the bacteria with a compound of formula I, Ia, Ib, II, III, or a pharmaceutically acceptable salt thereof.

In some embodiments, a method of killing or inhibiting the growth of bacteria within a biofilm is provided. The method comprises contacting the biofilm with a compound of formula I, Ia, Ib, II, III or a pharmaceutically acceptable salt thereof.

The following represent illustrative embodiments of compounds of the formula I, Ia, or Ib:

| Compound | Structure | Name |
| --- | --- | --- |
| 45 | 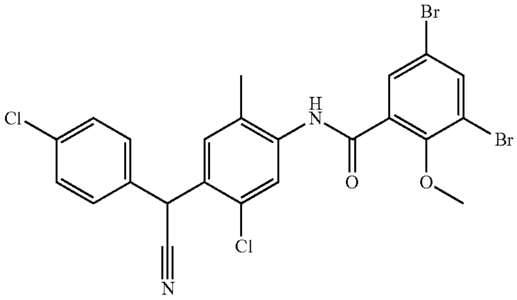 [SMILES: COc1c(Br)cc(Br)cc1C(=O)Nc1cc(Cl)c(C(C#N)c2ccc(Cl)cc2)cc1C] | 3,5-dibromo-N-(5-chloro-4-((4-chlorophenyl)(cyano)methyl)-2-methylphenyl)-2-methoxybenzamide |
| 46 | 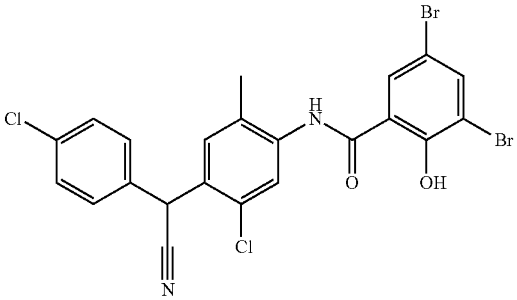 [SMILES: Cc1cc(C(C#N)c2ccc(Cl)cc2)c(Cl)cc1NC(=O)c1cc(Br)cc(Br)c1O] | 3,5-dibromo-N-(5-chloro-4-((4-chlorophenyl)(cyano)methyl)-2-methylphenyl)-2-hydroxybenzamide |
| 47 | 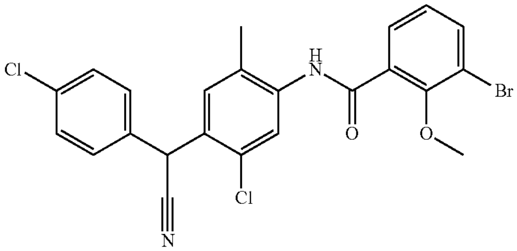 [SMILES: COc1c(Br)cccc1C(=O)Nc1cc(Cl)c(C(C#N)c2ccc(Cl)cc2)cc1C] | 3-bromo-N-(5-chloro-4-((4-chlorophenyl)(cyano)methyl)-2-methylphenyl)-2-methoxybenzamide |
| 48 | 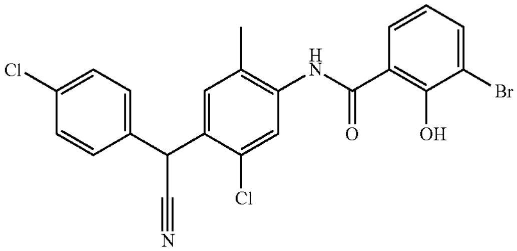 [SMILES: Cc1cc(C(C#N)c2ccc(Cl)cc2)c(Cl)cc1NC(=O)c1cccc(Br)c1O] | 3-bromo-N-(5-chloro-4-((4-chlorophenyl)(cyano)methyl)-2-methylphenyl)-2-hydroxybenzamide. |
| 49 | 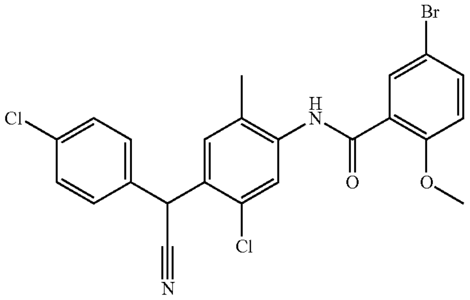 [SMILES: COc1ccc(Br)cc1C(=O)Nc1cc(Cl)c(C(C#N)c2ccc(Cl)cc2)cc1C] | 5-bromo-N-(5-chloro-4-((4-chlorophenyl)(cyano)methyl)-2-methylphenyl)-2-methoxybenzamide |

-continued

| Compound | Structure | Name |
|---|---|---|
| 50 | 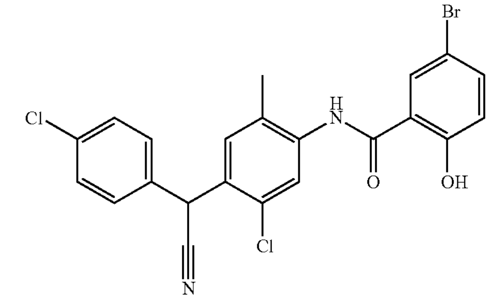 | 5-bromo-N-(5-chloro-4-((4-chlorophenyl)(cyano)methyl)-2-methylphenyl)-2-hydroxybenzamide. |
| 51 | 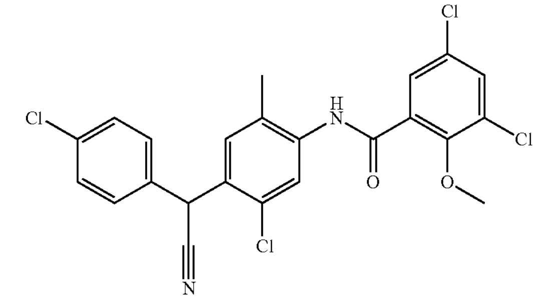 [SMILES: COc1c(Cl)cc(Cl)cc1C(=O)Nc1cc(Cl)c(C(C#N)c2ccc(Cl)cc2)cc1C] | 3,5-dichloro-N-(5-chloro-4-((4-chlorophenyl)(cyano)methyl)-2-methylphenyl)-2-methoxybenzamide |
| 52 | 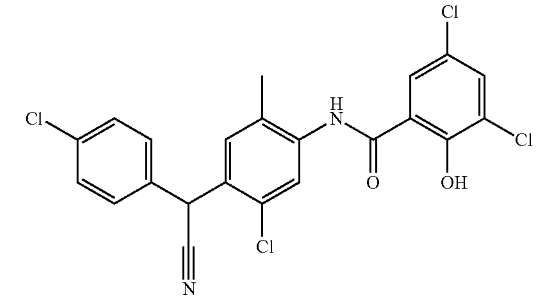 [SMILES: Cc1cc(C(C#N)c2ccc(Cl)cc2)c(Cl)cc1NC(=O)c1cc(Cl)cc(Cl)c1O] | 3,5-dichloro-N-(5-chloro-4-((4-chlorophenyl)(cyano)methyl)-2-methylphenyl)-2-hydroxybenzamide |
| 53 | 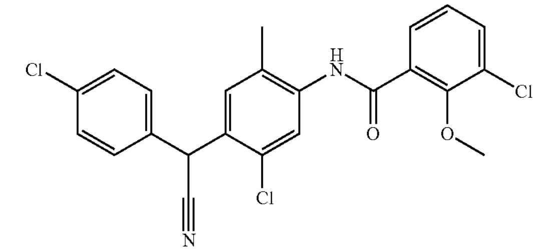 | 3-chloro-N-(5-chloro-4-((4-chlorophenyl)(cyano)methyl)-2-methylphenyl)-2-methoxybenzamide |
| 54 | 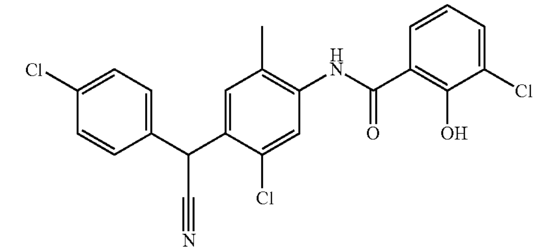 [SMILES: Cc1cc(C(C#N)c2ccc(Cl)cc2)c(Cl)cc1NC(=O)c1cccc(Cl)c1O] | 3-chloro-N-(5-chloro-4-((4-chlorophenyl)(cyano)methyl)-2-methylphenyl)-2-hydroxy benzamide |

-continued

| Compound | Structure | Name |
|---|---|---|
| 55 | 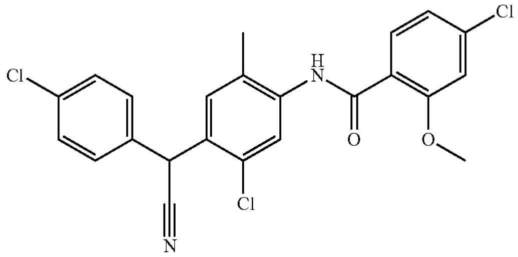 [SMILES: COc1cc(Cl)ccc1C(=O)Nc1cc(Cl)c(C(C#N)c2ccc(Cl)cc2)cc1C] | 4-chloro-N-(5-chloro-4-((4-chlorophenyl)(cyano)methyl)-2-methylphenyl)-2-methoxybenzamide |
| 56 | 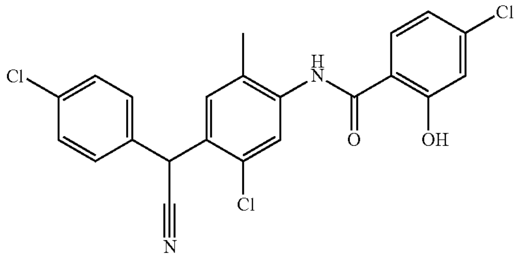 [SMILES: Cc1cc(C(C#N)c2ccc(Cl)cc2)c(Cl)cc1NC(=O)c1ccc(Cl)cc1O] | 4-chloro-N-(5-chloro-4-((4-chlorophenyl)(cyano)methyl)-2-methylphenyl)-2-hydroxybenzamide |
| 57 | 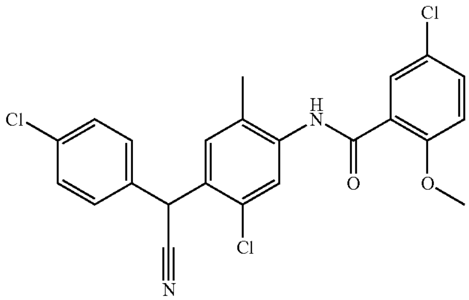 [SMILES: COc1ccc(Cl)cc1C(=O)Nc1cc(Cl)c(C(C#N)c2ccc(Cl)cc2)cc1C] | 5-chloro-N-(5-chloro-4-((4-chlorophenyl)(cyano)methyl)-2-methylphenyl)-2-methoxybenzamide |
| 58 | 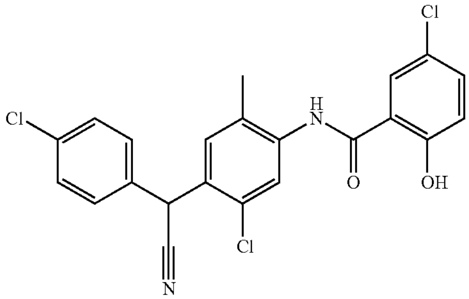 [SMILES: Cc1cc(C(C#N)c2ccc(Cl)cc2)c(Cl)cc1NC(=O)c1cc(Cl)ccc1O] | 5-chloro-N-(5-chloro-4-((4-chlorophenyl)(cyano)methyl)-2-methylphenyl)-2-hydroxybenzamide |
| 59 | 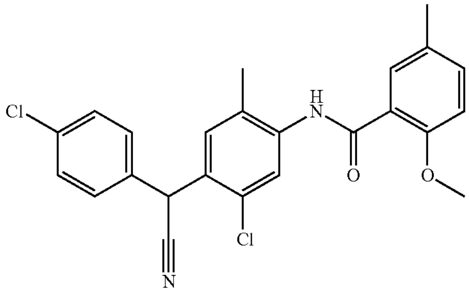 [SMILES: COc1ccc(C)cc1C(=O)Nc1cc(Cl)c(C(C#N)c2ccc(Cl)cc2)cc1C] | N-(5-chloro-4-((4-chlorophenyl)(cyano)methyl)-2-methylphenyl)-2-methoxy-5-methylbenzamide |

-continued

| Compound | Structure | Name |
|---|---|---|
| 60 | 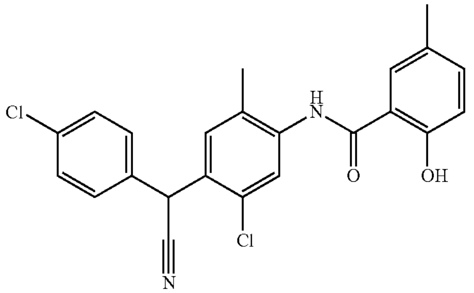 [SMILES: Cc1ccc(O)c(C(=O)Nc2cc(Cl)c(C(C#N)c3ccc(Cl)cc3)cc2C)c1] | N-(5-chloro-4-((4-chlorophenyl)(cyano)methyl)-2-methylphenyl)-2-hydroxy-5-methylbenzamide |
| 61 | 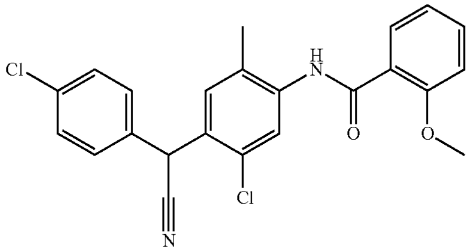 [SMILES: COc1ccccc1C(=O)Nc1cc(Cl)c(C(C#N)c2ccc(Cl)cc2)cc1C] | N-(5-chloro-4-((4-chlorophenyl)(cyano)methyl)-2-methylphenyl)-2-methoxybenzamide |
| 62 | 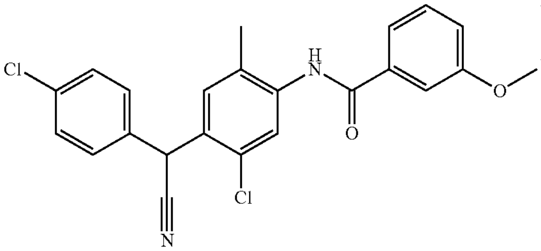 | N-(5-chloro-4-((4-chlorophenyl)(cyano)methyl)-2-methylphenyl)-3-methoxybenzamide |
| 63 | 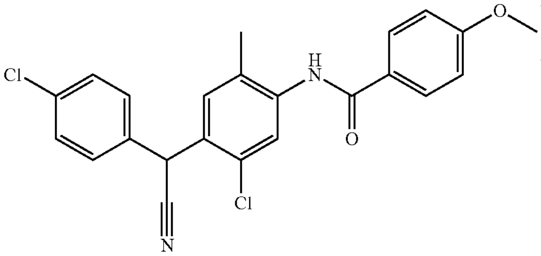 | N-(5-chloro-4-((4-chlorophenyl)(cyano)methyl)-2-methylphenyl)-4-methoxybenzamide |
| 64 | 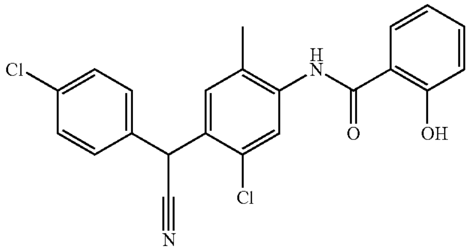 [SMILES: Cc1cc(C(C#N)c2ccc(Cl)cc2)c(Cl)cc1NC(=O)c1ccccc1O] | N-(5-chloro-4-((4-chlorophenyl)(cyano)methyl)-2-methylphenyl)-2-hydroxybenzamide |
| 65 | 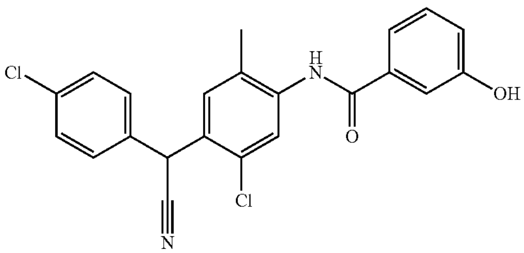 [SMILES: Cc1cc(C(C#N)c2ccc(Cl)cc2)c(Cl)cc1NC(=O)c1cccc(O)c1] | N-(5-chloro-4-((4-chlorophenyl)(cyano)methyl)-2-methylphenyl)-3-hydroxybenzamide |

-continued

| Compound | Structure | Name |
| --- | --- | --- |
| 66 | 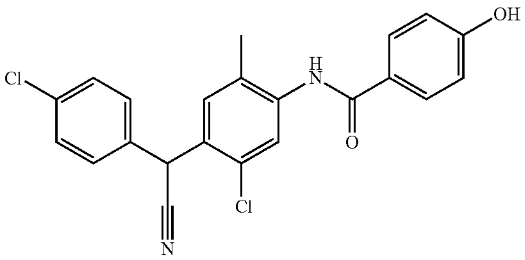 [SMILES: Cc1cc(C(C#N)c2ccc(Cl)cc2)c(Cl)cc1NC(=O)c1ccc(O)cc1] | N-(5-chloro-4-((4-chlorophenyl)(cyano)methyl)-2-methylphenyl)-4-hydroxybenzamide |
| 67 | 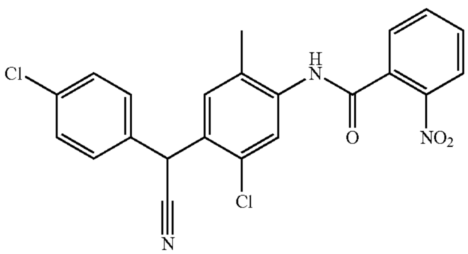 | N-(5-chloro-4-((4-chlorophenyl)(cyano)methyl)-2-methylphenyl)-2-nitrobenzamide |
| 68 | 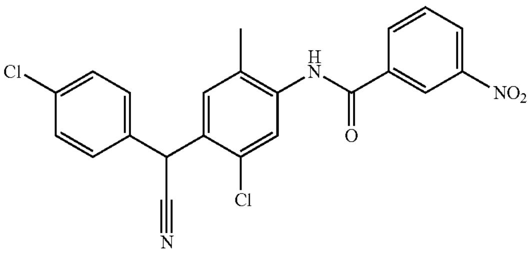 | N-(5-chloro-4-((4-chlorophenyl)(cyano)methyl)-2-methylphenyl)-3-nitrobenzamide. |
| 69 | 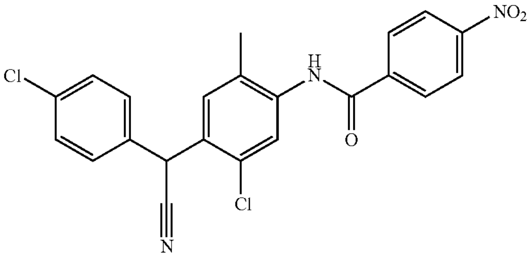 [SMILES: Cc1cc(C(C#N)c2ccc(Cl)cc2)c(Cl)cc1NC(=O)c1ccc([N+](=O)[O-])cc1] | N-(5-chloro-4-((4-chlorophenyl)(cyano)methyl)-2-methylphenyl)-4-nitrobenzamide |
| 70 | 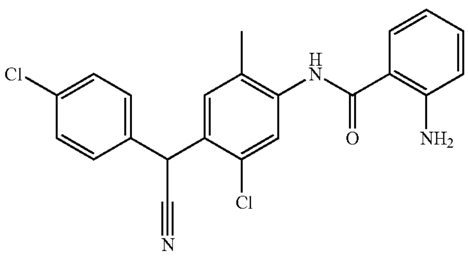 | 2-amino-N-(5-chloro-4-((4-chlorophenyl)(cyano)methyl)-2-methylphenyl)benzamide. |
| 71 | 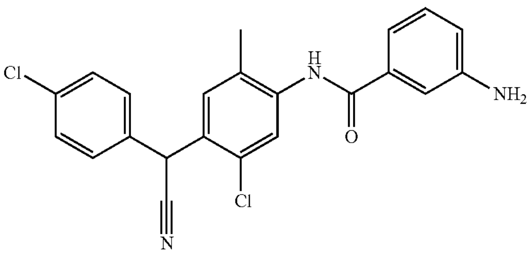 | 3-amino-N-(5-chloro-4-((4-chlorophenyl)(cyano)methyl)-2-methylphenyl)benzamide |

-continued

| Compound | Structure | Name |
| --- | --- | --- |
| 72 | 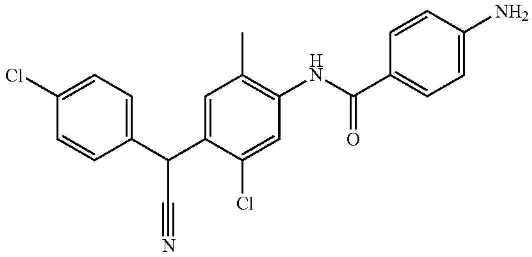 | 4-amino-N-(5-chloro-4-((4-chlorophenyl)(cyano)methyl)-2-methylphenyl)benzamide |
| 73 | 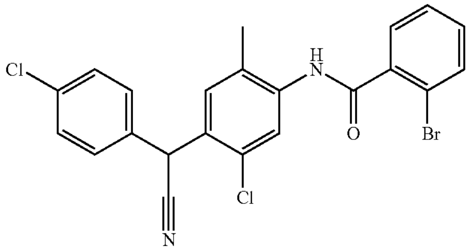 | 2-bromo-N-(5-chloro-4-((4-chlorophenyl)(cyano)methyl)-2-methylphenyl)benzamide |
| 74 | 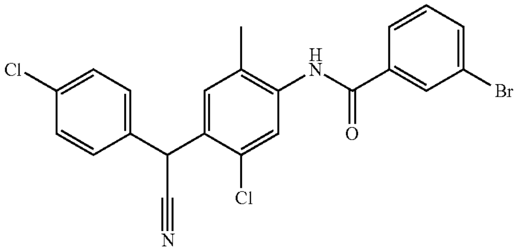 [SMILES: Cc1cc(C(C#N)c2ccc(Cl)cc2)c(Cl)cc1NC(=O)c1cccc(Br)c1] | 3-bromo-N-(5-chloro-4-((4-chlorophenyl)(cyano)methyl)-2-methylphenyl)benzamide |
| 75 | 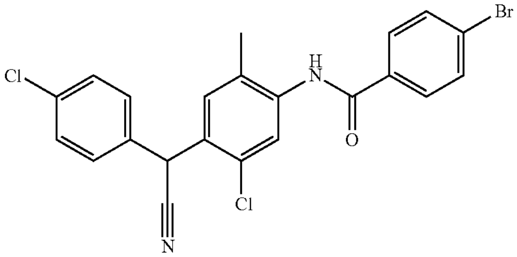 [SMILES: Cc1cc(C(C#N)c2ccc(Cl)cc2)c(Cl)cc1NC(=O)c1ccc(Br)cc1] | 4-bromo-N-(5-chloro-4-((4-chlorophenyl)(cyano)methyl)-2-methylphenyl)benzamide |
| 76 | 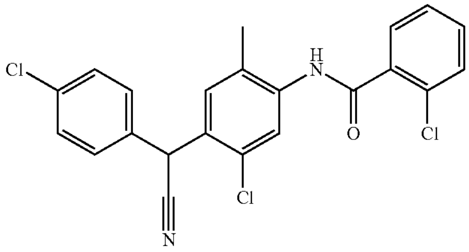 | 2-chloro-N-(5-chloro-4-((4-chlorophenyl)(cyano)methyl)-2-methylphenyl)benzamide |
| 77 | 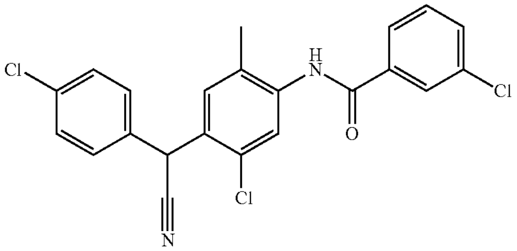 [SMILES: Cc1cc(C(C#N)c2ccc(Cl)cc2)c(Cl)cc1NC(=O)c1cccc(Cl)c1] | 3-chloro-N-(5-chloro-4-((4-chlorophenyl)(cyano)methyl)-2-methylphenyl)benzamide |

-continued

| Compound | Structure | Name |
|---|---|---|
| 78 | 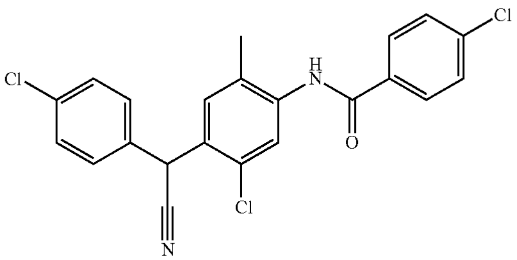 | 4-chloro-N-(5-chloro-4-((4-chlorophenyl)(cyano)methyl)-2-methylphenyl)benzamide |
| 79 | 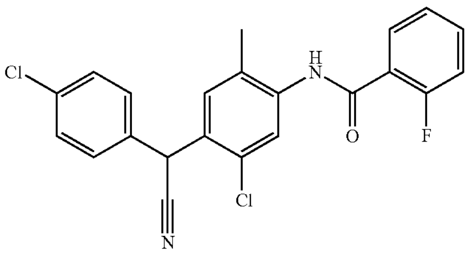 [SMILES: Cc1cc(C(C#N)c2ccc(Cl)cc2)c(Cl)cc1NC(=O)c1ccccc1F] | N-(5-chloro-4-((4-chlorophenyl)(cyano)methyl)-2-methylphenyl)-2-fluorobenzamide |
| 80 | 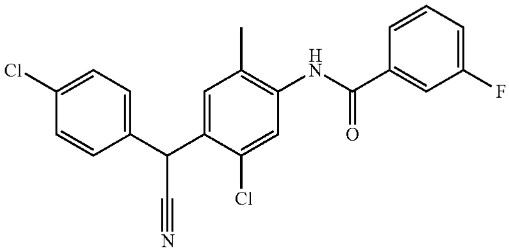 [SMILES: Cc1cc(C(C#N)c2ccc(Cl)cc2)c(Cl)cc1NC(=O)c1cccc(F)c1] | N-(5-chloro-4-((4-chlorophenyl)(cyano)methyl)-2-methylphenyl)-3-fluorobenzamide |
| 81 | 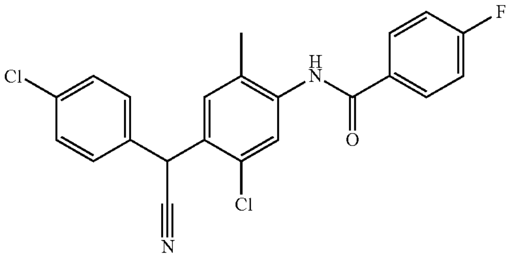 [SMILES: Cc1cc(C(C#N)c2ccc(Cl)cc2)c(Cl)cc1NC(=O)c1ccc(F)cc1] | N-(5-chloro-4-((4-chlorophenyl)(cyano)methyl)-2-methylphenyl)-4-fluorobenzamide |
| 82 | 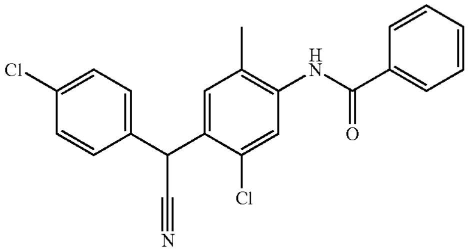 [SMILES: Cc1cc(C(C#N)c2ccc(Cl)cc2)c(Cl)cc1NC(=O)c1ccccc1] | N-(5-chloro-4-((4-chlorophenyl)(cyano)methyl)-2-methylphenyl)benzamide |
| 83 | 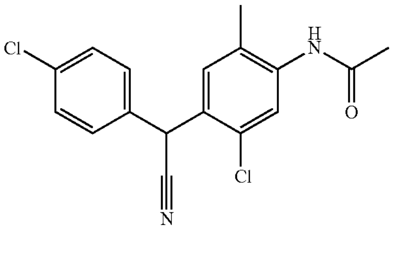 [SMILES: CC(=O)Nc1cc(Cl)c(C(C#N)c2ccc(Cl)cc2)cc1C] | N-(5-chloro-4-((4-chlorophenyl)(cyano)methyl)-2-methylphenyl)acetamide |

-continued

| Compound | Structure | Name |
|---|---|---|
| 84 | 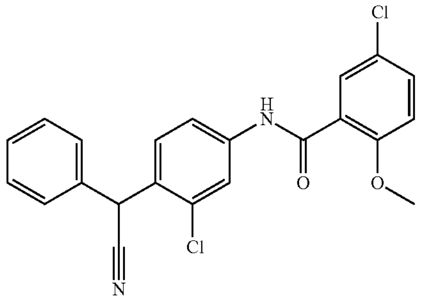 [SMILES: COc1ccc(Cl)cc1C(=O)Nc1ccc(C(C#N)c2ccccc2)c(Cl)c1] | 5-chloro-N-(4-(cyano(phenyl)methyl)phenyl)-2-methoxybenzamide |
| 85 | 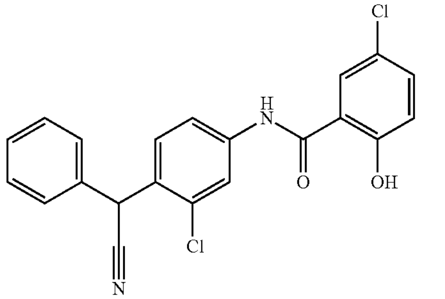 [SMILES: N#CC(c1ccccc1)c1ccc(NC(=O)c2cc(Cl)ccc2O)cc1Cl] | 5-chloro-N-(4-(cyano(phenyl)methyl)phenyl)-2-hydroxybenzamide |
| 86 | 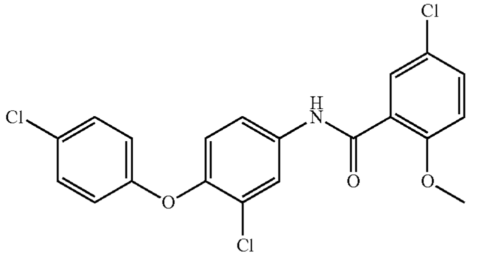 [SMILES: COc1ccc(Cl)cc1C(=O)Nc1ccc(Oc2ccc(Cl)cc2)c(Cl)c1] | 5-chloro-N-(3-chloro-4-(4-chlorophenoxy)phenyl)-2-methoxybenzamide |
| 87 | 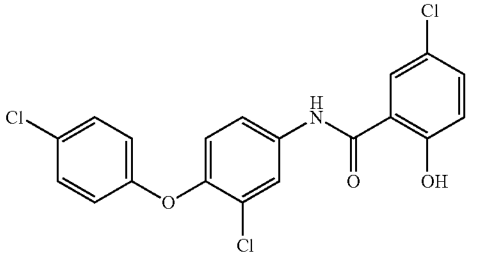 [SMILES: O=C(Nc1ccc(Oc2ccc(Cl)cc2)c(Cl)c1)c1cc(Cl)ccc1O] | 5-chloro-N-(3-chloro-4-(4-chlorophenoxy)phenyl)-2-hydroxybenzamide |
| 88 | 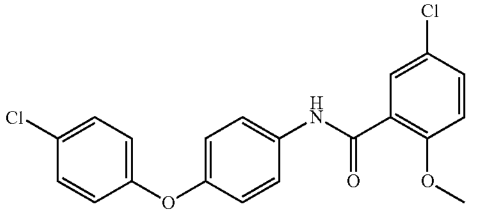 [SMILES: COc1ccc(Cl)cc1C(=O)Nc1ccc(Oc2ccc(Cl)cc2)cc1] | 5-chloro-N-(4-(4-chlorophenoxy)phenyl)-2-methoxybenzamide |
| 89 | 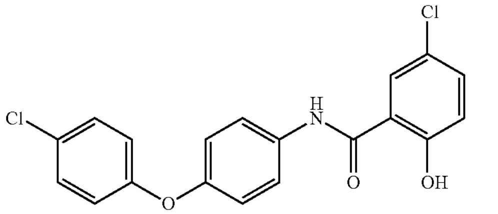 [SMILES: O=C(Nc1ccc(Oc2ccc(Cl)cc2)cc1)c1cc(Cl)ccc1O] | 5-chloro-N-(4-(4-chlorophenoxy)phenyl)-2-hydroxybenzamide |

-continued
| Compound | Structure | Name |
|---|---|---|
| 90 | 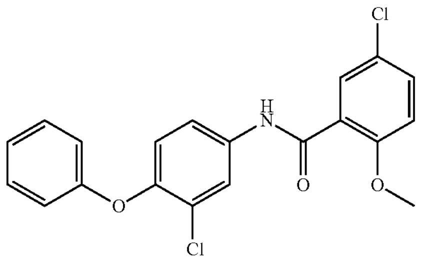 [SMILES: COc1ccc(Cl)cc1C(=O)Nc1ccc(Oc2ccccc2)c(Cl)c1] | 5-chloro-N-(3-chloro-4-phenoxyphenyl)-2-methoxybenzamide |
| 91 | 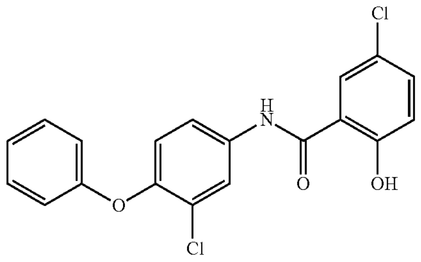 [SMILES: O=C(Nc1ccc(Oc2ccccc2)c(Cl)c1)c1cc(Cl)ccc1O] | 5-chloro-N-(3-chloro-4-phenoxyphenyl)-2-hydroxybenzamide |
| 92 | 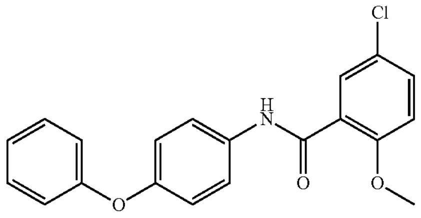 [SMILES: COc1ccc(Cl)cc1C(=O)Nc1ccc(Oc2ccccc2)cc1] | 5-chloro-2-methoxy-N-(4-phenoxyphenyl)benzamide |
| 93 | 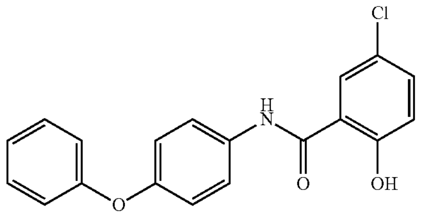 [SMILES: O=C(Nc1ccc(Oc2ccccc2)cc1)c1cc(Cl)ccc1O] | 5-chloro-2-hydroxy-N-(4-phenoxyphenyl)benzamide |
| 94 | 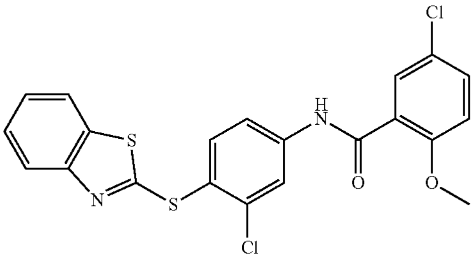 [SMILES: COc1ccc(Cl)cc1C(=O)Nc1ccc(Sc2nc3ccccc3s2)c(Cl)c1] | N-(4-(benzo[d]thiazol-2-ylthio)-3-chlorophenyl)-5-chloro-2-methoxy benzamide |
| 95 | 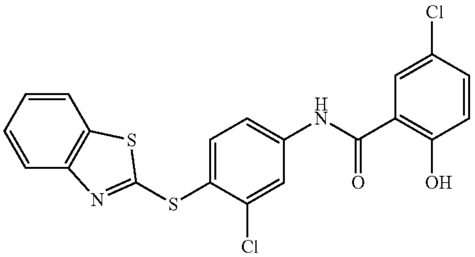 [SMILES: O=C(Nc1ccc(Sc2nc3ccccc3s2)c(Cl)c1)c1cc(Cl)ccc1O] | N-(4-(benzo[d]thiazol-2-ylthio)-3-chlorophenyl)-5-chloro-2-hydroxybenzamide |

-continued
| Compound | Structure | Name |
| --- | --- | --- |
| 96 | 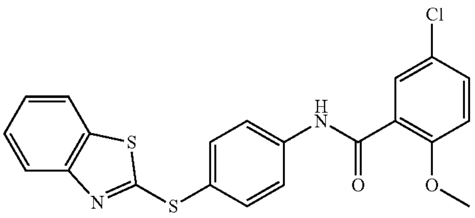 [SMILES: COc1ccc(Cl)cc1C(=O)Nc1ccc(Sc2nc3ccccc3s2)cc1] | N-(4-(benzo[d]thiazol-2-ylthio)phenyl)-5-chloro-2-methoxybenzamide |
| 97 | 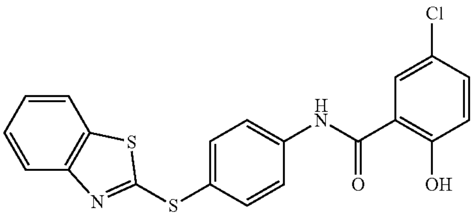 [SMILES: O=C(Nc1ccc(Sc2nc3ccccc3s2)cc1)c1cc(Cl)ccc1O] | N-(4-(benzo[d]thiazol-2-ylthio)phenyl)-5-chloro-2-hydroxy benzamide |
| 98 | 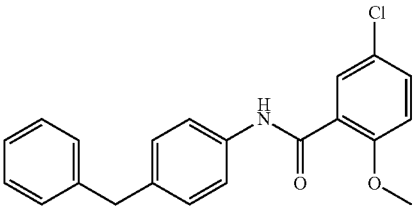 [SMILES: COc1ccc(Cl)cc1C(=O)Nc1ccc(Cc2ccccc2)cc1] | N-(4-benzylphenyl)-5-chloro-2-methoxybenzamide |
| 99 | 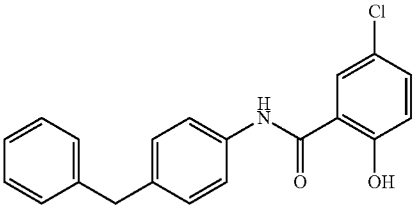 [SMILES: O=C(Nc1ccc(Cc2ccccc2)cc1)c1cc(Cl)ccc1O] | N-(4-benzylphenyl)-5-chloro-2-hydroxy benzamide |
| 100 | 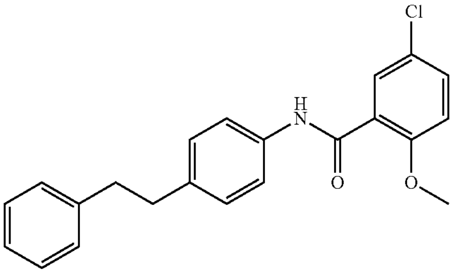 | 5-chloro-2-methoxy-N-(4-phenethylphenyl)benzamide |
| 101 | 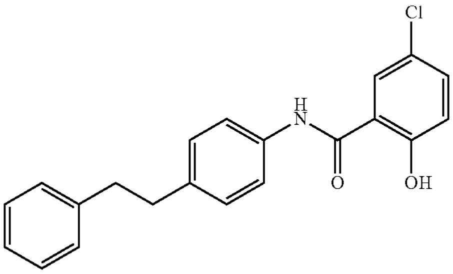 [SMILES: O=C(Nc1ccc(CCc2ccccc2)cc1)c1cc(Cl)ccc1O] | 5-chloro-2-methoxy-N-(4-phenethylphenyl)benzamide |

-continued
| Compound | Structure | Name |
| --- | --- | --- |
| 102 | 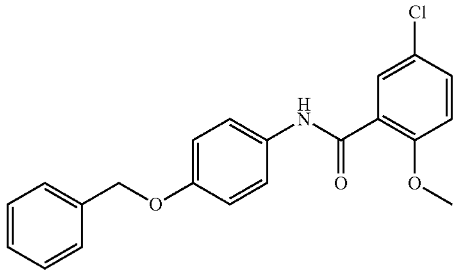 | N-(4-(benzyloxy)phenyl)-5-chloro-2-methoxybenzamide |
| 103 | 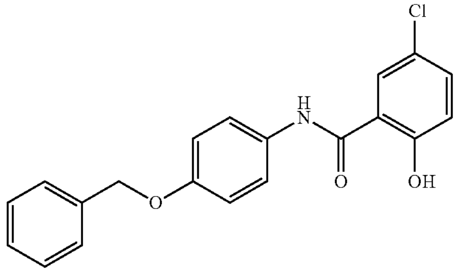 | N-(4-(benzyloxy)phenyl)-5-chloro-2-hydroxybenzamide |
| 104 | 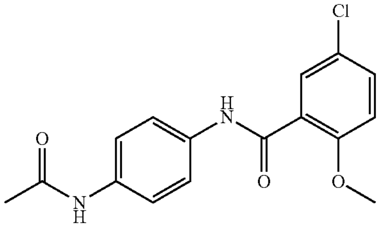 [SMILES: COc1ccc(Cl)cc1C(=O)Nc1ccc(NC(C)=O)cc1] | N-(4-acetamidophenyl)-5-chloro-2-methoxybenzamide |
| 105 | 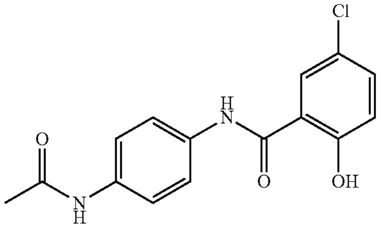 [SMILES: CC(=O)Nc1ccc(NC(=O)c2cc(Cl)ccc2O)cc1] | N-(4-acetamidophenyl)-5-chloro-2-hydroxybenzamide |
| 106 | 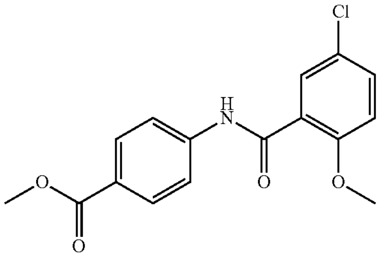 | Methyl 4-(5-chloro-2-methoxybenzamido)benzoate |
| 107 | 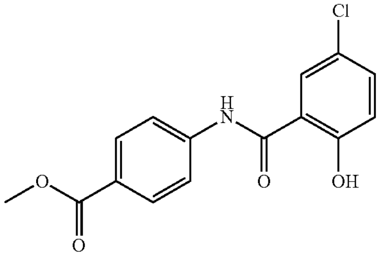 [SMILES: COC(=O)c1ccc(NC(=O)c2cc(Cl)ccc2O)cc1] | methyl 4-(5-chloro-2-hydroxybenzamido)benzoate |

-continued
| Compound | Structure | Name |
|---|---|---|
| 108 | 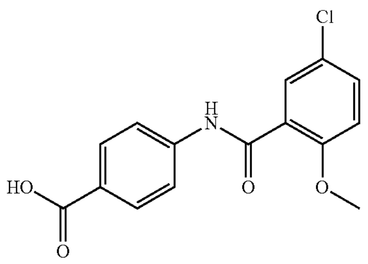 [SMILES: COc1ccc(Cl)cc1C(=O)Nc1ccc(C(=O)O)cc1] | 4-(5-chloro-2-methoxybenzamido)benzoic acid |
| 109 | 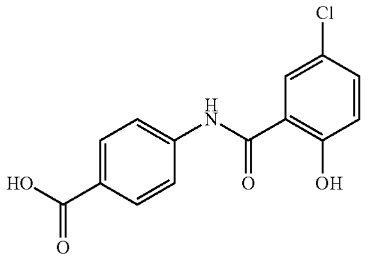 [SMILES: O=C(O)c1ccc(NC(=O)c2cc(Cl)ccc2O)cc1] | 4-(5-chloro-2-hydroxybenzamido)benzoic acid |
| 110 | 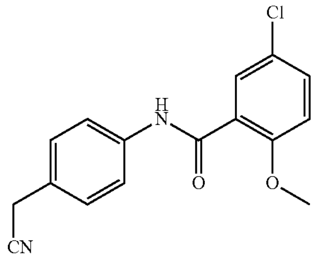 [SMILES: COc1ccc(Cl)cc1C(=O)Nc1ccc(CC#N)cc1] | 5-chloro-N-(4-(cyanomethyl)phenyl)-2-methoxybenzamide |
| 111 | 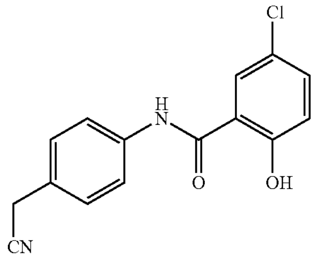 [SMILES: N#CCc1ccc(NC(=O)c2cc(Cl)ccc2O)cc1] | 5-chloro-N-(4-(cyanomethyl)phenyl)-2-hydroxybenzamide |
| 112 | 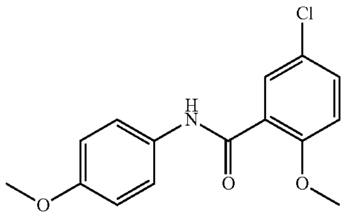 | 5-chloro-2-methoxy-N-(4-methoxyphenyl)benzamide |
| 113 | 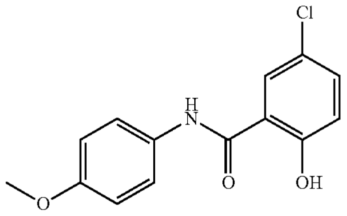 [SMILES: COc1ccc(NC(=O)c2cc(Cl)ccc2O)cc1] | 5-chloro-2-hydroxy-N-(4-methoxyphenyl)benzamide |

-continued

| Compound | Structure | Name |
| --- | --- | --- |
| 114 | 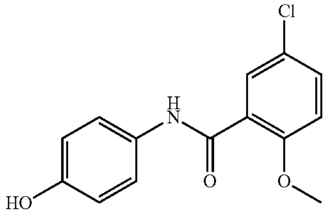 [SMILES: COc1ccc(Cl)cc1C(=O)Nc1ccc(O)cc1] | 5-chloro-N-(4-hydroxyphenyl)-2-methoxybenzamide |
| 115 | 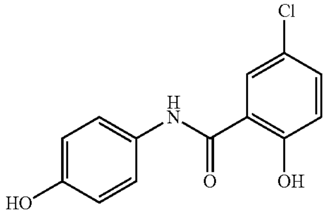 | 5-chloro-2-hydroxy-N-(4-hydroxyphenyl)benzamide |
| 116 | 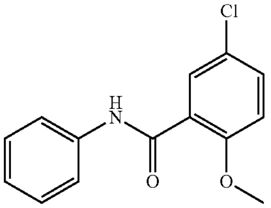 [SMILES: COc1ccc(Cl)cc1C(=O)Nc1ccccc1] | 5-chloro-2-methoxy-N-phenylbenzamide |
| 117 | 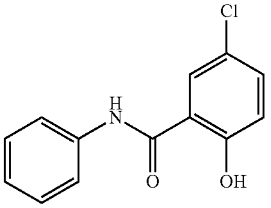 [SMILES: O=C(Nc1ccccc1)c1cc(Cl)ccc1O] | 5-chloro-2-hydroxy-N-phenylbenzamide |

Clause 1. A compound of the formula I

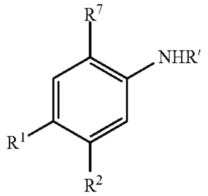

I wherein

R' is $C_1$-$C_6$ alkyl or

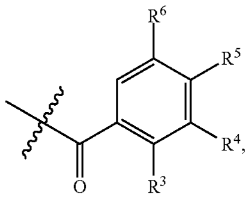

$R^1$ is H, —OH, —$OC_1$—$C_6$ alkyl, —NHC(O)$C_1$-$C_6$ alkyl, —C(O)$OC_1$—$C_6$ alkyl, —C(O)OH, $C_1$-$C_6$ alkyl, —S-heteroaryl, or

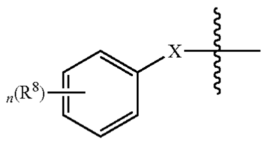

, wherein each hydrogen atom in $C_1$-$C_6$ alkyl is optionally substituted by —CN, $R^2$ is H or halo, each of $R^3$, $R^4$, $R^5$, and $R^6$ is independently H, —OH, halo, —O—$C_1$-$C_6$ alkyl, —$NO_2$, or —$NH_2$, $R^7$ is H or $C_1$-$C_6$ alkyl, X is —O—, —S—, —C($R^9$)($R^{10}$)$_m$—, or —C($R^9$)($R^{10}$)$_m$O—, optionally X is —O—, —S—, or —C($R^9$)(CN);

$R^8$ is halo, $R^9$ is H or —CN, $R^{10}$ is H or —CN, m is 1 or 2, and n is 0, 1, or 2;

or a pharmaceutically acceptable salt thereof, provided the compound of formula (I) is not

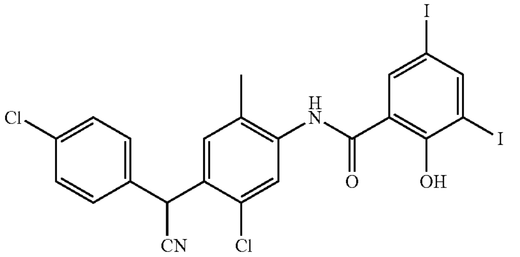

or (closantel)

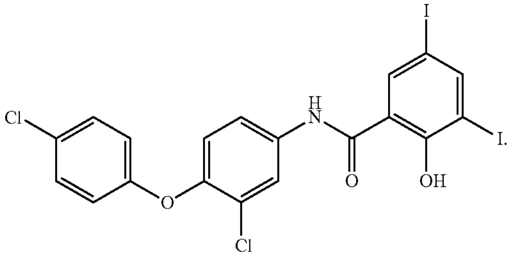

(rafoxanide)

Clause 2. The compound or pharmaceutically acceptable salt of clause 1, having the formula (Ia)

(Ia)

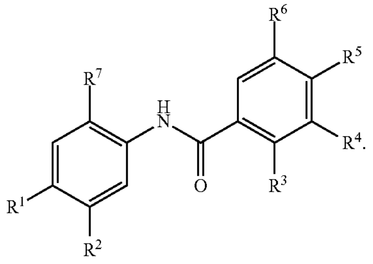

Clause 3. The compound or pharmaceutically acceptable salt of clause 1 or 2, wherein $R^3$ is —OH or —O—$C_1$-$C_6$ alkyl.

Clause 4. The compound or pharmaceutically acceptable salt of any of the preceding clauses, wherein $R^4$ is halo.

Clause 5. The compound or pharmaceutically acceptable salt of any of the preceding clauses, wherein $R^6$ is halo.

Clause 6. The compound or pharmaceutically acceptable salt of any of the preceding clauses, wherein $R^6$ is chloro.

Clause 7. The compound or pharmaceutically acceptable salt of any of the preceding clauses, wherein $R^7$ is $C_1$-$C_6$ alkyl.

Clause 8. The compound or pharmaceutically acceptable salt of any of the preceding clauses, wherein $R^7$ is methyl.

Clause 9. The compound or pharmaceutically acceptable salt of any of the preceding clauses, wherein X is —C(H)(CN)—.

Clause 10. The compound or pharmaceutically acceptable salt of any of the preceding clauses, wherein $R^8$ is chloro.

Clause 11. The compound or pharmaceutically acceptable salt of any of the preceding clauses, wherein $R^2$ is halo.

Clause 12. The compound or pharmaceutically acceptable salt of any of the preceding clauses, wherein $R^2$ is chloro.

Clause 13. The compound or pharmaceutically acceptable of clause 1, wherein $R^1$ is —S-benzothiazole.

Clause 14. The compound of pharmaceutically acceptable salt of clause 1, having the formula (Ib)

(Ib)

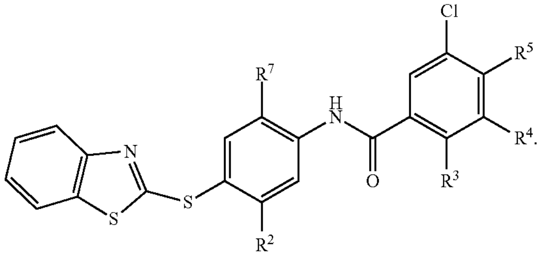

Clause 15. The compound of clause 14, wherein $R^2$ is H or halo, each of $R^3$, $R^4$, and $R^5$ is independently H, —OH, halo, —O—$C_1$-$C_6$ alkyl, —$NO_2$, or —$NH_2$, and $R^7$ is H or $C_1$-$C_6$ alkyl Clause 16. A method of killing or inhibiting the growth of bacteria said method comprising contacting said bacteria with a compound of formula I

I

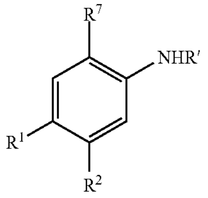

wherein

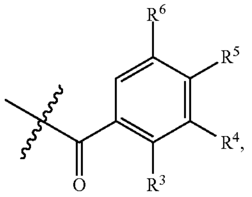

R' is $C_1$-$C_6$ alkyl or $R^1$ is H, —OH, —$OC_1$—$C_6$ alkyl, —NHC(O)$C_1$-$C_6$ alkyl, —C(O)$OC_1$—$C_6$ alkyl, —C(O)OH, $C_1$-$C_6$ alkyl, —S-heteroaryl, or

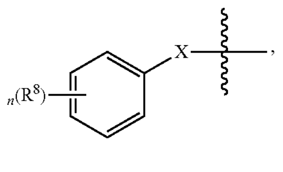

wherein each hydrogen atom in $C_1$-$C_6$ alkyl is optionally substituted by —CN, $R^2$ is H or halo, each of $R^3$, $R^4$, $R^5$, and $R^6$ is independently H, —OH, halo, —O—$C_1$-$C_6$ alkyl, $C_1$-$C_6$ alkyl, —$NO_2$, or —$NH_2$,
$R^7$ is H or $C_1$-$C_6$ alkyl,
X is —O—, —S—, —$C(R^9)(R^{10})_m$—, or —$C(R^9)(R^{10})_mO$—, optionally X is —O—, —S—, or —$C(R^9)(CN)$;
$R^8$ is halo,
$R^9$ is H or —CN,
$R^{10}$ is H or —CN,
m is 1 or 2, and
n is 0, 1, or 2;
or a pharmaceutically acceptable salt thereof, provided the compound of formula (I) is not

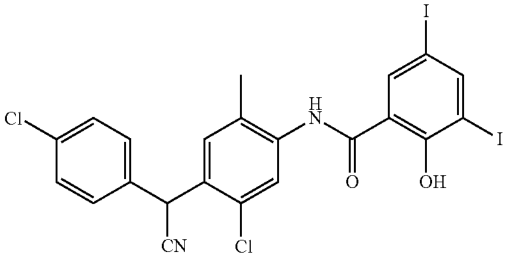

or (closantel)

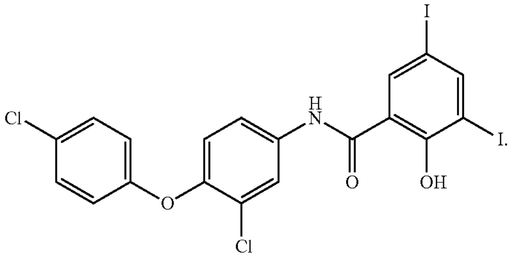

(rafoxanide)

Clause 17. The method of clause 16, having the formula (Ia)

(Ia)

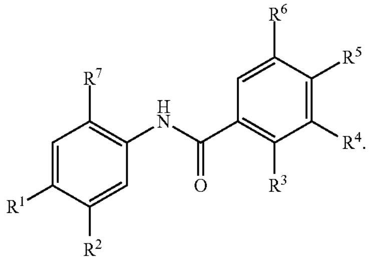

Clause 18. The method of clause 16 or 17, wherein $R^3$ is —OH or —O—$C_1$-$C_6$ alkyl.

Clause 19. The method of any of the preceding clauses, wherein $R^4$ is halo.

Clause 20. The method of any of the preceding clauses, wherein $R^6$ is halo.

Clause 21. The method of any of the preceding clauses, wherein $R^6$ is chloro.

Clause 22. The method of any of the preceding clauses, wherein $R^7$ is $C_1$-$C_6$ alkyl.

Clause 23. The method of any of the preceding clauses, wherein $R^7$ is methyl.

Clause 24. The method of any of the preceding clauses, wherein X is —C(H)(CN)—.

Clause 25. The method of any of the preceding clauses, wherein $R^8$ is chloro.

Clause 26. The method of any of the preceding clauses, wherein $R^2$ is halo.

Clause 27. The method of any of the preceding clauses, wherein $R^2$ is chloro.

Clause 28. The method of clause 16, wherein $R^1$ is —S-benzothiazole.

Clause 29. The method of clause 16 or 17, wherein the genus of bacteria are selected from a group consisting of *Enterococcus, Staphylococcus, Klebsiella, Acinetobacter, Pseudomonas*, and *Enterobacter* or a combination thereof.

Clause 30. The method of clause 29, wherein the bacteria are *Enterococcus faecium, Staphylococcus aureus*, methicillin-resistant *Staphylococcus aureus* (MRSA), *Klebsiella pneumoniae, Acinetobacter baumannii, Pseudomonas aeruginosa, Enterobacter cloacae*, or a combination thereof.

Clause 31. A pharmaceutical composition comprising a therapeutically effective amount of a compound according to any one of clauses 1-15.

Clause 32. A compound selected from the group consisting of

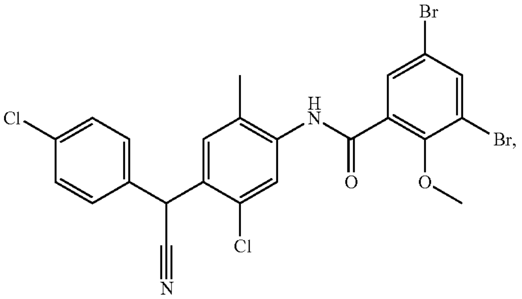

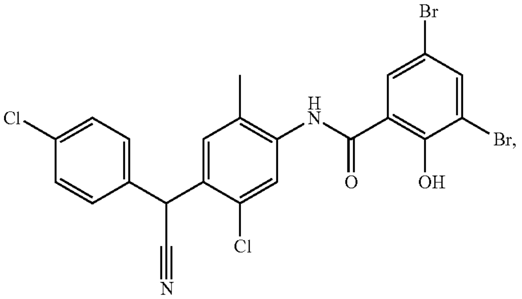

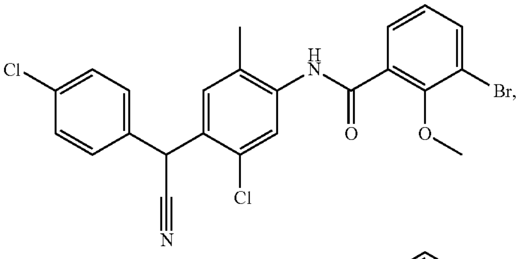

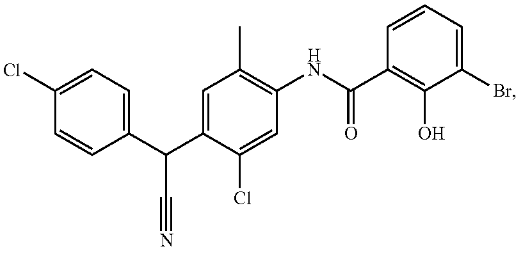

-continued
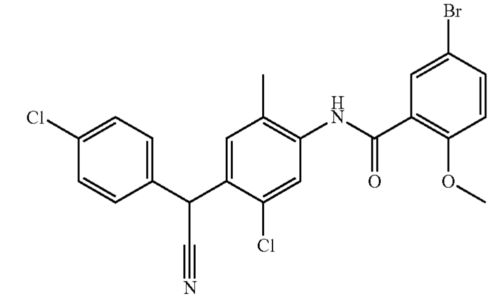
,
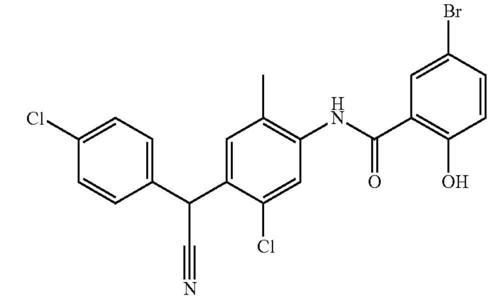
,
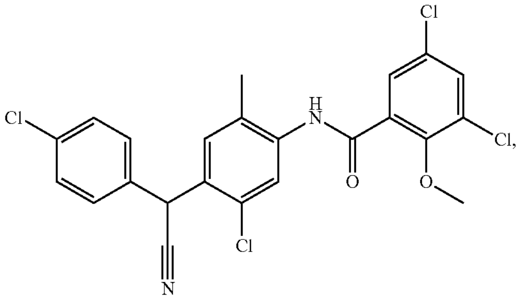
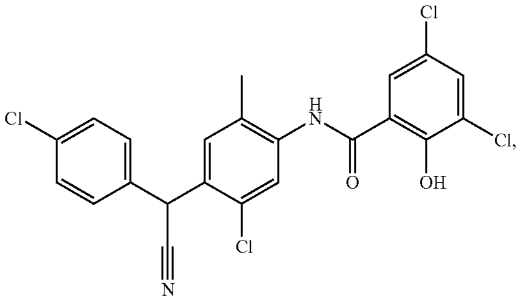
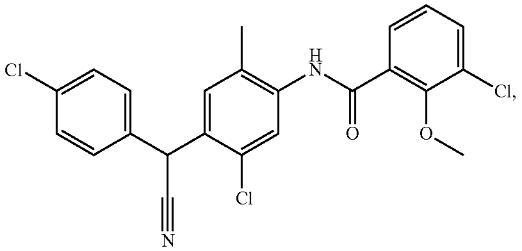
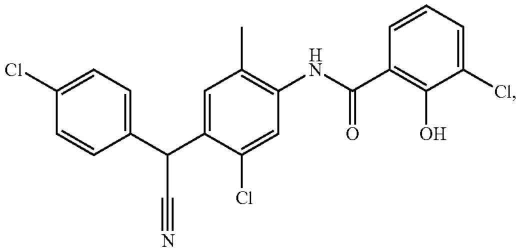
-continued
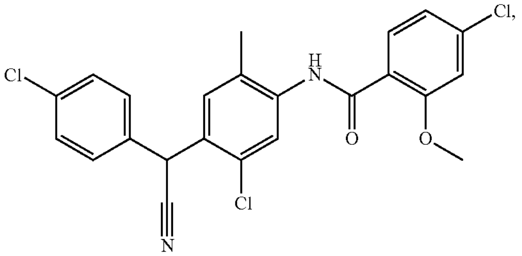
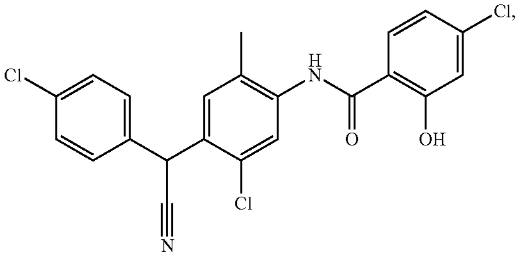
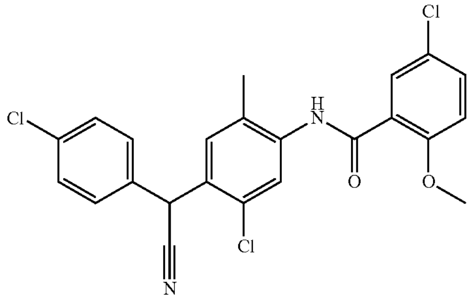
,
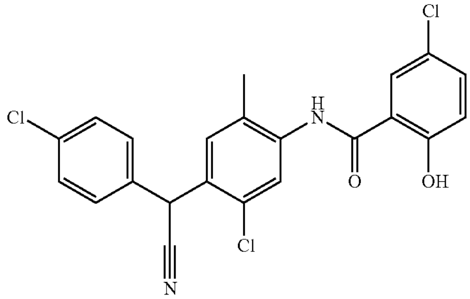
,
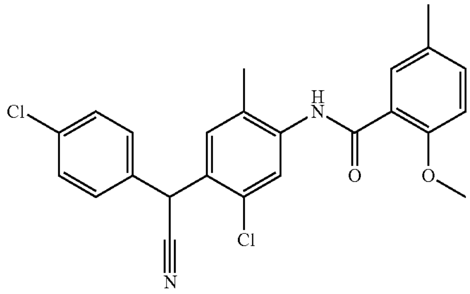
,
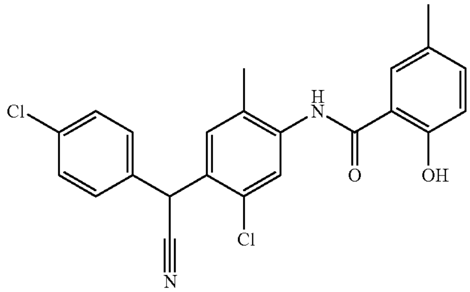
, -continued
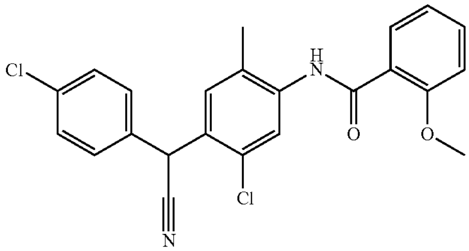
,
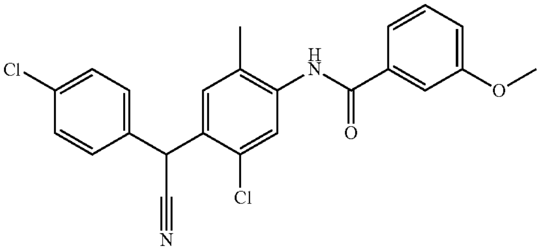
,
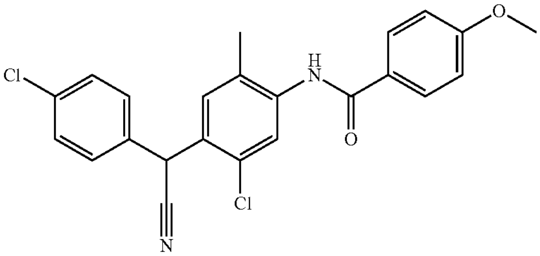
,
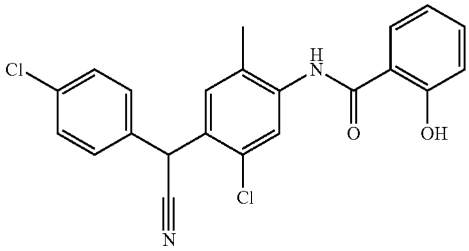
,
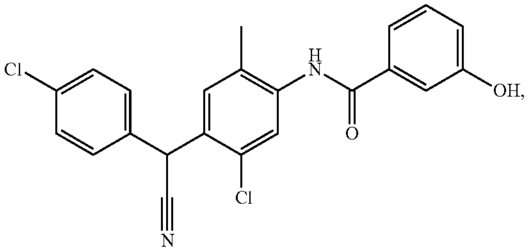
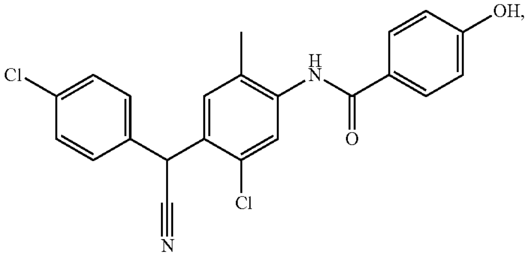
-continued
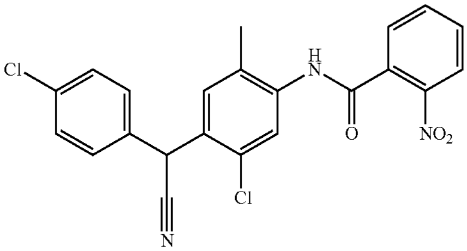
,
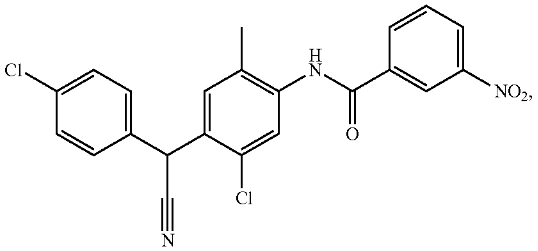
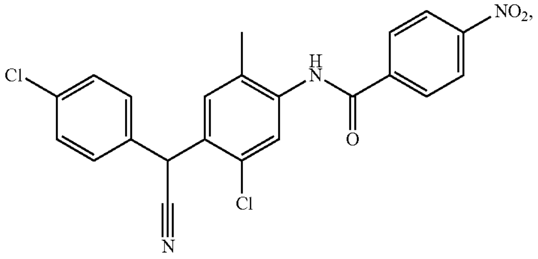
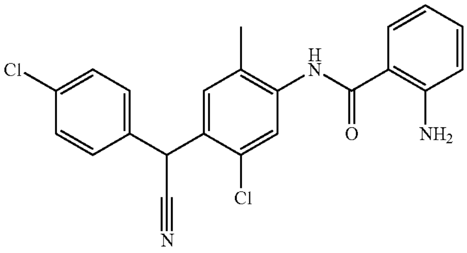
,
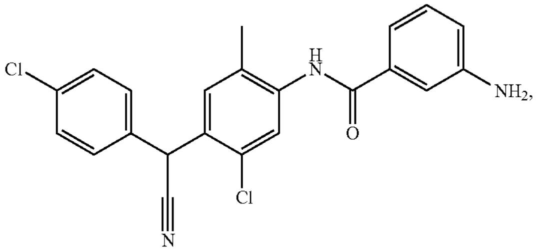
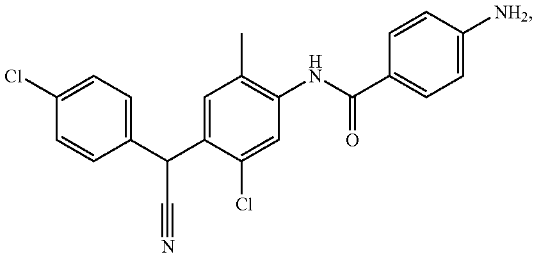

-continued
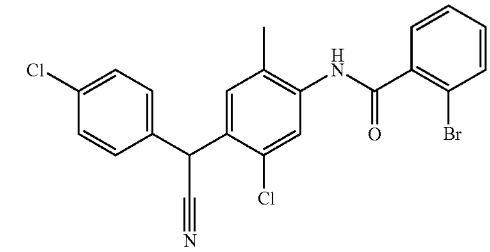
,
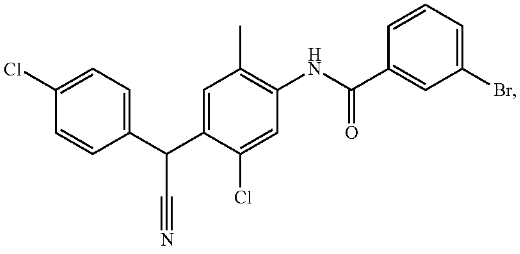
,
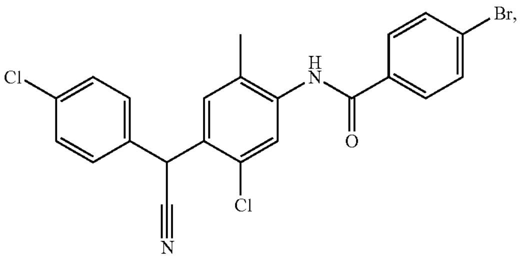
,
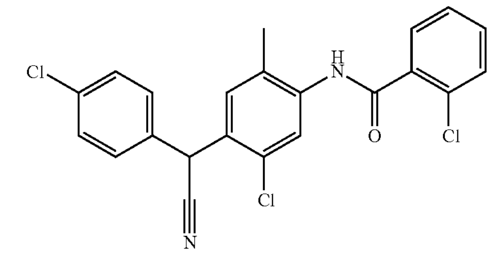
,
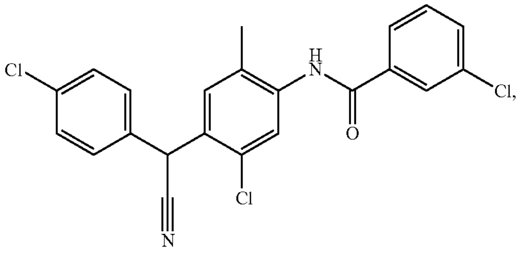
,
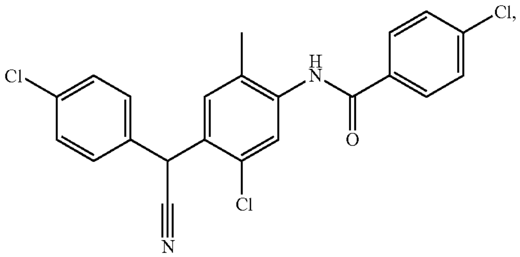
,
-continued
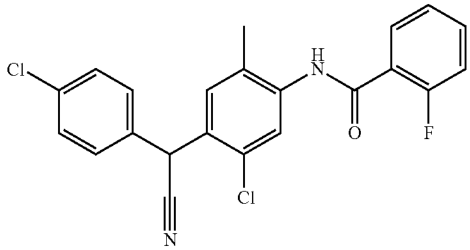
,
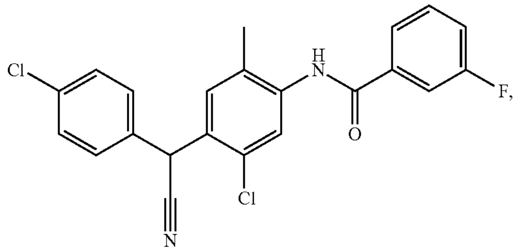
,
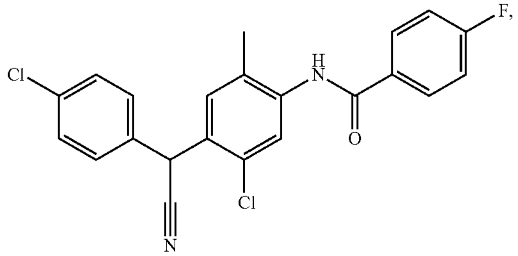
,
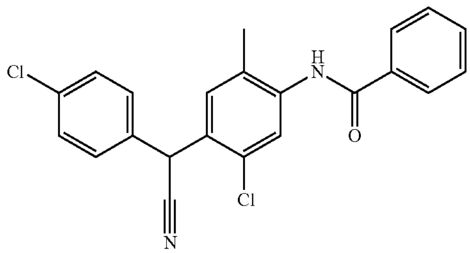
,
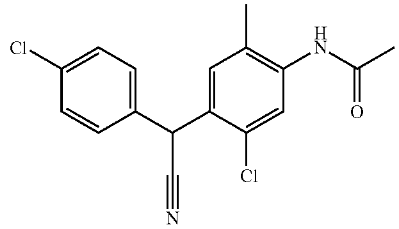
,
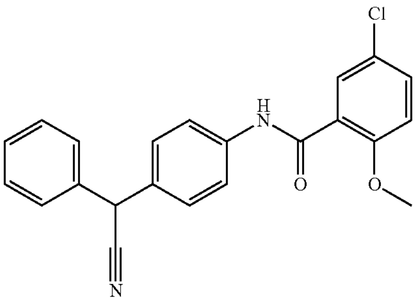
, -continued
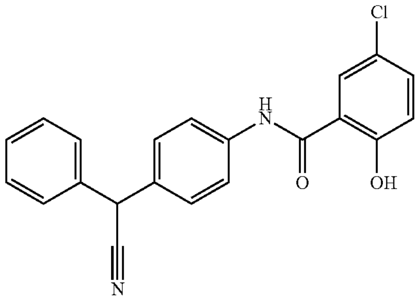
,
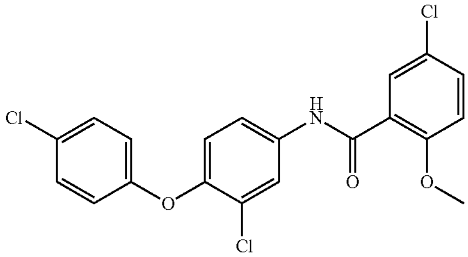
,
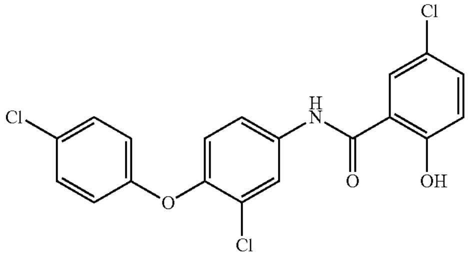
,
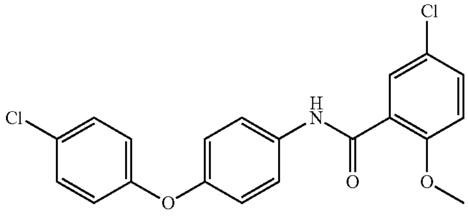
,
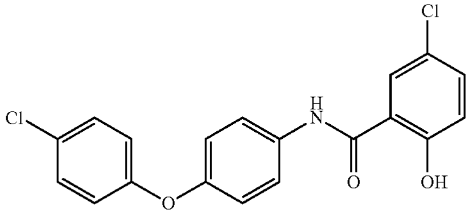
,
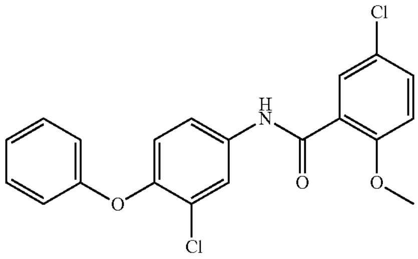
,
-continued
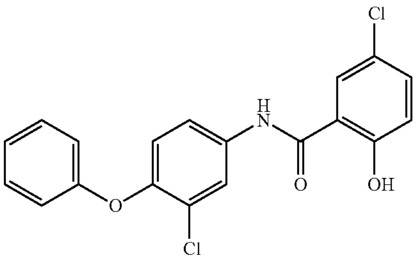
,
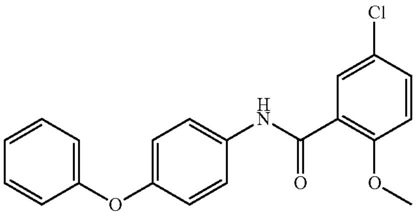
,
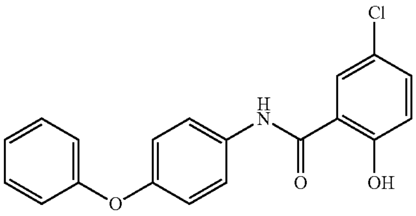
,
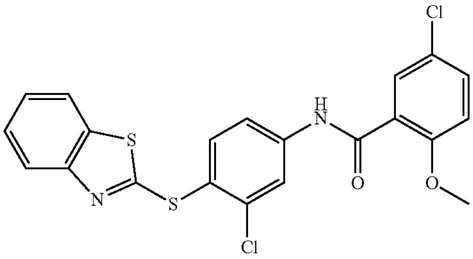
,
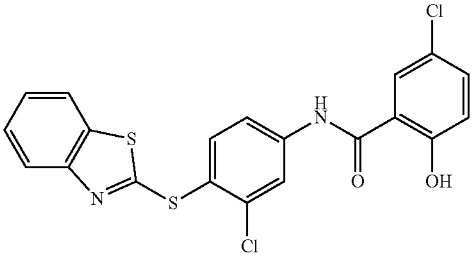
,
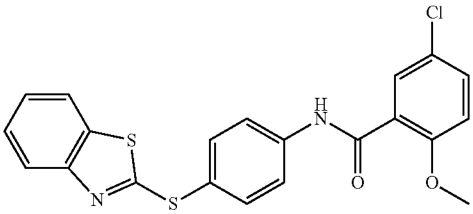
,
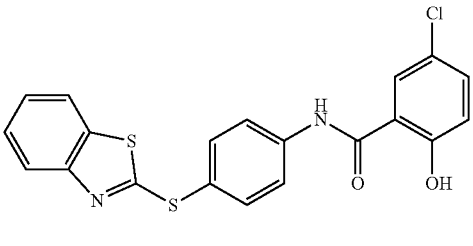
, -continued
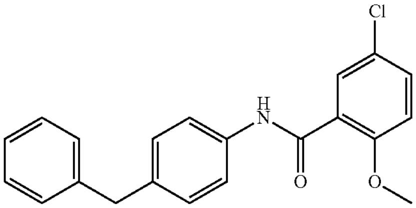
,
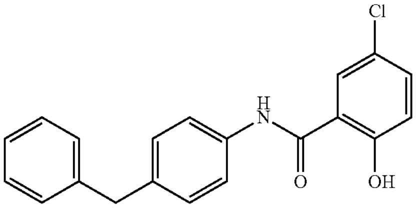
,
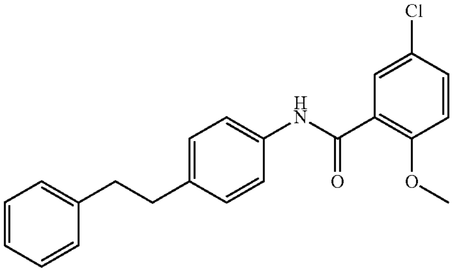
,
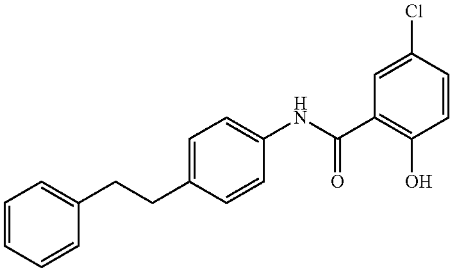
,
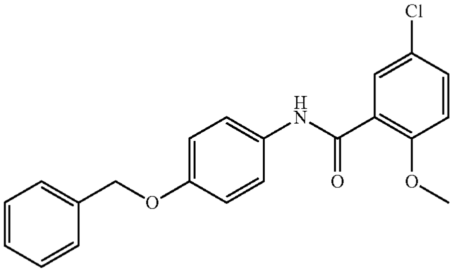
,
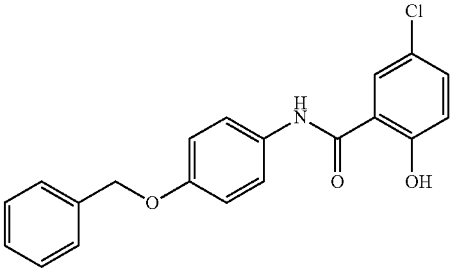
,
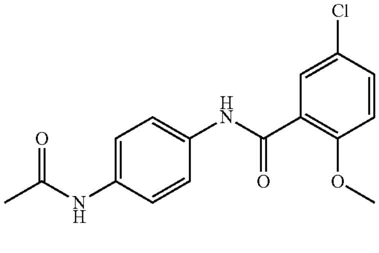
,
-continued
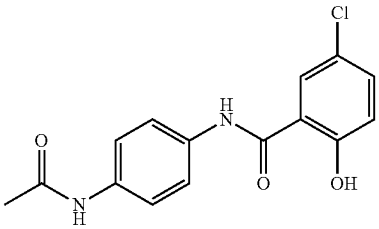
,
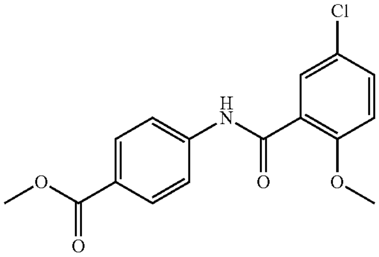
,
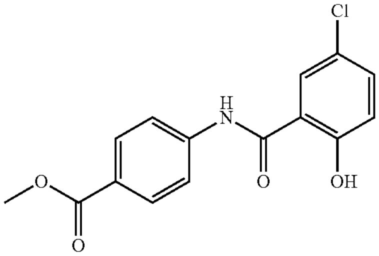
,
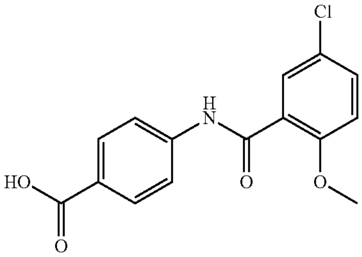
,
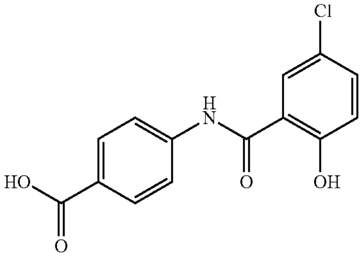
,
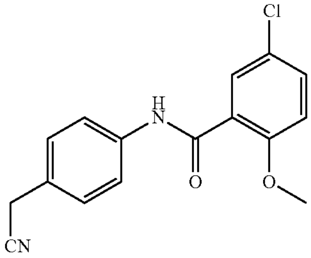
, -continued

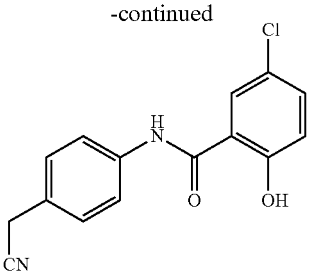

,

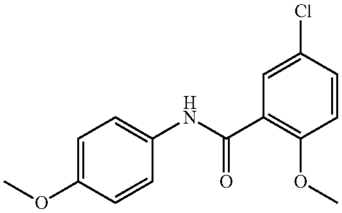

,

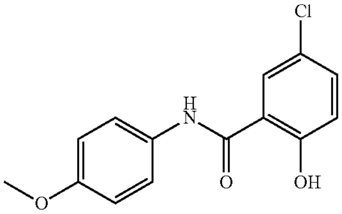

,

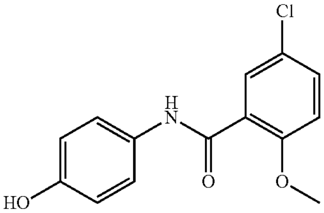

,

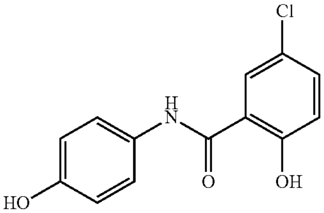

,

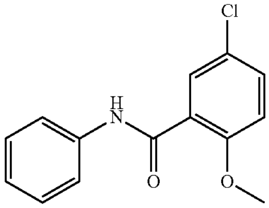

, and

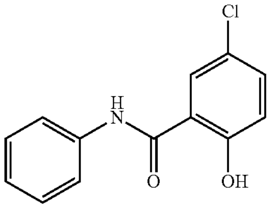

;

or a pharmaceutically acceptable salt thereof.

Clause 33. A method of killing bacteria in a biofilm comprising contacting the biofilm with a compound of any of the preceding clauses.

Clause 34. A method of preventing bacteria from forming a biofilm comprising contacting the bacteria with a compound of any of the preceding clauses.

Clause 35. The method of clauses 33 and 34, wherein the bacteria is from the genus *Staphylococcus*.

Those skilled in the art will recognize that the species listed or illustrated herein are not exhaustive, and that additional species within the scope of these defined terms may also be selected.

Chemical Synthesis

Exemplary chemical entities useful in methods of the description will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

Abbreviations: The examples described herein use materials, including but not limited to, those described by the following abbreviations known to those skilled in the art:

| | |
|---|---|
| g | grams |
| mmol | millimoles |
| mL | milliliters |
| EtOAc | ethyl acetate |
| MHz | megahertz |
| ppm | parts per million |
| δ | chemical shift |
| s | singlet |
| d | doublet |
| t | triplet |
| q | quartet |
| quin | quintet |
| br | broad |
| m | multiplet |
| Hz | hertz |
| THF | tetrahydrofuran |
| ° C. | degrees Celsius |
| Å | angstrom |
| EA | ethyl acetate |
| J | coupling constant |
| $d_6$-DMSO | deuterated dimethyl sulfoxide |
| min | minutes |
| hr (or h) | hours |
| Me | methyl |
| Et | ethyl |
| M | molar |
| MS | mass spectrometry |
| m/z | mass-to-charge ratio |
| TFA | trifluoroacetic acid |
| DMAP | 4-(dimethylamino)pyridine |
| μM | micromolar |
| ATP | adenosine triphosphate |
| DCM | dichloromethane |
| DMF | N,N-dimethylformamide |
| TEA | triethylamine |
| $CH_3CN$ | acetonitrile |
| MDH | malate dehydrogenase |
| R.T. | Room temperature |
| $IC_{50}$ | Inhibitory concentration for half-maximal signal in biochemical assay |
| $EC_{50}$ | Effective concentration for half-maximal signal in bacterial proliferation assays |
| $CC_{50}$ | Cytotoxicity concentration for half-maximal signal in human cell viability assays. |

Example 1

General Synthetic Method.

Unless otherwise stated, all chemicals were purchased from commercial suppliers and used without further purification. Reaction progress was monitored by thin-layer chromatography on silica gel 60 F254 coated glass plates (EM Sciences). Flash chromatography was performed using a Biotage Isolera One flash chromatography system and eluting through Biotage KP-Sil Zip or Snap silica gel columns for normal-phase separations (hexanes:EtOAc gradients), or Snap KP-C18-HS columns for reverse-phase separations ($H_2O$:MeOH gradients). Reverse-phase high-performance liquid chromatography (RP-HPLC) was performed using a Waters 1525 binary pump, 2489 tunable UV/Vis detector (254 and 280 nm detection), and 2707 autosampler. For preparatory HPLC purification, samples were chromatographically separated using a Waters XSelect CSH C18 OBD prep column (part number 186005422, 130 Å pore size, 5 μm particle size, 19×150 mm), eluting with a $H_2O$:$CH_3CN$ gradient solvent system. Linear gradients were run from either 100:0, 80:20, or 60:40 A:B to 0:100 A:B (A=95:5 $H_2O$:$CH_3CN$, 0.05% TFA; B=5:95 $H_2O$:$CH_3CN$, 0.05% TFA. Products from normal-phase separations were concentrated directly, and reverse-phase separations were concentrated, diluted with $H_2O$, frozen, and lyophilized. For primary compound purity analyses (HPLC-1), samples were chromatographically separated using a Waters XSelect CSH C18 column (part number 186005282, 130 Å pore size, 5 μm particle size, 3.0×150 mm), eluting with the above $H_2O$:$CH_3CN$ gradient solvent systems. For secondary purity analyses (HPLC-2) of final test compounds, samples were chromatographically separated using a Waters XBridge C18 column (either part number 186003027, 130 Å pore size, 3.5 μm particle size, 3.0×100 mm, or part number 186003132, 130 Å pore size, 5.0 μm particle size, 3.0×100 mm), eluting with a $H_2O$:MeOH gradient solvent system. Linear gradients were run from either 100:0, 80:20, 60:40, or 20:80 A:B to 0:100 A:B (A=95:5 $H_2O$:MeOH, 0.05% TFA; B=5:95 $H_2O$:MeOH, 0.05% TFA). Test compounds were found to be >95% in purity from both RP-HPLC analyses, with the exception of analogs 74 and, which were less pure in the HPLC-2 conditions (91% and 94% pure, respectively). Mass spectrometry data were collected using an Agilent analytical LC-MS at the IU Chemical Genomics Core Facility (CGCF). $^1$H-NMR spectra were recorded on a Bruker 300 MHz spectrometer in the CGCF. Chemical shifts are reported in parts per million and calibrated to the $d_6$-DMSO solvent peaks at 2.50 ppm. For the new analogs synthesized and evaluated in this study (45-117), the general protocols for the amide coupling, nitro-to-amine reduction, methoxy-to-hydroxy deprotection, and methyl ester-to-carboxyl deprotection reactions are presented below, with compound characterizations for each analog following.

Scheme 1.

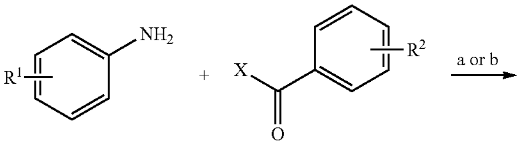

-continued

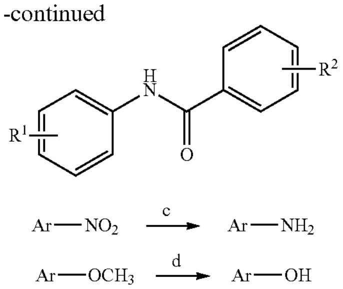

Reagents and conditions:
a) X = Cl: pyridine, $CH_2Cl_2$; b) X = OH: $SOCl_2$, 60° C., 1 h, then concentrate and add $CH_2Cl_2$, $R^1$-arylamine, and pyridine; c) Tin powder, 10% HCl/AcOH; d) $BBr_3$, $CH_2Cl_2$.

a) & b) General procedure for the amide coupling reactions. To stirring mixtures of the respective anilines (1 eq.) in anhydrous $CH_2Cl_2$ were added the respective $R^2$—COCl (1.2 eq.) reagents and pyridine (1.2 eq.). Note that for any analogs where the $R^2$—$CO_2H$ starting materials were only commercially available, the acids were first converted to the acid chlorides by stirring in thionyl chloride at for 1 h, then concentrating. The reactions were allowed to stir at room temperature for 18 h, then were either diluted with hexanes and the precipitates filtered, rinsed with water, collected, and purified by chromatography, or purified directly from the reactions. Flash chromatographic purification (either normal-phase with hexanes:EtOAc gradients, or reverse-phase with water:MeOH gradients) afforded the products as solids. If necessary, products were further purified by preparatory RP-HPLC (water:$CH_3CN$ gradients), concentrated, and lyophilized. Refer to the characterization data presented below for $^1$H-NMR, MS, and HPLC purity information for individual compounds.

c) General procedure for the nitro reduction reactions to give amine-bearing analogs 70-72. Tin powder (3 eq.) was added slowly to a stirring mixtures of 70-72 (1 eq.) in a 10% mixture of HCl in AcOH. The reactions were stirred for 2 h, then purified directly by reverse-phase chromatography (water:MeOH gradients). Product fractions were collected and lyophilized, then re-purified by preparatory RP-HPLC (water:$CH_3CN$ gradients), concentrated, and lyophilized. Refer to the characterization data presented below for $^1$H-NMR, MS, and HPLC purity information for individual compounds.

d) General procedure for the methoxy deprotection step to give hydroxylated analogs. To stirring mixtures of the respective methoxy analogs (1 eq.) in anhydrous $CH_2Cl_2$ was added $BBr_3$ (stock of 1 M in $CH_2Cl_2$, 3 eq.). The reactions were allowed to stir at R.T. (under Ar) for 18 h and then quenched with MeOH. Flash chromatographic purification (either normal-phase with hexanes:EtOAc gradients, or reverse-phase with water:MeOH gradients) afforded the products as solids. If necessary, products were further purified by preparatory RP-HPLC (water:$CH_3CN$ gradients), concentrated, and lyophilized. Refer to the characterization data presented below for $^1$H-NMR, MS, and HPLC purity information for individual compounds.

Example 2

Analog 45: 3,5-dibromo-N-(5-chloro-4-((4-chlorophenyl)(cyano)methyl)-2-methylphenyl)-2-methoxybenzamide. $^1$H-NMR (300 MHz, $d_6$-DMSO) δ10.14 (s, 1H), 8.07 (d, J=2.4 Hz, 1H), 7.84 (d, J=2.3 Hz, 1H), 7.83 (s, 1H), 7.47-7.53 (m, 3H), 7.37-7.43 (m, 2H), 6.03 (s, 1H), 3.85 (s, 3H), 2.32 (s, 3H); MS (ESI) $C_{23}H_{15}Br_2Cl_2N_2O_2$ [M-H]$^-$ m/z expected=580.9, observed=580.7; HPLC-1=>99%; HPLC-2=>99%.

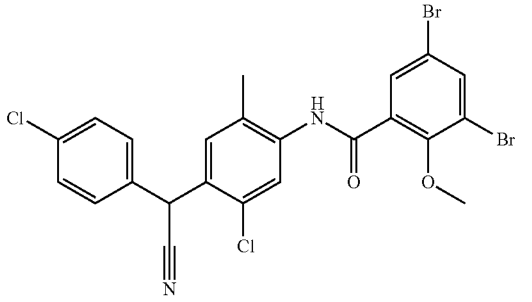 [SMILES: COc1c(Br)cc(Br)cc1C(=O)Nc1cc(Cl)c(C(C#N)c2ccc(Cl)cc2)cc1C]

Example 3

Analog 46: 3,5-dibromo-N-(5-chloro-4-((4-chlorophenyl)(cyano)methyl)-2-methylphenyl)-2-hydroxybenzamide. $^1$H-NMR (300 MHz, $d_6$-DMSO) δ10.71 (s, 1H), 8.23 (d, J=2.2 Hz, 1H), 8.04 (d, J=2.1 Hz, 1H), 7.89 (s, 1H), 7.56 (s, 1H), 7.48-7.54 (m, 2H), 7.37-7.44 (m, 2H), 6.05 (s, 1H), 2.28 (s, 3H); MS (ESI) $C_{22}H_{13}Br_2Cl_2N_2O_2$ [M-H]$^-$ m/z expected=566.9, observed=566.7; HPLC-1=99%; HPLC-2=99%.

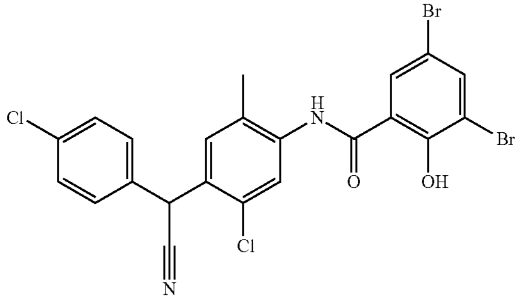 [SMILES: Cc1cc(C(C#N)c2ccc(Cl)cc2)c(Cl)cc1NC(=O)c1cc(Br)cc(Br)c1O]

Example 4

Analog 47: 3-bromo-N-(5-chloro-4-((4-chlorophenyl)(cyano)methyl)-2-methylphenyl)-2-methoxybenzamide. $^1$H-NMR (300 MHz, $d_6$-DMSO) δ10.07 (s, 1H), 7.89 (s, 1H), 7.82 (dd, J=8.0, 1.5 Hz, 1H), 7.68 (dd, J=7.7, 1.4 Hz, 1H), 7.47-7.54 (m, 3H), 7.37-7.43 (m, 2H), 7.23 (t, J=7.8 Hz, 1H), 6.03 (s, 1H), 3.86 (s, 3H), 2.34 (s, 3H); MS (ESI) $C_{23}H_{16}BrCl_2N_2O_2$ [M-H]$^-$ m/z expected=503.0, observed=502.9; HPLC-1=98%; HPLC-2=98%.

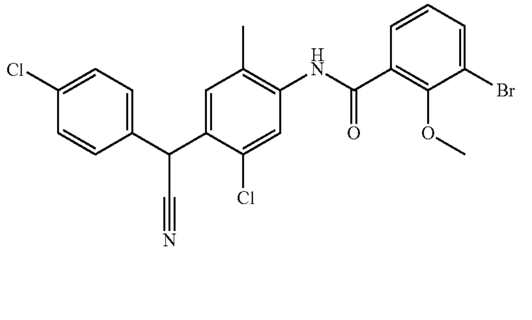 [SMILES: COc1c(Br)cccc1C(=O)Nc1cc(Cl)c(C(C#N)c2ccc(Cl)cc2)cc1C]

Example 5

Analog 48: 3-bromo-N-(5-chloro-4-((4-chlorophenyl)(cyano)methyl)-2-methylphenyl)-2-hydroxybenzamide. $^1$H-NMR (300 MHz, $d_6$-DMSO) δ12.75 (br s, 1H), 10.58 (s, 1H), 7.94-8.01 (m, 1H), 7.75 (dd, J=7.8, 1.2 Hz, 1H), 7.64 (s, 1H), 7.50 (s, 1H), 7.41-7.48 (m, 2H), 7.31-7.39 (m, 2H), 6.89 (t, J=7.9 Hz, 1H), (s, 1H), 2.22 (s, 3H); MS (ESI) $C_{22}H_{14}BrCl_2N_2O_2$ [M-H]$^-$ m/z expected=489.0, observed=488.8; HPLC-1=>99%; HPLC-2=>99%.

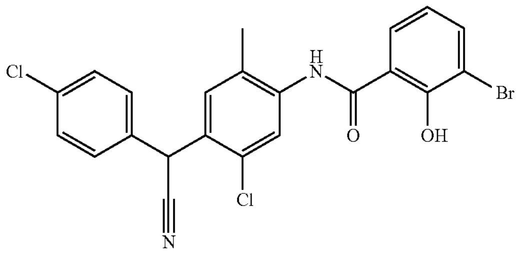 [SMILES: Cc1cc(C(C#N)c2ccc(Cl)cc2)c(Cl)cc1NC(=O)c1cccc(Br)c1O]

Example 6

Analog 49: 5-bromo-N-(5-chloro-4-((4-chlorophenyl)(cyano)methyl)-2-methylphenyl)-2-methoxybenzamide. $^1$H-NMR (300 MHz, $d_6$-DMSO) δ9.99 (s, 1H), 8.14 (s, 1H), 7.96 (d, J=2.4 Hz, 1H), 7.74 (dd, J=8.8, 2.4 Hz, 1H), 7.47-7.53 (m, 3H), 7.35-7.43 (m, 2H), 7.24 (d, J=8.8 Hz, 1H), 6.02 (s, 1H), 3.98 (s, 3H), 2.34 (s, 3H); MS (ESI) $C_{23}H_{16}BrCl_2N_2O_2$ [M-H]$^-$ m/z expected=503.0, observed=502.8; HPLC-1=97%; HPLC-2=97%.

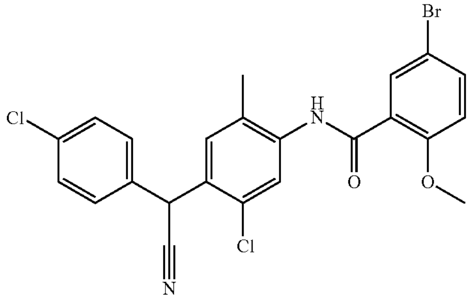 [SMILES: COc1ccc(Br)cc1C(=O)Nc1cc(Cl)c(C(C#N)c2ccc(Cl)cc2)cc1C]

Example 7

Analog 50: 5-bromo-N-(5-chloro-4-((4-chlorophenyl)(cyano)methyl)-2-methylphenyl)-2-hydroxybenzamide. $^1$H-NMR (300 MHz, $d_6$-DMSO) δ12.22 (s, 1H), 10.46 (s, 1H), 8.27 (s, 1H), 8.07 (d, J=2.6 Hz, 1H), 7.61 (dd, J=8.8, 2.6 Hz, 1H), 7.46-7.54 (m, 3H), 7.36-7.42 (m, 2H), 7.01 (d, J=8.8 Hz, 1H), 6.02 (s, 1H), 2.33 (s, 3H); MS (ESI) $C_{22}H_{14}BrCl_2N_2O_2$ [M-H]$^-$ m/z expected=489.0, observed=488.89; HPLC-1=>99%; HPLC-2=>99%.

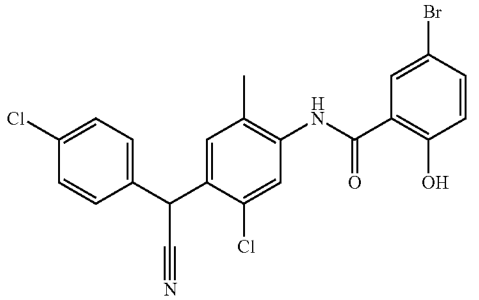

Example 8

Analog 51: 3,5-dichloro-N-(5-chloro-4-((4-chlorophenyl)(cyano)methyl)-2-methylphenyl)-2-methoxybenzamide. $^1$H-NMR (300 MHz, $d_6$-DMSO) δ10.13 (s, 1H), 7.86 (d, J=2.6 Hz, 1H), 7.84 (s, 1H), 7.71 (d, J=2.6 Hz, 1H), 7.47-7.53 (m, 3H), 7.37-7.43 (m, 2H), 6.03 (s, 1H), 3.87 (s, 3H), 2.32 (s, 3H); MS (ESI) $C_{23}H_{15}Cl_4N_2O_2$ [M-H]$^-$ m/z expected=493.0, observed=492.9; HPLC-1=96%; HPLC-2=98%.

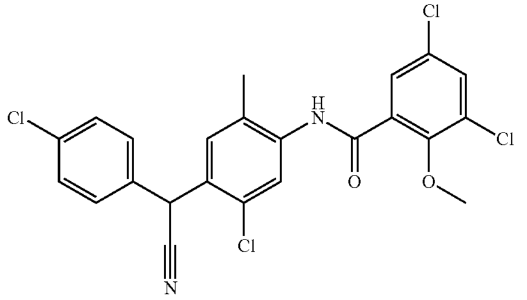 [SMILES: COc1c(Cl)cc(Cl)cc1C(=O)Nc1cc(Cl)c(C(C#N)c2ccc(Cl)cc2)cc1C]

Example 9

Analog 52: 3,5-dichloro-N-(5-chloro-4-((4-chlorophenyl)(cyano)methyl)-2-methylphenyl)-2-hydroxybenzamide. $^1$H-NMR (300 MHz, $d_6$-DMSO) δ10.68 (s, 1H), 7.98 (d, J=2.5 Hz, 1H), 7.77 (d, J=2.5 Hz, 1H), 7.72 (s, 1H), 7.49 (s, 1H), 7.41-7.48 (m, 2H), 7.30-7.38 (m, 2H), 5.98 (s, 1H), 2.23 (s, 3H); MS (ESI) $C_{22}H_{13}Cl_4N_2O_2$ [M-H]$^-$ m/z expected=479.0, observed=478.9; HPLC-1=>99%; HPLC-2=99%.

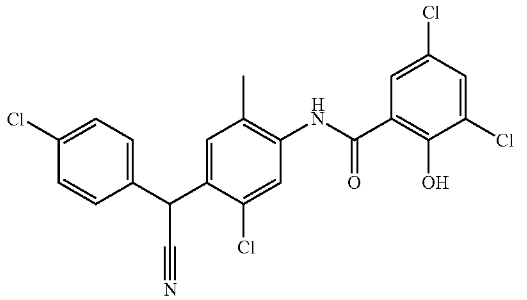 [SMILES: Cc1cc(C(C#N)c2ccc(Cl)cc2)c(Cl)cc1NC(=O)c1cc(Cl)cc(Cl)c1O]

Example 10

Analog 53: 3-chloro-N-(5-chloro-4-((4-chlorophenyl)(cyano)methyl)-2-methylphenyl)-2-methoxybenzamide. $^1$H-NMR (300 MHz, $d_6$-DMSO) δ10.07 (s, 1H), 7.90 (s, 1H), 7.67 (td, J=7.9, 1.5 Hz, 2H), 7.47-7.54 (m, 3H), 7.37-7.43 (m, 2H), 7.30 (t, J=7.8 Hz, 1H), 6.03 (s, 1H), 3.88 (s, 3H), 2.34 (s, 3H); MS (ESI) $C_{23}H_{16}Cl_3N_2O_2$ [M-H]$^-$ m/z expected=457.0, observed=456.9; HPLC-1=98%; HPLC-2=>99%.

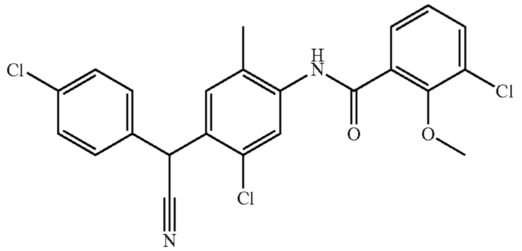

Example 11

Analog 54: 3-chloro-N-(5-chloro-4-((4-chlorophenyl)(cyano)methyl)-2-methylphenyl)-2-hydroxybenzamide. $^1$H-NMR (300 MHz, $d_6$-DMSO) δ12.83 (br s, 1H), 10.65 (s, 1H), 7.99 (dd, J=8.1, 1.4 Hz, 1H), 7.77 (s, 1H), 7.67 (dd, J=7.8, 1.4 Hz, 1H), 7.56 (s, 1H), 7.48-7.54 (m, 2H), 7.37-7.44 (m, 2H), 7.01 (t, J=8.0 Hz, 1H), 6.05 (s, 1H), 2.29 (s, 3H); MS (ESI) $C_{22}H_{14}Cl_3N_2O_2$ [M-H]$^-$ m/z expected=443.0, observed=442.9; HPLC-1=>99%; HPLC-2=99%.

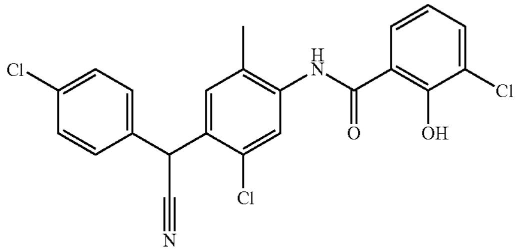 [SMILES: Cc1cc(C(C#N)c2ccc(Cl)cc2)c(Cl)cc1NC(=O)c1cccc(Cl)c1O]

Example 12

Analog 55: 4-chloro-N-(5-chloro-4-((4-chlorophenyl)(cyano)methyl)-2-methylphenyl)-2-methoxybenzamide. $^1$H-NMR (300 MHz, $d_6$-DMSO) δ9.92 (s, 1H), 8.19 (s, 1H), 7.90 (d, J=8.3 Hz, 1H), 7.46-7.53 (m, 3H), 7.34-7.42 (m, 3H), 7.19 (dd, J=8.4, 1.9 Hz, 1H), 6.01 (s, 1H), 4.02 (s, 3H), 2.34 (s, 3H); MS (ESI) $C_{23}H_{16}Cl_3N_2O_2$ [M-H]$^-$ m/z expected=457.0, observed=456.9; HPLC-1=98%; HPLC-2=>99%.

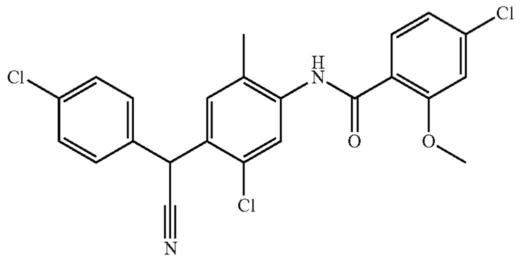 [SMILES: COc1cc(Cl)ccc1C(=O)Nc1cc(Cl)c(C(C#N)c2ccc(Cl)cc2)cc1C]

Example 13

Analog 56: 4-chloro-N-(5-chloro-4-((4-chlorophenyl)(cyano)methyl)-2-methylphenyl)-2-hydroxybenzamide. $^1$H-NMR (300 MHz, $d_6$-DMSO) δ12.42 (br s, 1H), 10.42 (s, 1H), 8.29 (s, 1H), 7.99 (d, J=9.1 Hz, 1H), 7.45-7.56 (m, 3H), 7.34-7.43 (m, 2H), 7.03-7.11 (m, 2H), 6.02 (s, 1H), 2.33 (s, 3H); MS (ESI) $C_{22}H_{14}Cl_3N_2O_2$ $[M-H]^-$ m/z expected=443.0, observed=442.9; HPLC-1=>99%; HPLC-2=>99%.

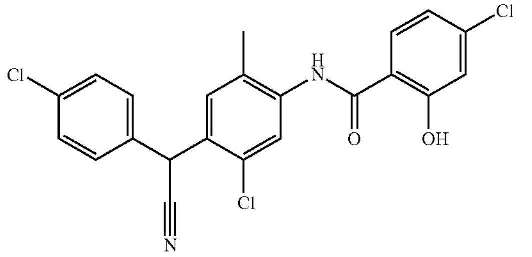 [SMILES: Cc1cc(C(C#N)c2ccc(Cl)cc2)c(Cl)cc1NC(=O)c1ccc(Cl)cc1O]

Example 14

Analog 57: 5-chloro-N-(5-chloro-4-((4-chlorophenyl)(cyano)methyl)-2-methylphenyl)-2-methoxybenzamide. $^1$H-NMR (300 MHz, $d_6$-DMSO) δ9.94 (s, 1H), 8.08 (s, 1H), 7.78 (d, J=2.7 Hz, 1H), 7.57 (dd, J=8.9, 2.7 Hz, 1H), 7.41-7.47 (m, 3H), 7.30-7.36 (m, 2H), 7.24 (d, J=8.9 Hz, 1H), 5.96 (s, 1H), 3.93 (s, 3H), 2.28 (s, 3H); MS (ESI) $C_{23}H_{16}Cl_3N_2O_2$ $[M-H]^-$ m/z expected=457.0, observed=456.9; HPLC-1=98%; HPLC-2=>99%.

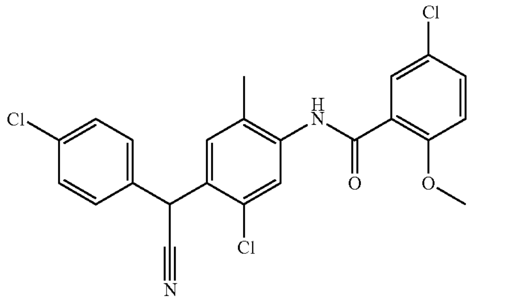

Example 15

Analog 58: 5-chloro-N-(5-chloro-4-((4-chlorophenyl)(cyano)methyl)-2-methylphenyl)-2-hydroxybenzamide. $^1$H-NMR (300 MHz, $d_6$-DMSO) δ10.55 (s, 1H), 8.28 (s, 1H), 7.95 (d, J=2.8 Hz, 1H), 7.46-7.54 (m, 4H), 7.36-7.42 (m, 2H), 7.06 (d, J=8.8 Hz, 1H), 6.02 (s, 1H), 2.33 (s, 3H); MS (ESI) $C_{22}H_{14}Cl_3N_2O_2$ $[M-H]^-$ m/z expected=443.0, observed=442.9; HPLC-1=>99%; HPLC-2=>99%.

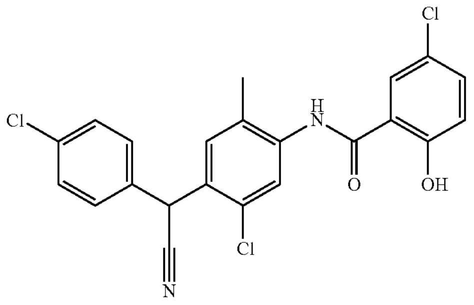

Example 16

Analog 59: N-(5-chloro-4-((4-chlorophenyl)(cyano)methyl)-2-methylphenyl)-2-methoxy-5-methylbenzamide. $^1$H-NMR (300 MHz, $d_6$-DMSO) δ10.06 (s, 1H), 8.28 (s, 1H), 7.76 (d, J=2.0 Hz, 1H), 7.46-7.54 (m, 3H), 7.36-7.42 (m, 3H), 7.16 (d, J=8.5 Hz, 1H), 6.01 (s, 1H), 3.99 (s, 3H), 2.36 (s, 3H), 2.31 (s, 3H); MS (ESI) $C_{24}H_{19}Cl_3N_2O_2$ $[M-H]^-$ m/z expected=437.1, observed=437.0; HPLC-1=98%; HPLC-2=>99%.

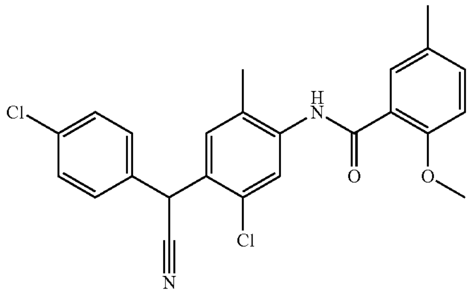 [SMILES: COc1ccc(C)cc1C(=O)Nc1cc(Cl)c(C(C#N)c2ccc(Cl)cc2)cc1C]

Example 17

Analog 60: N-(5-chloro-4-((4-chlorophenyl)(cyano)methyl)-2-methylphenyl)-2-hydroxy-5-methylbenzamide. $^1$H-NMR (300 MHz, $d_6$-DMSO) δ11.71 (s, 1H), 10.52 (s, 1H), 8.33 (s, 1H), 7.81 (d, J=1.9 Hz, 1H), 7.47-7.54 (m, 3H), 7.36-7.42 (m, 2H), 7.26 (dd, J=8.5, 2.0 Hz, 1H), 6.93 (d, J=8.3 Hz, 1H), 6.01 (s, 1H), 2.33 (s, 3H), 2.27 (s, 3H); MS (ESI) $C_{23}H_{17}Cl_2N_2O_2$ $[M-H]^-$ m/z expected=423.1, observed=423.0; HPLC-1=>99%; HPLC-2=>99%.

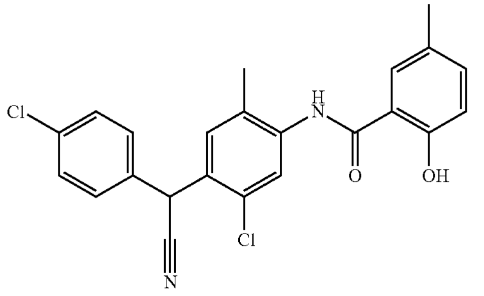 [SMILES: Cc1ccc(O)c(C(=O)Nc2cc(Cl)c(C(C#N)c3ccc(Cl)cc3)cc2C)c1]

Example 18

Analog 61: N-(5-chloro-4-((4-chlorophenyl)(cyano)methyl)-2-methylphenyl)-2-methoxybenzamide. $^1$H-NMR (300 MHz, $d_6$-DMSO) δ10.04 (s, 1H), 8.27 (s, 1H), 7.94 (dd, J=7.7, 1.7 Hz, 1H), 7.55-7.63 (m, 1H), 7.47-7.53 (m, 3H), 7.36-7.43 (m, 2H), 7.27 (d, J=8.3 Hz, 1H), 7.10-7.17 (m, 1H), 6.01 (s, 1H), 4.01 (s, 3H), 2.36 (s, 3H); MS (ESI) $C_{23}H_{17}Cl_2N_2O_2$ $[M-H]^-$ m/z expected=423.1, observed=423.0; HPLC-1=996%; HPLC-2=99%.

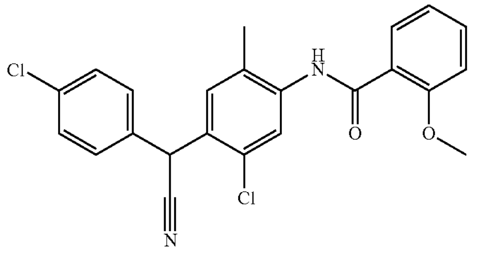 [SMILES: COc1ccccc1C(=O)Nc1cc(Cl)c(C(C#N)c2ccc(Cl)cc2)cc1C]

Example 19

Analog 62: N-(5-chloro-4-((4-chlorophenyl)(cyano)methyl)-2-methylphenyl)-3-methoxybenzamide. $^1$H-NMR (300 MHz, $d_6$-DMSO) δ9.98 (s, 1H), 7.61 (s, 1H), 7.44-7.57 (m, 6H), 7.37-7.44 (m, 2H), 7.18 (ddd, J=8.1, 2.6, Hz, 1H), 6.04 (s, 1H), 3.83 (s, 3H), 2.28 (s, 3H); MS (ESI) $C_{23}H_{17}Cl_2N_2O_2$ $[M-H]^-$ m/z expected=423.1, observed=423.0; HPLC-1=98%; HPLC-2=98%.

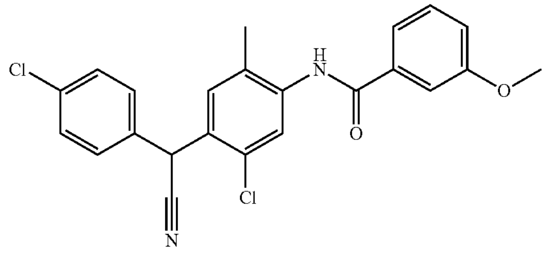 [SMILES: COc1cccc(C(=O)Nc2cc(Cl)c(C(C#N)c3ccc(Cl)cc3)cc2C)c1]

Example 20

Analog 63: N-(5-chloro-4-((4-chlorophenyl)(cyano)methyl)-2-methylphenyl)-4-methoxybenzamide. $^1$H-NMR (300 MHz, $d_6$-DMSO) δ9.83 (s, 1H), 7.92-7.98 (m, 2H), 7.61 (s, 1H), 7.48-7.54 (m, 3H), 7.37-7.43 (m, 2H), 7.04-7.10 (m, 2H), 6.03 (s, 1H), 3.84 (s, 3H), 2.28 (s, 3H); MS (ESI) $C_{23}H_{17}Cl_2N_2O_2$ $[M-H]^-$ m/z expected=423.1, observed=423.0; HPLC-1=>99%; HPLC-2=>99%.

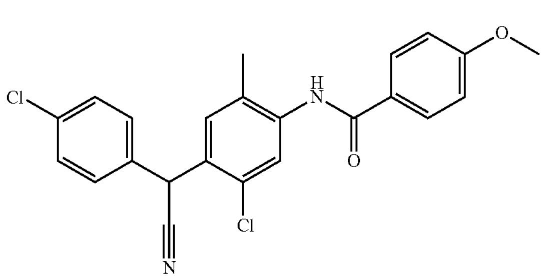 [SMILES: COc1ccc(C(=O)Nc2cc(Cl)c(C(C#N)c3ccc(Cl)cc3)cc2C)cc1]

Example 21

Analog 64: N-(5-chloro-4-((4-chlorophenyl)(cyano)methyl)-2-methylphenyl)-2-hydroxybenzamide. $^1$H-NMR (300 MHz, $d_6$-DMSO) δ11.97 (br s, 1H), 10.56 (s, 1H), 8.32 (s, 1H), 8.00 (dd, J=7.9, 1.7 Hz, 1H), 7.36-7.54 (m, 6H), 6.96-7.06 (m, 2H), 6.02 (s, 1H), 2.34 (s, 3H); MS (ESI) $C_{22}H_{15}Cl_2N_2O_2$ $[M-H]^-$ m/z expected=409.1, observed=409.0; HPLC-1=>99%; HPLC-2=>99%.

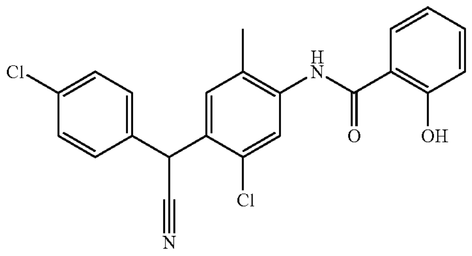

Example 22

Analog 65: N-(5-chloro-4-((4-chlorophenyl)(cyano)methyl)-2-methylphenyl)-3-hydroxybenzamide. $^1$H-NMR (300 MHz, $d_6$-DMSO) δ9.89 (s, 1H), 9.79 (s, 1H), 7.61 (s, 1H), 7.48-7.54 (m, 3H), 7.36-7.54 (m, 3H), 7.29-7.36 (m, 2H), 6.99 (ddd, J=7.8, 2.4, 1.2 Hz, 1H), 6.03 (s, 1H), 2.28 (s, 3H); MS (ESI) $C_{22}H_{15}Cl_2N_2O_2$ $[M-H]^-$ m/z expected=409.1, observed=408.9; HPLC-1=>99%; HPLC-2=>99%.

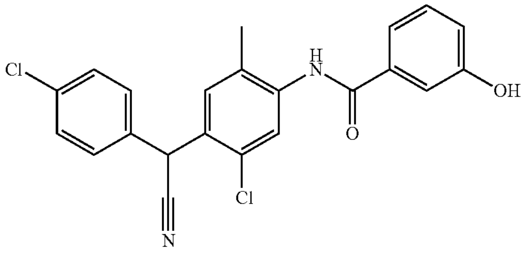 [SMILES: Cc1cc(C(C#N)c2ccc(Cl)cc2)c(Cl)cc1NC(=O)c1cccc(O)c1]

Example 23

Analog 66: N-(5-chloro-4-((4-chlorophenyl)(cyano)methyl)-2-methylphenyl)-4-hydroxybenzamide. $^1$H-NMR (300 MHz, $d_6$-DMSO) δ10.15 (s, 1H), 9.71 (s, 1H), 7.81-7.88 (m, 2H), 7.61 (s, 1H), 7.47-7.54 (m, 3H), 7.37-7.43 (m, 2H), 6.83-6.91 (m, 2H), 6.02 (s, 1H), 2.27 (s, 3H); MS (ESI) $C_{22}H_{15}Cl_2N_2O_2$ $[M-H]^-$ m/z expected=409.1, observed=409.0; HPLC-1=96%; HPLC-2=95%.

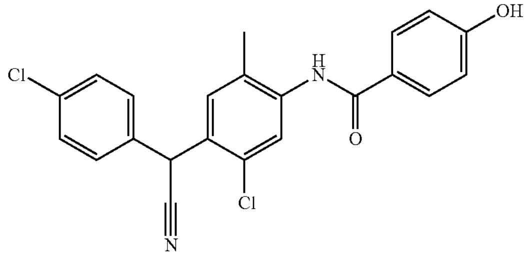 [SMILES: Cc1cc(C(C#N)c2ccc(Cl)cc2)c(Cl)cc1NC(=O)c1ccc(O)cc1]

Example 24

Analog 67: N-(5-chloro-4-((4-chlorophenyl)(cyano)methyl)-2-methylphenyl)-2-nitrobenzamide. $^1$H-NMR (300 MHz, $d_6$-DMSO) δ10.39 (s, 1H), 8.15-8.21 (m, 1H), 7.72-7.94 (m, 4H), 7.47-7.55 (m, 3H), 7.37-7.44 (m, 2H), 6.04 (s, 1H), 2.30 (s, 3H); MS (ESI) $C_{22}H_{14}Cl_2N_2O_2$ $[M-H]^-$ m/z expected=438.0, observed=438.0.6; HPLC-1=95%; HPLC-2=99%.

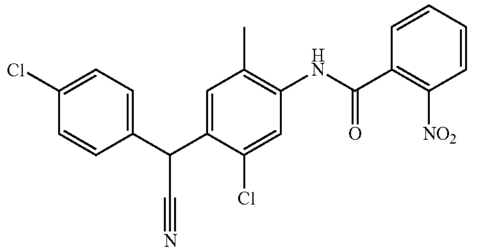 [SMILES: Cc1cc(C(C#N)c2ccc(Cl)cc2)c(Cl)cc1NC(=O)c1ccccc1[N+](=O)[O-]]

Example 25

Analog 68: N-(5-chloro-4-((4-chlorophenyl)(cyano)methyl)-2-methylphenyl)-3-nitrobenzamide. $^1$H-NMR (300 MHz, $d_6$-DMSO) δ10.39 (s, 1H), 8.78 (t, J=1.9 Hz, 1H), 8.43-8.50 (m, 1H), 8.36-8.53 (m, 1H), 7.86 (t, J=8.0 Hz, 1H), 7.63 (s, 1H), 7.48-7.57 (m, 3H), 7.38-7.45 (m, 2H), 6.05 (s, 1H), 2.30 (s, 3H); MS (ESI) $C_{22}H_{14}Cl_2N_2O_2$ $[M-H]^-$ m/z expected=438.0, observed=438.0; HPLC-1=97%; HPLC-2=99%.

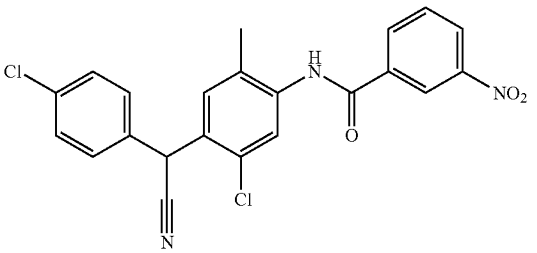 [SMILES: Cc1cc(C(C#N)c2ccc(Cl)cc2)c(Cl)cc1NC(=O)c1cccc([N+](=O)[O-])c1]

Example 26

Analog 69: N-(5-chloro-4-((4-chlorophenyl)(cyano)methyl)-2-methylphenyl)-4-nitrobenzamide. $^1$H-NMR (300 MHz, $d_6$-DMSO) δ10.34 (s, 1H), 8.35-8.42 (m, 2H), 8.15-8.23 (m, 2H), 7.94 (s, 1H), 7.48-7.56 (m, 3H), 7.38-7.44 (m, 2H), 6.05 (s, 1H), 2.30 (s, 3H); MS (ESI) $C_{22}H_{14}Cl_2N_3O_3$ $[M-H]^-$ m/z expected=438.0, observed=438.0; HPLC-1=98%; HPLC-2=98%.

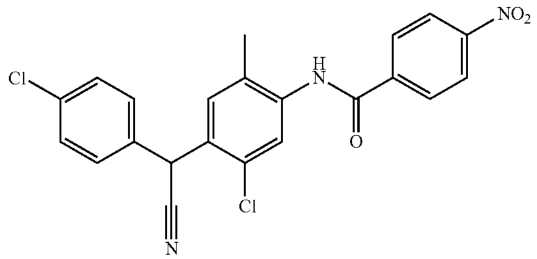

Example 27

Analog 70: 2-amino-N-(5-chloro-4-((4-chlorophenyl)(cyano)methyl)-2-methylphenyl)benzamide. $^1$H-NMR (300 MHz, $d_6$-DMSO) δ9.73 (s, 1H), 7.67 (dd, J=8.0, 1.2 Hz, 1H), 7.60 (s, 1H), 7.47-7.55 (m, 3H), 7.36-7.44 (m, 2H), 7.17-7.26 (m, 1H), 6.73-6.80 (m, 1H), 6.55-6.64 (m, 1H), 6.37 (br s, 2H), 6.03 (s, 1H), 2.27 (s, 3H); MS (ESI) $C_{22}H_{16}Cl_2N_3O$ $[M-H]^-$ m/z expected=408.1, observed=408.0; HPLC-1=>99%; HPLC-2=>99%

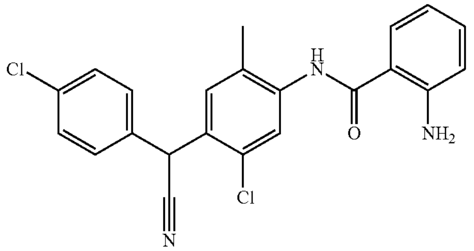

Example 28

Analog 71: 3-amino-N-(5-chloro-4-((4-chlorophenyl)(cyano)methyl)-2-methylphenyl)benzamide. $^1$H-NMR (300 MHz, $d_6$-DMSO) δ9.85 (s, 1H), 7.54 (s, 1H), 7.41-7.48 (m, 3H), 7.29-7.37 (m, 4H), 7.22-7.29 (m, 1H), 6.93-7.00 (s, 1H), 6.25 (br s, 2H), 5.97 (s, 1H), 2.21 (s, 3H); MS (ESI) $C_{22}H_{16}Cl_2N_3O$ $[M-H]^-$ m/z expected=408.1, observed=408.0; HPLC-1=>99%; HPLC-2=>99%.

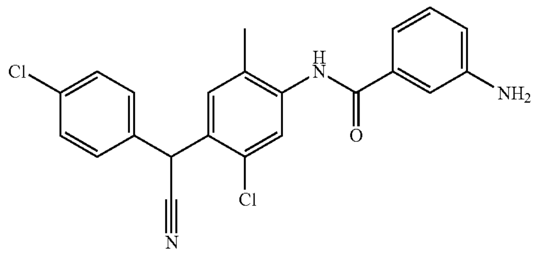

Example 29

Analog 72: 4-amino-N-(5-chloro-4-((4-chlorophenyl)(cyano)methyl)-2-methylphenyl)benzamide. $^1$H-NMR (300 MHz, $d_6$-DMSO) δ9.19 (s, 1H), 7.41-7.48 (m, 2H), 7.37 (s, 1H), 7.20-7.28 (m, 3H), 7.10-7.18 (m, 2H), 6.31-6.39 (m, 2H), 5.78 (s, 1H), 5.54 (br s, 2H), 2.01 (s, 3H); MS (ESI) $C_{22}H_{16}Cl_2N_3O$ $[M-H]^-$ m/z expected=408.1, observed=408.0; HPLC-1=95%; HPLC-2=96%.

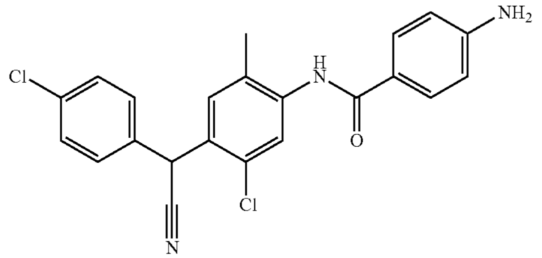

Example 30

Analog 73: 2-bromo-N-(5-chloro-4-((4-chlorophenyl)(cyano)methyl)-2-methylphenyl)benzamide. $^1$H-NMR (300 MHz, $d_6$-DMSO) δ10.18 (s, 1H), 7.69-7.76 (m, 2H), 7.61 (dd, J=7.4, 1.5 Hz, 1H), 7.47-7.55 (m, 4H), 7.37-7.47 (m, 3H), 6.04 (s, 1H), 2.33 (s, 3H); MS (ESI) $C_{22}H_{14}Cl_2N_2O$ $[M-H]^-$ m/z expected=473.0, observed=472.9; HPLC-1=>99%; HPLC-2=>99%.

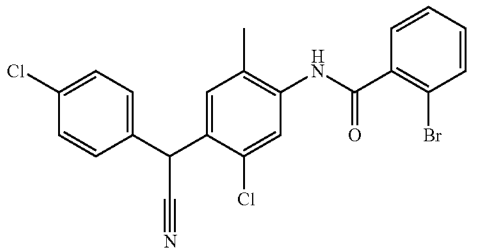

Example 31

Analog 74: 3-bromo-N-(5-chloro-4-((4-chlorophenyl)(cyano)methyl)-2-methylphenyl)benzamide. $^1$H-NMR (300 MHz, $d_6$-DMSO) δ10.13 (s, 1H), 8.13 (t, J=1.7 Hz, 1H), 7.93-7.97 (m, 1H), 7.82 (ddd, J=8.0, 1.9, 0.9 Hz, 1H), 7.60 (s, 1H), 7.48-7.55 (m, 4H), 7.38-7.44 (m, 2H), 6.04 (s, 1H), 2.28 (s, 3H); MS (ESI) $C_{22}H_{14}Cl_2N_2O$ $[M-H]^-$ m/z expected=473.0, observed=472.8; HPLC-1=>99%; HPLC-2=91%.

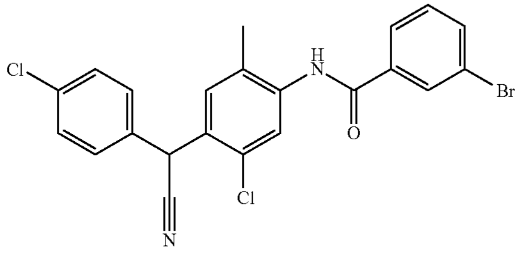 [SMILES: Cc1cc(C(C#N)c2ccc(Cl)cc2)c(Cl)cc1NC(=O)c1cccc(Br)c1]

Example 32

Analog 75: 4-bromo-N-(5-chloro-4-((4-chlorophenyl)(cyano)methyl)-2-methylphenyl)benzamide. $^1$H-NMR (300 MHz, $d_6$-DMSO) δ10.08 (s, 1H), 7.88-7.94 (m, 2H), 7.73-7.79 (m, 2H), 7.61 (s, 1H), 7.48-7.54 (m, 3H), 7.37-7.43 (m, 2H), 6.04 (s, 1H), 2.28 (s, 3H); MS (ESI) $C_{22}H_{14}Cl_2N_2O$ $[M-H]^-$ m/z expected=473.0, observed=472.9; HPLC-1=>99%; HPLC-2=>99%.

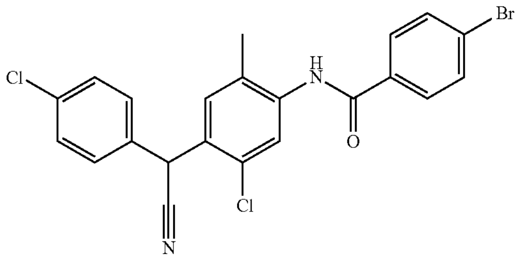 [SMILES: Cc1cc(C(C#N)c2ccc(Cl)cc2)c(Cl)cc1NC(=O)c1ccc(Br)cc1]

Example 33

Analog 76: 2-chloro-N-(5-chloro-4-((4-chlorophenyl)(cyano)methyl)-2-methylphenyl)benzamide. $^1$H-NMR (300 MHz, $d_6$-DMSO) δ10.19 (s, 1H), 7.72 (s, 1H), 7.64 (dd, J=7.2, 1.8 Hz, 1H), 7.55-7.61 (m, 1H), 7.43-7.55 (m, 5H), 7.36-7.43 (m, 2H), 6.04 (s, 1H), 2.32 (s, 3H); MS (ESI) $C_{22}H_{14}Cl_3N_2O$ $[M-H]^-$ m/z expected=427.0, observed=427.0; HPLC-1=98%; HPLC-2=>99%.

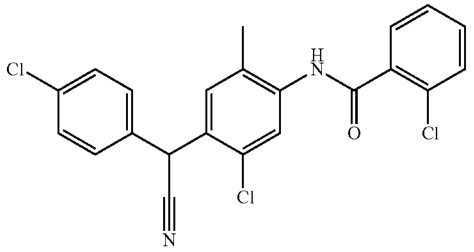

Example 34

Analog 77: 3-chloro-N-(5-chloro-4-((4-chlorophenyl)(cyano)methyl)-2-methylphenyl)benzamide. $^1$H-NMR (300 MHz, $d_6$-DMSO) δ10.13 (s, 1H), 8.00 (t, J=1.7 Hz, 1H), 7.91 (dt, J=7.8, 1.3 Hz, 1H), 7.66-7.72 (m, 1H), 7.55-7.62 (m, 2H), 7.48-7.54 (m, 3H), 7.37-7.44 (m, 2H), 6.04 (s, 1H), 2.28 (s, 3H); MS (ESI $C_{22}H_{14}Cl_3N_2O$ $[M-H]^-$ m/z expected=427.0, observed=426.9; HPLC-1=>99%; HPLC-2=>99%.

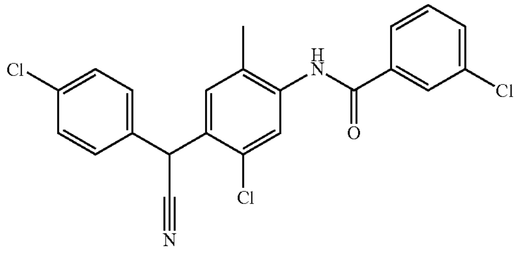 [SMILES: Cc1cc(C(C#N)c2ccc(Cl)cc2)c(Cl)cc1NC(=O)c1cccc(Cl)c1]

Example 35

Analog 78: 4-chloro-N-(5-chloro-4-((4-chlorophenyl)(cyano)methyl)-2-methylphenyl)benzamide. $^1$H-NMR (300 MHz, $d_6$-DMSO) δ10.08 (s, 1H), 7.95-8.01 (m, 2H), 7.59-7.66 (m, 3H), 7.48-7.54 (m, 3H), 7.37-7.43 (m, 4H), 6.04 (s, 1H), 2.28 (s, 3H); MS (ESI) $C_{22}H_{14}Cl_3N_2O$ $[M-H]^-$ m/z expected=427.0, observed=426.9; HPLC-1=>99%; HPLC-2=>99%.

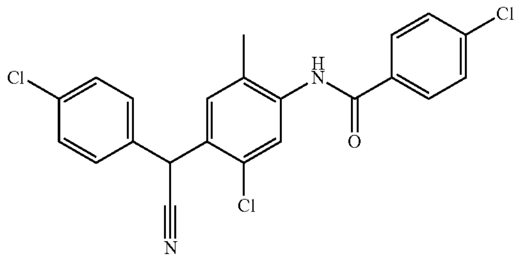 [SMILES: Cc1cc(C(C#N)c2ccc(Cl)cc2)c(Cl)cc1NC(=O)c1ccc(Cl)cc1]

Example 36

Analog 79: N-(5-chloro-4-((4-chlorophenyl)(cyano)methyl)-2-methylphenyl)-2-fluorobenzamide. $^1$H-NMR (300 MHz, $d_6$-DMSO) δ9.99 (s, 1H), 7.70-7.82 (m, 2H), 7.56-7.66 (m, 1H), 7.47-7.54 (m, 3H), 7.30-7.44 (m, 4H), 6.03 (s, 1H), 2.31 (s, 3H); MS (ESI) $C_{22}H_{14}Cl_2FN_2O$ $[M-H]^-$ m/z expected=411.0, observed=411.0; HPLC-1=99%; HPLC-2=95%.

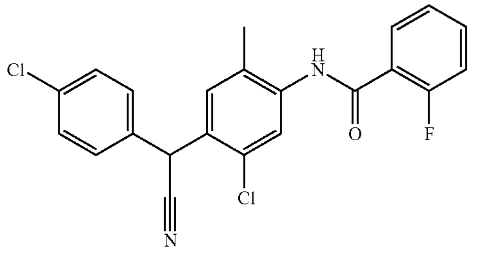 [SMILES: Cc1cc(C(C#N)c2ccc(Cl)cc2)c(Cl)cc1NC(=O)c1ccccc1F]

Example 37

Analog 80: N-(5-chloro-4-((4-chlorophenyl)(cyano)methyl)-2-methylphenyl)-3-fluorobenzamide. $^1$H-NMR (300 MHz, $d_6$-DMSO) δ10.09 (s, 1H), 7.85 (d, J=7.8 Hz, 1H), 7.76 (dt, J=9.8, 2.0 Hz, 1H), 7.56-7.65 (m, 2H), 7.43-7.54 (m, 4H), 7.37-7.43 (m, 2H), 6.04 (s, 1H), 2.29 (s, 3H); MS (ESI) $C_{22}H_{14}Cl_2FN_2O$ $[M-H]^-$ m/z expected=411.0, observed=410.9; HPLC-1=>99%; HPLC-2=>99%.

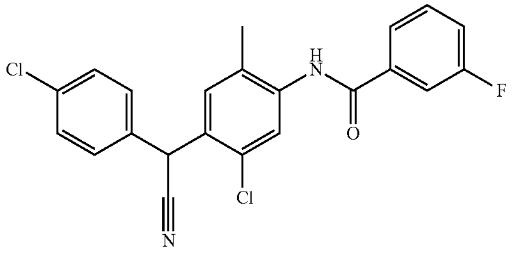 [SMILES: Cc1cc(C(C#N)c2ccc(Cl)cc2)c(Cl)cc1NC(=O)c1cccc(F)c1]

Example 38

Analog 81: N-(5-chloro-4-((4-chlorophenyl)(cyano)methyl)-2-methylphenyl)-4-fluorobenzamide. $^1$H-NMR (300 MHz, $d_6$-DMSO) δ10.02 (s, 1H), 8.00-8.08 (m, 2H), 7.61 (s, 1H), 7.48-7.54 (m, 3H), 7.34-7.44 (m, 4H), 6.04 (s, 1H), 2.28 (s, 3H); MS (ESI) $C_{22}H_{14}Cl_2FN_2O$ $[M-H]^-$ m/z expected=411.0, observed=411.0; HPLC-1=>99%; HPLC-2=>99%.

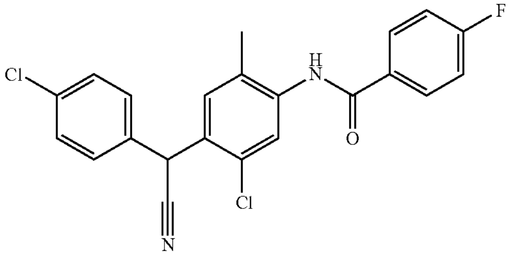 [SMILES: Cc1cc(C(C#N)c2ccc(Cl)cc2)c(Cl)cc1NC(=O)c1ccc(F)cc1]

Example 39

Analog 82: N-(5-chloro-4-((4-chlorophenyl)(cyano)methyl)-2-methylphenyl)benzamide. $^1$H-NMR (300 MHz, $d_6$-DMSO) δ10.00 (s, 1H), 7.94-7.99 (m, 2H), 7.48-7.65 (m, 7H), 7.38-7.43 (m, 2H), 6.04 (s, 1H), 2.29 (s, 3H); MS (ESI) $C_{22}H_{15}Cl_2N_2O$ $[M-H]^-$ m/z expected=393.1, observed=393.0; HPLC-1=96%; HPLC-2=>99%.

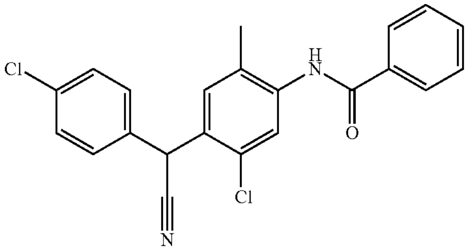 [SMILES: Cc1cc(C(C#N)c2ccc(Cl)cc2)c(Cl)cc1NC(=O)c1ccccc1]

Example 40

Analog 83: N-(5-chloro-4-((4-chlorophenyl)(cyano)methyl)-2-methylphenyl)acetamide. $^1$H-NMR (300 MHz, $d_6$-DMSO) δ9.41 (s, 1H), 7.74 (s, 1H), 7.46-7.53 (m, 2H), 7.42 (s, 1H), 7.34-7.39 (m, 2H), 5.98 (s, 1H), 2.24 (s, 3H), 2.09 (s, 3H); MS (ESI) $C_{17}H_{13}Cl_2N_2O$ $[M-H]^-$ m/z expected=331.0, observed=331.0; HPLC-1=99%; HPLC-2=98%.

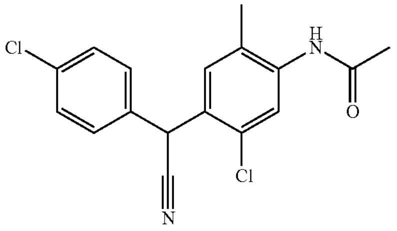 [SMILES: CC(=O)Nc1cc(Cl)c(C(C#N)c2ccc(Cl)cc2)cc1C]

Example 41

Analog 84: 5-chloro-N-(4-(cyano(phenyl)methyl)phenyl)-2-methoxybenzamide. $^1$H-NMR (300 MHz, $d_6$-DMSO) δ10.28 (s, 1H), 7.71-7.77 (m, 2H), 7.51-7.59 (m, 2H), 7.32-7.44 (m, 7H), 7.20 (d, J=8.8 Hz, 1H), 5.78 (s, 1H), 3.86 (s, 3H); MS (ESI) $C_{22}H_{16}ClN_2O_2$ $[M-H]^-$ m/z expected=375.1, observed=375.0; HPLC-1=97%; HPLC-2=96%.

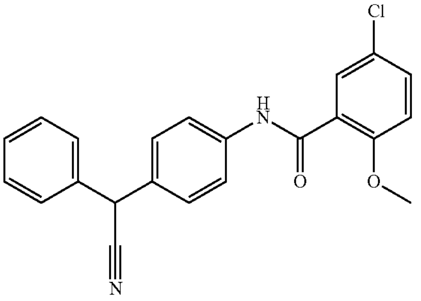 [SMILES: COc1ccc(Cl)cc1C(=O)Nc1ccc(C(C#N)c2ccccc2)cc1]

Example 42

Analog 85: 5-chloro-N-(4-(cyano(phenyl)methyl)phenyl)-2-hydroxybenzamide. $^1$H-NMR (300 MHz, $d_6$-DMSO) δ11.79 (br s, 1H), 10.50 (s, 1H), 7.92 (d, J=2.7 Hz, 1H), 7.70-7.77 (m, 2H), 7.46 (dd, J=8.8, 2.7 Hz, 1H), 7.38-7.44 (m, 6H), 7.30-7.38 (m, 1H), 7.00 (d, J=8.8 Hz, 1H), 5.80 (s, 1H); MS (ESI) $C_{21}H_{14}ClN_2O_2$ $[M-H]^-$ m/z expected=361.1, observed=361.0; HPLC-1=98%; HPLC-2=97%.

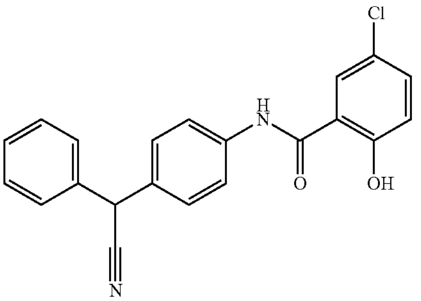 [SMILES: N#CC(c1ccccc1)c1ccc(NC(=O)c2cc(Cl)ccc2O)cc1]

Example 43

Analog 86: 5-chloro-N-(3-chloro-4-(4-chlorophenoxy)phenyl)-2-methoxybenzamide. $^1$H-NMR (300 MHz, $d_6$-DMSO) δ10.42 (s, 1H), 8.07 (d, J=2.4 Hz, 1H), 7.67 (dd, J=8.9, 2.5 Hz, 1H), 7.60 (d, J=2.6 Hz, 1H), 7.56 (dd, J=8.8, 2.7 Hz, 1H), 7.37-7.45 (m, 2H), 7.22 (dd, J=8.8, 1.2 Hz, 2H), 6.91-6.98 (m, 2H), 3.88 (s, 3H); MS (ESI) $C_{20}H_{13}Cl_3NO_3$ $[M-H]^-$ m/z expected=420.0, observed=419.9; HPLC-1=>99%; HPLC-2=>99%.

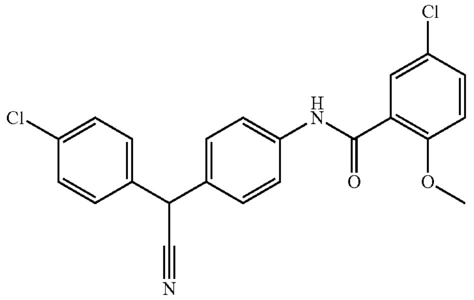 [SMILES: COc1ccc(Cl)cc1C(=O)Nc1ccc(C(C#N)c2ccc(Cl)cc2)cc1]

Example 44

Analog 87: 5-chloro-N-(3-chloro-4-(4-chlorophenoxy)phenyl)-2-hydroxybenzamide. $^1$H-NMR (300 MHz, $d_6$-DMSO) δ11.65 (br s, 1H), 10.55 (s, 1H), 8.07 (d, J=2.5 Hz, 1H), 7.89 (d, J=2.6 Hz, 1H), 7.67 (dd, J=8.8, 2.5 Hz, 1H), 7.47 (dd, J=8.8, 2.7 Hz, 1H), 7.38-7.45 (m, 2H), 7.23 (d, J=8.8 Hz, 1H), 7.02 (d, J=8.8 Hz, 1H), 6.92-6.99 (m, 2H); MS (ESI) $C_{19}H_{11}Cl_3NO_3$ $[M-H]^-$ m/z expected=406.0, observed=405.9; HPLC-1=>99%; HPLC-2=>99%.

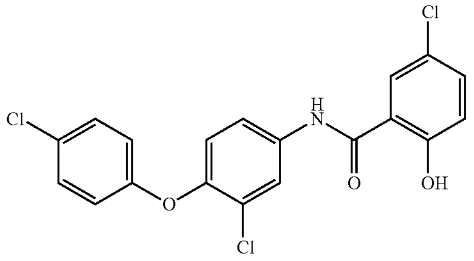 [SMILES: O=C(Nc1ccc(Oc2ccc(Cl)cc2)c(Cl)c1)c1cc(Cl)ccc1O]

Example 45

Analog 88: 5-chloro-N-(4-(4-chlorophenoxy)phenyl)-2-methoxybenzamide. $^1$H-NMR (300 MHz, $d_6$-DMSO) δ10.24 (s, 1H), 7.71-7.80 (m, 2H), 7.59 (d, J=2.7 Hz, 1H), 7.54 (dd, J=8.8, 2.8 Hz, 1H), 7.38-7.46 (m, 2H), 7.20 (d, J=8.9 Hz, 1H), 7.02-7.09 (m, 2H), 6.96-7.02 (m, 2H), 3.87 (s, 3H); MS (ESI) $C_{20}H_{14}Cl_2NO_3$ $[M-H]^-$ m/z expected=386.0, observed=386.0; HPLC-1=99%; HPLC-2=>99%.

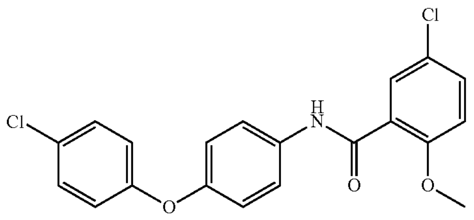 [SMILES: COc1ccc(Cl)cc1C(=O)Nc1ccc(Oc2ccc(Cl)cc2)cc1]

Example 46

Analog 89: 5-chloro-N-(4-(4-chlorophenoxy)phenyl)-2-hydroxybenzamide. $^1$H-NMR (300 MHz, $d_6$-DMSO) δ11.86 (br s, 1H), 10.47 (s, 1H), 7.95 (d, J=2.7 Hz, 1H), 7.70-7.77 (m, 2H), 7.39-7.50 (m, 3H), 7.05-7.11 (m, 2H), 6.98-7.05

(m, 3H); MS (ESI) $C_{19}H_{13}Cl_2NO_3$ $[M-H]^-$ m/z expected=372.0, observed=371.9; HPLC-1=>99%; HPLC-2=>99%.

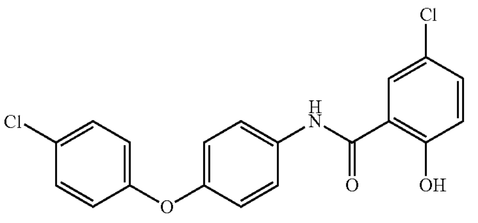 [SMILES: O=C(Nc1ccc(Oc2ccc(Cl)cc2)cc1)c1cc(Cl)ccc1O]

Example 47

Analog 90: 5-chloro-N-(3-chloro-4-phenoxyphenyl)-2-methoxybenzamide. $^1$H-NMR (300 MHz, $d_6$-DMSO) δ10.40 (s, 1H), 8.07 (d, J=2.5 Hz, 1H), 7.65 (dd, J=8.8, 2.5 Hz, 1H), 7.61 (d, J=2.7 Hz, 1H), 7.56 (dd, J=8.8, 2.5 Hz, 1H), 7.32-7.41 (m, 2H), 7.22 (d, J=8.8 Hz, 1H), 7.17 (d, J=8.8 Hz, 1H), 7.07-7.14 (m, 1H), 6.88-6.95 (m, 2H), 3.88 (s, 3H); MS (ESI) $C_{20}H_{14}Cl_2NO_3$ $[M-H]^-$ m/z expected=386.0, observed=386.0; HPLC-1=97%; HPLC-2=>99%.

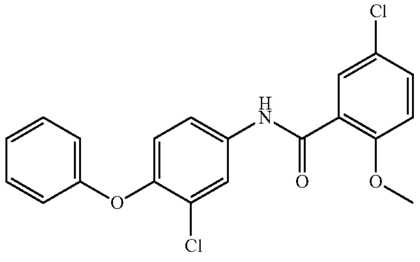 [SMILES: COc1ccc(Cl)cc1C(=O)Nc1ccc(Oc2ccccc2)c(Cl)c1]

Example 48

Analog 91: 5-chloro-N-(3-chloro-4-phenoxyphenyl)-2-hydroxybenzamide. $^1$H-NMR (300 MHz, $d_6$-DMSO) δ11.66 (br s, 1H), 10.54 (s, 1H), 8.07 (d, J=2.5 Hz, 1H), 7.90 (d, J=2.7 Hz, 1H), 7.65 (dd, J=8.9, 2.6 Hz, 1H), 7.47 (dd, J=8.8, 2.7 Hz, 1H), 7.34-7.43 (m, 2H), 7.17 (d, J=8.8 Hz, 1H), 7.08-7.15 (m, 1H), 7.02 (d, J=8.8 Hz, 1H), 6.90-6.97 (m, 2H); MS (ESI) $C_{19}H_{12}Cl_2NO_3$ $[M-H]^-$ m/z expected=372.0, observed=371.9; HPLC-1=>99%; HPLC-2=>99%.

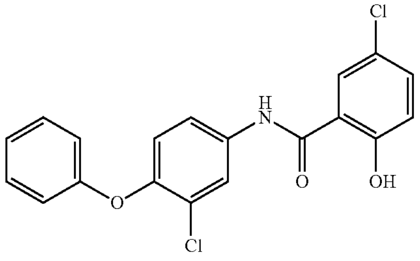 [SMILES: O=C(Nc1ccc(Oc2ccccc2)c(Cl)c1)c1cc(Cl)ccc1O]

Example 49

Analog 92: 5-chloro-2-methoxy-N-(4-phenoxyphenyl) benzamide. $^1$H-NMR (300 MHz, $d_6$-DMSO) δ10.22 (s, 1H), 7.70-7.77 (m, 2H), 7.60 (d, J=2.7 Hz, 1H), 7.54 (dd, J=8.8, 2.7 Hz, 1H), 7.33-7.41 (m, 2H), 7.21 d, J=8.8 Hz, 1H), 7.07-7.14 (m, 1H), 7.01-7.06 (m, 2H), 6.94-7.00 (m, 2H), 3.88 (s, 3H); MS (ESI) $C_{20}H_{15}ClNO_3$ $[M-H]^-$ m/z expected=352.1, observed=352.0; HPLC-1=>99%; HPLC-2=>99%.

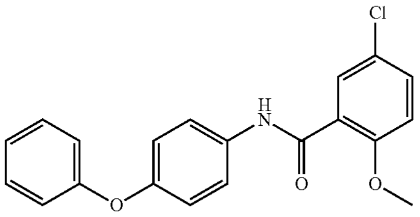 [SMILES: COc1ccc(Cl)cc1C(=O)Nc1ccc(Oc2ccccc2)cc1]

Example 50

Analog 93: 5-chloro-2-hydroxy-N-(4-phenoxyphenyl) benzamide. $^1$H-NMR (300 MHz, $d_6$-DMSO) δ11.87 (br s, 1H), 10.48 (s, 1H), 7.96 (d, J=2.7 Hz, 1H), 7.67-7.76 (m, 2H), 7.47 (dd, J=8.8, 2.7 Hz, 1H), 7.35-7.43 (m, 2H), 7.09-7.16 (m, 1H), 6.97-7.08 (m, 5H); MS (ESI) $C_{19}H_{13}ClNO_3$ $[M-H]^-$ m/z expected=338.1, observed=338.0; HPLC-1=99%; HPLC-2=>99%.

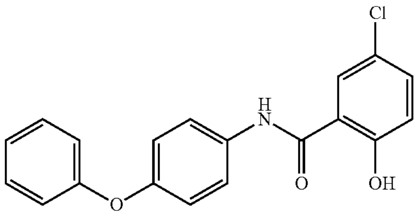 [SMILES: O=C(Nc1ccc(Oc2ccccc2)cc1)c1cc(Cl)ccc1O]

Example 51

Analog 94: N-(4-(benzo[d]thiazol-2-ylthio)-3-chlorophenyl)-5-chloro-2-methoxybenzamide. $^1$H-NMR (300 MHz, $d_6$-DMSO) δ10.71 (s, 1H), 8.22 (d, J=2.1 Hz, 1H), 7.92-7.99 (m, 2H), 7.79-7.88 (m, 2H), 7.64 (d, J=2.6 Hz, 1H), 7.59 (dd, J=8.8, 2.6 Hz, 1H), 7.47 (td, J=7.7, 1.3 Hz, 1H), 7.31-7.39 (m, 1H), 7.24 (d, J=8.8 Hz, 1H), 3.89 (s, 3H); MS (ESI) $C_{21}H_{13}Cl_2N_2O_2S_2$ $[M-H]^-$ m/z expected=459.0, observed=458.8; HPLC-1=>99%; HPLC-2=>99%.

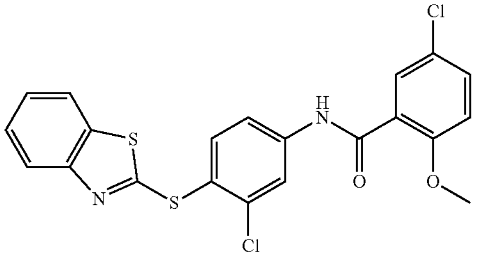 [SMILES: COc1ccc(Cl)cc1C(=O)Nc1ccc(Sc2nc3ccccc3s2)c(Cl)c1]

Example 52

Analog 95: N-(4-(benzo[d]thiazol-2-ylthio)-3-chlorophenyl)-5-chloro-2-hydroxybenzamide $^1$H-NMR (300 MHz, $d_6$-DMSO) δ11.45 (s, 1H), 10.73 (s, 1H), 8.25 (d, J=2.1 Hz, 1H), 7.91-8.00 (m, 2H), 7.81-7.88 (m, 3H), 7.42-7.51 (m, 2H), 7.31-7.39 (m, 1H), 7.05 (d, J=8.8 Hz, 1H); MS (ESI) $C_{20}H_{11}Cl_2N_2O_2S_2$ $[M-H]^-$ m/z expected=445.0, observed=444.9; HPLC-1=97%; HPLC-2=97%.

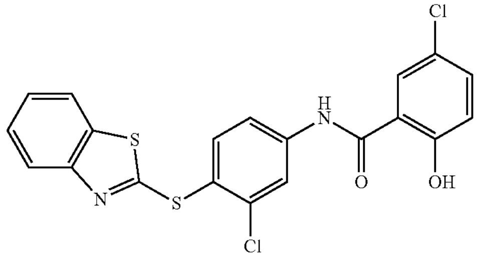 [SMILES: O=C(Nc1ccc(Sc2nc3ccccc3s2)c(Cl)c1)c1cc(Cl)ccc1O]

Example 53

Analog 96: N-(4-(benzo thiazol-2-ylthio)phenyl)-5-chloro-2-methoxybenzamide. $^1$H-NMR (300 MHz, $d_6$-DMSO) δ10.58 (s, 1H), 7.89-7.97 (m, 3H), 7.76-7.86 (m, 3H), 7.62 (d, J=2.6 Hz, 1H), 7.57 (dd, J=8.9, 2.6 Hz, 1H), 7.45 (td, J=7.7, 1.3 Hz, 1H), 7.29-7.37 (m, 1H), 7.23 (d, J=8.9 Hz, 1H), 3.89 (s, 3H); MS (ESI) $C_{21}H_{14}Cl_2N_2O_2S_2$ $[M-H]^-$ m/z expected=425.0, observed=424.9; HPLC-1=98%; HPLC-2=>99%.

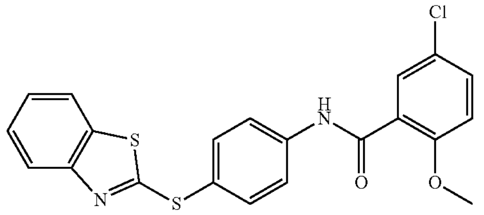 [SMILES: COc1ccc(Cl)cc1C(=O)Nc1ccc(Sc2nc3ccccc3s2)cc1]

Example 54

Analog 97: N-(4-(benzo thiazol-2-ylthio)phenyl)-5-chloro-2-hydroxybenzamide. $^1$H-NMR (300 MHz, $d_6$-DMSO) δ11.56 (br s, 1H), 10.68 (s, 1H), 7.90-7.98 (m, 3H), 7.89 (d, J=2.6 Hz, 1H), 7.78-7.86 (m, 3H), 7.41-7.52 (m, 2H), 7.29-7.37 (m, 1H), 7.04 (d, J=8.8 Hz, 1H); MS (ESI) $C_{20}H_{12}Cl_2N_2O_2S_2$ $[M-H]^-$ m/z expected=411.0, observed=410.9; HPLC-1=>99%; HPLC-2=>99%.

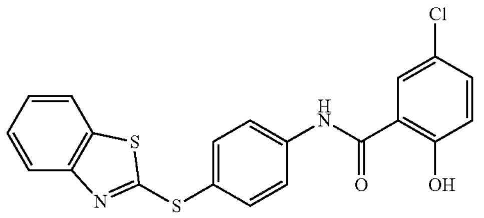 [SMILES: O=C(Nc1ccc(Sc2nc3ccccc3s2)cc1)c1cc(Cl)ccc1O]

Example 55

Analog 98: N-(4-benzylphenyl)-5-chloro-2-methoxybenzamide. $^1$H-NMR (300 MHz, $d_6$-DMSO) δ10.13 (s, 1H), 7.59-7.65 (m, 2H), 7.58 (d, J=2.6 Hz, 1H), 7.53 (dd, J=8.8, 2.6 Hz, 1H), 7.25-7.32 (m, 2H), 7.16-7.24 (m, 6H), 3.90 (s, 2H), 3.87 (s, 3H); MS (ESI) $C_{21}H_{17}Cl_2NO_2$ $[M-H]^-$ m/z expected=350.1, observed=350.0; HPLC-1=>99%; HPLC-2=>99%.

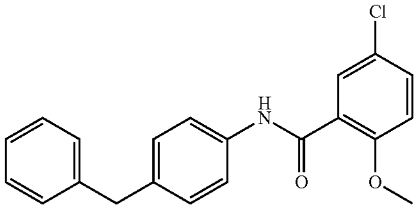 [SMILES: COc1ccc(Cl)cc1C(=O)Nc1ccc(Cc2ccccc2)cc1]

Example 56

Analog 99: N-(4-benzylphenyl)-5-chloro-2-hydroxybenzamide. (300 MHz, $d_6$-DMSO) δ11.92 (br s, 1H), 10.40 (s, 1H), 7.96 (d, J=2.7 Hz, 1H), 7.58-7.64 (m, 2H), 7.46 (dd, J=8.8, 2.7 Hz, 1H), 7.14-7.33 (m, 7H), 7.00 (d, J=8.8 Hz, 1H), 3.92 (s, 2H); MS (ESI) $C_{20}H_{15}ClNO_2$ $[M-H]^-$ m/z expected=336.1, observed=336.0; HPLC-1=96%; HPLC-2=97%.

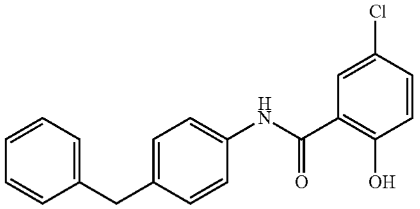 [SMILES: O=C(Nc1ccc(Cc2ccccc2)cc1)c1cc(Cl)ccc1O]

Example 57

Analog 100: 5-chloro-2-methoxy-N-(4-phenethylphenyl) benzamide. $^1$H-NMR (300 MHz, $d_6$-DMSO) δ10.12 (s, 1H), 7.58-7.63 (m, 3H), 7.54 (dd, J=8.8, 2.7 Hz, 1H), 7.13-7.31 (m, 8H), 3.88 (s, 3H), 2.86 (s, 4H); MS (ESI) $C_{22}H_{19}ClNO_2$ $[M-H]^-$ m/z expected=364.1, observed=364.1; HPLC-1=98%; HPLC-2=99%.

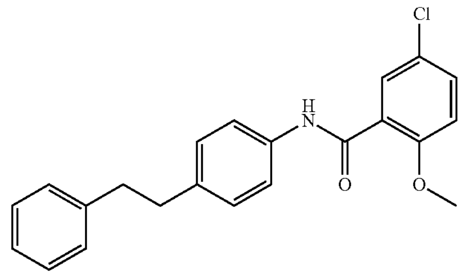 [SMILES: COc1ccc(Cl)cc1C(=O)Nc1ccc(CCc2ccccc2)cc1]

Example 58

Analog 101: 5-chloro-2-methoxy-N-(4-phenethylphenyl) benzamide. $^1$H-NMR (300 MHz, $d_6$-DMSO) δ11.93 (s, 1H), 10.36 (s, 1H), 7.97 (d, J=2.7 Hz, 1H), 7.59 (d, J=8.5 Hz, 2H), 7.46 (dd, J=8.8, 2.7 Hz, 1H), 7.13-7.31 (m, 7H), 7.01 (d, J=8.8 Hz, 1H), 2.87 (s, 4H); MS (ESI) $C_{21}H_{17}ClNO_2$ $[M-H]^-$ m/z expected=350.1, observed=350.0; HPLC-1=97%; HPLC-2=94%.

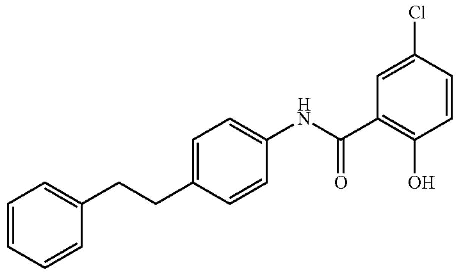 [SMILES: O=C(Nc1ccc(CCc2ccccc2)cc1)c1cc(Cl)ccc1O]

Example 59

Analog 102: N-(4-(benzyloxy)phenyl)-5-chloro-2-methoxybenzamide. $^1$H-NMR (300 MHz, $d_6$-DMSO) δ10.06 (s, 1H), 7.58-7.66 (m, 3H), 7.53 (dd, J=8.8, 2.8 Hz, 1H), 7.29-7.48 (m, 5H), 7.19 (d, J=8.8 Hz, 1H), 6.96-7.03 (m, 2H), 5.09 (s, 2H), 3.88 (s, 3H); MS (ESI) $C_{21}H_{17}ClNO_3$ $[M-H]^-$ m/z expected=366.1, observed=366.0; HPLC-1=>99%; HPLC-2=>99%.

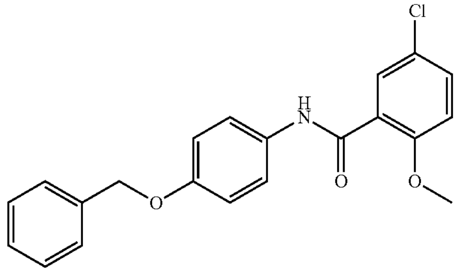

Example 60

Analog 103: N-(4-(benzyloxy)phenyl)-5-chloro-2-hydroxybenzamide. $^1$H-NMR (300 MHz, $d_6$-DMSO) δ12.02 (br, s, 1H), 10.34 (s, 1H), 7.98 (d, J=2.6 Hz, 1H), 7.55-7.64 (m, 2H), 7.43-7.50 (m, 3H), 7.29-7.43 (m, 3H), 6.97-7.07 (m, 3H), (s, 2H); MS (ESI) $C_{20}H_{15}ClNO_3$ $[M-H]^-$ m/z expected=352.1, observed=352.0; HPLC-1=>99%; HPLC-2=>99%.

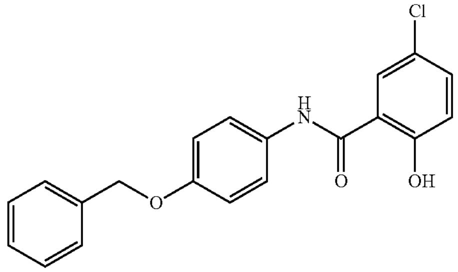

Example 61

Analog 104: N-(4-acetamidophenyl)-5-chloro-2-methoxybenzamide. $^1$H-NMR (300 MHz, $d_6$-DMSO) δ10.11 (s, 1H), 9.91 (s, 1H), 7.58-7.66 (m, 3H), 7.50-7.57 (m, 3H), 7.20 (d, J=8.9 Hz, 1H), 3.88 (s, 3H), 2.02 (s, 3H); MS (ESI) $C_{16}H_{14}ClN_2O_3$ $[M-H]^-$ m/z expected=317.1, observed=317.0; HPLC-1=>99%; HPLC-2=>99%.

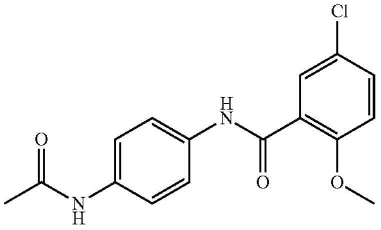 [SMILES: COc1ccc(Cl)cc1C(=O)Nc1ccc(NC(C)=O)cc1]

Example 62

Analog 105: N-(4-acetamidophenyl)-5-chloro-2-hydroxybenzamide. $^1$H-NMR (300 MHz, $d_6$-DMSO) δ11.96 (s, 1H), 10.37 (s, 1H), 9.95 (s, 1H), 7.98 (d, J=2.7 Hz, 1H), 7.54-7.64 (m, 4H), 7.46 (dd, J=8.8, 2.7 Hz, 1H), 7.00 (d, J=8.8 Hz, 1H), 2.03 (s, 3H); MS (ESI) $C_{15}H_{12}ClN_2O_3$ $[M-H]^-$ m/z expected=303.1, observed=303.0; HPLC-1=>99%; HPLC-2=>99%.

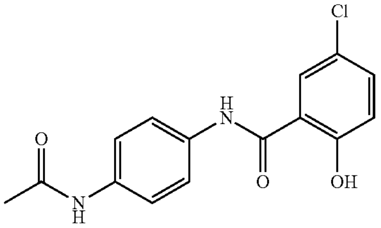 [SMILES: CC(=O)Nc1ccc(NC(=O)c2cc(Cl)ccc2O)cc1]

Example 63

Analog 106: methyl 4-(5-chloro-2-methoxybenzamido) benzoate. $^1$H-NMR (300 MHz, $d_6$-DMSO) δ10.54 (s, 1H), 7.92-7.98 (m, 2H), 7.82-7.88 (m, 2H), 7.60 (d, J=2.7 Hz, 1H), 7.56 (dd, J=8.8, 2.7 Hz, 1H), 7.22 (d, J=8.8 Hz, 1H), 3.87 (s, 3H), 3.83 (s, 3H); MS (ESI) $C_{16}H_{13}ClNO_4$ $[M-H]^-$ m/z expected=318.1, observed=318.0; HPLC-1=>99%; HPLC-2=>99%.

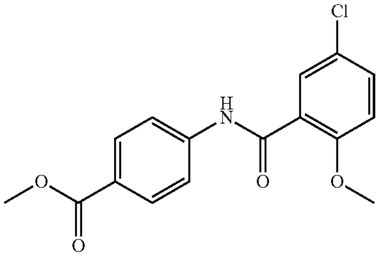

Example 64

Analog 107: methyl 4-(5-chloro-2-hydroxybenzamido) benzoate. $^1$H-NMR (300 MHz, $d_6$-DMSO) δ11.63 (br, s, 1H), 10.66 (s, 1H), 7.93-8.01 (m, 2H), 7.84-7.90 (m, 3H), 7.47 (dd, J=8.8, 2.7 Hz, 1H), 7.03 (d, J=8.8 Hz, 1H), 3.84 (s, 3H); MS (ESI) $C_{15}H_{11}ClNO_4$ $[M-H]^-$ m/z expected=304.0, observed=304.0; HPLC-1=>99%; HPLC-2=>99%.

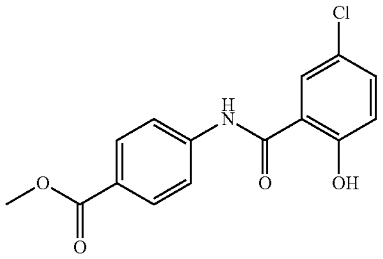 [SMILES: COC(=O)c1ccc(NC(=O)c2cc(Cl)ccc2O)cc1]

Example 65

Analog 108: 4-(5-chloro-2-methoxybenzamido)benzoic acid. $^1$H-NMR (300 MHz, $d_6$-DMSO) δ12.77 (br, s, 1H), 10.50 (s, 1H), 7.89-7.96 (m, 2H), 7.79-7.87 (m, 2H), 7.60 (d, J=2.6 Hz, 1H), 7.56 (dd, J=8.8m 2.6 Hz, 1H), 7.21 (d, J=8.8 Hz, 1H), 3.88 (s, 3H); MS (ESI) $C_{15}H_{11}ClNO_4$ $[M-H]^-$ m/z expected=304.0, observed=304.0; HPLC-1=>99%; HPLC-2=>99%.

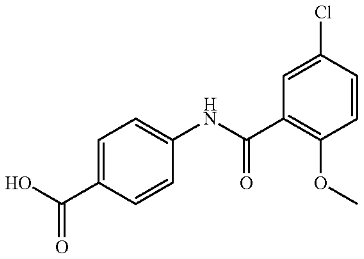 [SMILES: COc1ccc(Cl)cc1C(=O)Nc1ccc(C(=O)O)cc1]

Example 66

Analog 109: 4-(5-chloro-2-hydroxybenzamido)benzoic acid. $^1$H-NMR (300 MHz, $d_6$-DMSO) δ12.78 (br s, 1H), 11.65 (br s, 1H), 10.63 (s, 1H), 7.92-7.98 (m, 2H), 7.89 (d, J=2.7 Hz, 1H), 7.81-7.87 (m, 2H), 7.47 (dd, J=8.8, 2.7 Hz, 1H), 7.03 (d, J=8.8 Hz, 1H); MS (ESI) $C_{14}H_9ClNO_4$ $[M-H]^-$ m/z expected=290.0, observed=290.0; HPLC-1=>99%; HPLC-2=>99%.

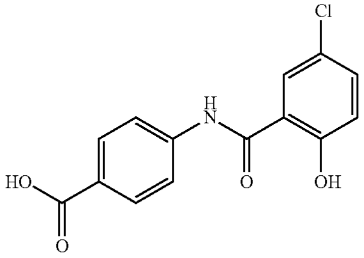 [SMILES: O=C(O)c1ccc(NC(=O)c2cc(Cl)ccc2O)cc1]

Example 67

Analog 110: 5-chloro-N-(4-(cyanomethyl)phenyl)-2-methoxybenzamide. $^1$H-NMR (300 MHz, $d_6$-DMSO) δ10.26 (s, 1H), 7.70-7.76 (m, 2H), 7.60 (d, J=2.7 Hz, 1H), 7.52-7.57 (m, 1H), 7.29-7.35 (m, 2H), 7.20 (d, J=8.9 Hz, 1H), 4.00 (s, 2H), 3.88 (s, 3H); MS (ESI) $C_{16}H_{12}ClN_2O_2$ $[M-H]^-$ m/z expected=299.1, observed=299.0; HPLC-1=98%; HPLC-2=98%.

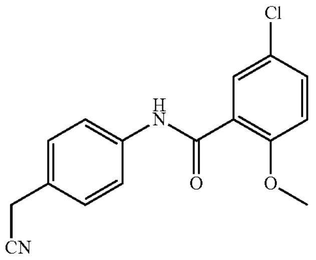 [SMILES: COc1ccc(Cl)cc1C(=O)Nc1ccc(CC#N)cc1]

Example 68

Analog 111: 5-chloro-N-(4-(cyanomethyl)phenyl)-2-hydroxybenzamide. $^1$H-NMR (300 MHz, $d_6$-DMSO) δ11.82 (br s, 1H), 10.47 (s, 1H), 7.95 (d, J=2.7 Hz, 1H), 7.69-7.76 (m, 2H), 7.47 (dd, J=8.8, 2.7 Hz, 1H), 7.30-7.39 (m, 2H), 7.01 (d, J=8.8 Hz, 1H), 4.02 (s, 2H); MS (ESI) $C_{15}H_{10}ClN_2O_2$ $[M-H]^-$ m/z expected=285.0, observed=285.0; HPLC-1=98%; HPLC-2=98%.

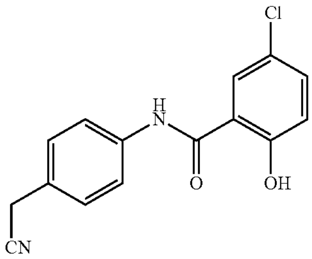 [SMILES: N#CCc1ccc(NC(=O)c2cc(Cl)ccc2O)cc1]

Example 69

Analog 112: 5-chloro-2-methoxy-N-(4-methoxyphenyl)benzamide. $^1$H-NMR (300 MHz, $d_6$-DMSO) δ10.05 (s, 1H), 7.58-7.66 (m, 3H), 7.53 (dd, J=8.8, 2.8 Hz, 1H), 7.20 (d, J=8.9 Hz, 1H), 6.88-6.95 (m, 2H), 3.88 (s, 3H), 3.74 (s, 3H); MS (ESI) $C_{15}H_{13}ClNO_3$ $[M-H]^-$ m/z expected=290.1, observed=290.0; HPLC-1=>99%; HPLC-2=>99%.

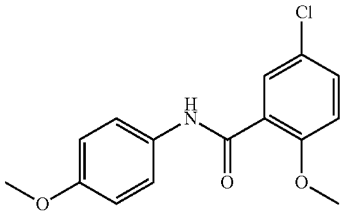

Example 70

Analog 113: 5-chloro-2-hydroxy-N-(4-methoxyphenyl)benzamide. $^1$H-NMR (300 MHz, $d_6$-DMSO) δ12.04 (br s, 1H), 10.34 (s, 1H), 7.99 (d, J=2.7 Hz, 1H), 7.56-7.63 (m, 2H), 7.46 (dd, J=8.8, 2.7 Hz, 1H), 7.01 (d, J=8.8 Hz, 1H), 6.92-6.97 (m, 2H), 3.75 (s, 3H); MS (ESI) $C_{14}H_{11}ClNO_3$ $[M-H]^-$ m/z expected=276.0, observed=276.0; HPLC-1=>99%; HPLC-2=>99%.

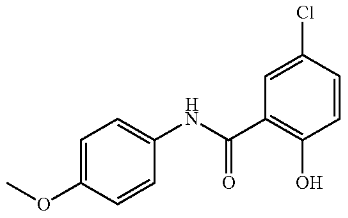 [SMILES: COc1ccc(NC(=O)c2cc(Cl)ccc2O)cc1]

Example 71

Analog 114: 5-chloro-N-(4-hydroxyphenyl)-2-methoxybenzamide. $^1$H-NMR (300 MHz, $d_6$-DMSO) δ9.94 (s, 1H), 9.27 (s, 1H), 7.59 (d, J=2.8 Hz, 1H), 7.45-7.55 (m, 3H), 7.19 (d, J=8.8 Hz, 1H), 6.69-6.76 (m, 2H), 3.88 (s, 3H); MS (ESI) $C_{14}H_{11}ClNO_3$ $[M-H]^-$ m/z expected=276.0, observed=276.0; HPLC-1=99%; HPLC-2=99%.

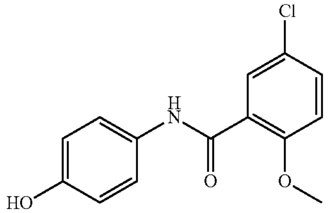 [SMILES: COc1ccc(Cl)cc1C(=O)Nc1ccc(O)cc1]

Example 72

Analog 115: 5-chloro-2-hydroxy-N-(4-hydroxyphenyl) benzamide. $^1$H-NMR (300 MHz, $d_6$-DMSO) δ12.12 (S, 1H), 10.25 (s, 1H), 9.37 (s, 1H), 8.00 (d, J=2.6 Hz, 1H), 7.41-7.51 (m, 3H), 6.99 (d, J=8.8 Hz, 1H), 6.72-6.81 (m, 2H); MS (ESI) $C_{13}H_9ClNO_3$ $[M-H]^-$ m/z expected=262.0, observed=262.0; HPLC-1=>99%; HPLC-2=>99%.

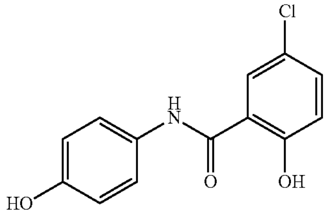 [SMILES: O=C(Nc1ccc(O)cc1)c1cc(Cl)ccc1O]

Example 73

Analog 116: 5-chloro-2-methoxy-N-phenylbenzamide. $^1$H-NMR (300 MHz, $d_6$-DMSO) δ10.19 (s, 1H), 7.68-7.74 (m, 2H), 7.60 (d, J=2.7 Hz, 1H), 7.51-7.57 (m, 1H), 7.30-7.38 (m, 2H), 7.21 (d, J=8.8 Hz, 1H), 7.06-7.13 (m, 1H), 3.88 (s, 3H); MS (ESI) $C_{14}H_{13}ClNO_2$ $[M-H]^+$ m/z expected=262.1, observed=262.0; HPLC-1=99%; HPLC-2=>99%.

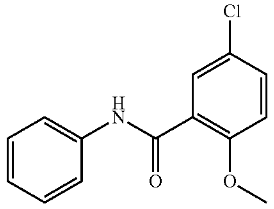 [SMILES: COc1ccc(Cl)cc1C(=O)Nc1ccccc1]

Example 74

Analog 117: 5-chloro-2-hydroxy-N-phenylbenzamide. $^1$H-NMR (300 MHz, $d_6$-DMSO) δ11.87 (br s, 1H), 10.42 (s, 1H), 7.96 (d, J=2.6 Hz, 1H), 7.66-7.74 (m, 2H), 7.47 (dd, J=8.8, 2.7 Hz, 1H), 7.33-7.42 (m, 2H), 7.11-7.18 (m, 1H), 7.01 (d, J=8.8 Hz, 1H); MS (ESI) $C_{13}H_9ClNO_2$ $[M-H]^-$ m/z expected=246.0, observed=246.0; HPLC-1=>99%; HPLC-2=>99%.

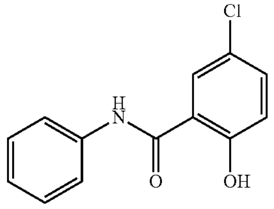 [SMILES: O=C(Nc1ccccc1)c1cc(Cl)ccc1O]

Example 75

Protein Expression and Purification.

*E. coli* GroEL and GroES purification. *E. coli* GroEL was expressed from a trc-promoted and Amp(+) resistance marker plasmid in DH5a. *E. coli* cells. GroES was expressed from a T7-promoted and Amp(+) resistance plasmid in *E. coli* BL21 (DE3) cells. Transformed colonies were plated onto Ampicillin-treated LB agar and incubated for 24 h at 37° C. Cells were then grown at 37° C. in Ampicillin-treated LB medium until an $OD_{600}$ of 0.5 was reached, then were induced with 0.8 mM IPTG and continued to grow for 2-3 h at 37° C. The cultures were centrifuged at 8,000 rpm and the cell pellets were collected and re-suspended in Buffer A (50 mM Tris-HCl, pH 7.4, and 20 mM NaCl) supplemented with EDTA-free complete protease inhibitor cocktail (Roche). The combined suspension was lysed by sonication, the lysate was centrifuged at 14,000 rpm, and the clarified lysate was passed through a 0.45 μm filter (Millipore).

Anion exchange purification. The filtered lysate was loaded onto a GE HiScale Anion exchange column (Q Sepharose fast flow anion exchange resin) that was equilibrated with 2 column volumes of Buffer A. The loaded column was washed with 4 column volumes of Buffer A containing 30% of Buffer B (50 mM Tris-HCl, pH 7.4, and 1 M NaCl), then bound protein was eluted with a 30-60% gradient elution of Buffer B. Protein-containing fractions, as identified by SDS-PAGE, were collected, spin concentrated using a 10 kDa Amicon Ultra-15 centrifugal filter (EMD Millipore), and dialyzed overnight with 10 kDa SnakeSkin™ dialysis tubing (Thermo Scientific) at 4° C. in 50 mM Tris-HCl, pH 7.4, and 150 mM NaCl solution.

Size exclusion chromatography. The dialyzed protein was loaded onto a Superdex 200 column (HiLoad 26/600, GE)

that was equilibrated with 2 column volumes of 50 mM Tris-HCl, pH 7.4, and 150 mM NaCl solution. The loaded column was eluted with 3 column volumes of 50 mM Tris-HCl, pH 7.4, and 150 mM NaCl solution. Protein-containing fractions, as identified by SDS-PAGE, were collected, spin concentrated using a 10 kDa Amicon Ultra-15 centrifugal filter (EMD Millipore), and dialyzed overnight with 10 kDa SnakeSkin™ dialysis tubing (Thermo Scientific) at 4° C. in 50 mM Tris-HCl, pH 7.4, and 150 mM NaCl solution. The final protein concentration was determined by Coomassie Protein Assay Kit (Thermo Scientific). Batches of GroEL and GroES proteins for testing were stored at 4° C. for up to one month then discarded.

Human HSP60 purification. Human HSP60 (mtHSP60) was expressed from a T7-promoted plasmid in Rosetta™ 2 (DE3) in *E. coli* cells. For human HSP60 purification, a pET21-HSP60 plasmid with an N-terminal octa-Histidine tag was transformed into Rosetta™ 2 (DE3) *E. coli* cells for over-expression. Cells were grown at 37° C. in LB/ampicillin/chloramphenicol medium until an $OD_{600}$ of 0.5 was reached, then cultures were induced with 0.5 mM IPTG and continued to grow for 2-3 h at 25° C. Cells were centrifuged at 14,000 rpm, and the cell pellet was suspended in 50 mL of lysis buffer composed of 100 mM Tris-HCl, pH 7.7, 10 mM $MgSO_4$, 1 mM β-ME, 5% glycerol, 0.1% triton X-100, 1500 Units DNAase, 50 μg/ml lysozyme, and one tablet of EDTA-free complete protease inhibitor cocktail (Roche). Cells were homogenized and passed through a microfluidizer, washing with buffer containing 10 mM Tris-HCl, pH 7.7, 5% glycerol, and 0.1% triton X-100.

1st Nickel column purification and His-tag cleavage: The cell lysate was centrifuged at 14,000 rpm, then the clarified lysate was supplemented with 10 mM imidazole, passed through a 0.2 μm filter, and loaded onto a nickel-agarose resin column that was equilibrated with 2 column volume of 20 mM Tris-HCl pH, 7.7, 5% glycerol, 200 mM NaCl, and 10 mM imidazole. The sample loaded column was washed with 6 column volumes of 50 mM imidazole, then bound HSP60 was eluted with 500 mM imidazole. Fractions that were enriched with the His-tagged mtHSP60 were collected, concentrated, dialyzed at room temperature for 2 h in 4 L of 20 mM Tris-HCl, pH 7.7, 200 mM NaCl and 5% glycerol. Proteolytic cleavage of the His-tag was next performed by addition of His-tagged TEV protease at a 1:10 (w:w) ratio, while dialyzing over night at 4° C. against 4 L of 20 mM Tris-HCl, pH 7.7, 200 mM NaCl, and 5% glycerol buffer.

2nd Nickel column purification: The protein sample was loaded onto a second nickel-agarose resin column that was equilibrated with 20 mM Tris-HCl, pH 7.7, 5% glycerol, 10 mM NaCl, and 10 mM imidazole. With this column, undigested His-tagged mtHSP60 can be separated from digested His-tag removed mtHSP60. The unbound fractions enriched with His-tag cleaved mtHSP60 were collected, and anion exchange chromatography was performed on the same day.

Anion exchange purification of His-tag removed mtHSP60: The protein sample was next loaded onto an anion-exchange column that was equilibrated with mM Tris-HCl, pH 7.7, and 5% glycerol. Bound proteins were eluted from the column with a linear gradient of 100-400 mM NaCl. Fractions enriched with mtHSP60 were collected, concentrated, and dialyzed in storage buffer (20 mM Tris-HCl, pH 7.7, 300 mM NaCl, 5% glycerol, and 10 mM $MgCl_2$) using 10 kDa SnakeSkin™ dialysis tubing (Thermo Scientific). The concentration of protein was determined by Coomassie Protein Assay Kit (Thermo Scientific). Batches of HSP60 protein for testing were stored at 4° C. for up to two weeks, then discarded.

Human HSP10 purification: Human HSP10 (mtHSP10) was expressed from a T7-promoted (pET3a-HSP10) plasmid in Rosetta™ 2 (DE3) pLysS cells. Cells were grown at 37° C. in LB/kanamycin/chloramphenicol medium until an $OD_{600}$ of 0.5 was reached, then were induced with 0.5 mM IPTG and continued to grow for 2-3 h at 37° C. The culture was centrifuged at 14,000 rpm, and the cell pellet was re-suspended in Buffer A (50 mM sodium acetate, pH 4.5, and 20 mM NaCl), supplemented with EDTA-free complete protease inhibitor cocktail (Roche®) and lysed by sonication. Clarified cell lysate was loaded on a cation exchange column (SP Sepharose fast flow resin, GE) and eluted with a linear NaCl gradient using Buffer B (50 mM sodium acetate, pH 4.5, and 1 M NaCl). Fractions containing HSP10 were concentrated, dialyzed with storage buffer (50 mM Tris-HCl, pH 7.4, and 300 mM NaCl) using 10 kDa SnakeSkin™ dialysis tubing (Thermo Scientific) and re-purified on a Superdex 200 column (HiLoad 26/600, GE) in storage buffer. The concentration of protein was determined by Coomassie Protein Assay Kit (Thermo Scientific). Protein was stored at 4° C. in 50 mM Tris-HCl, pH 7.4, and 150 mM NaCl. Batches of HSP10 protein for testing were stored at 4° C. for up to three weeks, then discarded.

Example 76

Evaluation of Compounds Ability to Inhibit GroEL/ES and HSP60/10-Mediated dMDH Refolding Assays.

Reagent preparation: For these assays, four primary reagent stocks were prepared: 1) GroEL/ES-dMDH or HSP60/10-dMDH binary complex stock; 2) ATP initiation stock; 3) EDTA quench stock; 4) MDH enzymatic assay stock. Denatured MDH (dMDH) was prepared by 2-fold dilution of MDH (5 mg/ml, soluble pig heart MDH from Roche, product #10127248001) with denaturant buffer (7 M guanidine-HCl, 200 mM Tris, pH 7.4, and 50 mM DTT). MDH was completely denatured by incubating at room temperature for 45 min. The binary complex solutions were prepared by slowly adding the dMDH stock to a stirring stock with GroEL (or HSP60) in folding buffer (50 mM Tris-HCl, pH 7.4, 50 mM KCl, 10 mM $MglC_2$, and 1 mM DTT), followed by addition of GroES (or HSP10). The binary complex stocks were prepared immediately prior to dispensing into the assay plates and had final protein concentrations of 83.3 nM GroEL (Mr 800 kDa) or HSP60 (Mr 400 kDa), 100 nM GroES or HSP10 (Mr 70 kDa), and 20 nM dMDH in folding buffer. For the ATP initiation stock, ATP solid was diluted into folding buffer to a final concentration of 2.5 mM. Quench solution contained 600 mM EDTA (pH 8.0). The MDH enzymatic assay stock consisted of 20 mM sodium mesoxalate and 2.4 mM NADH in reaction buffer (50 mM Tris-HCl, pH 7.4, 50 mM KCl, and 1 mM DTT).

Assay Protocol: First, 30 μL aliquots of the GroEL/ES-dMDH or HSP60/10-dMDH binary complex stocks were dispensed into clear, 384-well polystyrene plates. Next, 0.5 μL of the compound stocks (10 mM to 4.6 μM, 3-fold dilutions series in DMSO) were added by pin-transfer (V&P Scientific). The chaperonin-mediated refolding cycles were initiated by addition of 20 IA of ATP stock (reagent concentrations during refolding cycle: 50 nM GroEL or HSP60, 60 nM GroES or HSP10, 12 nM dMDH, 1 mM ATP, and compounds of 100 μM to 46 nM, 3-fold dilution series). The refolding reactions were incubated at 37° C. The incubation time was determined from refolding time-course control experiments until they reached ~90% completion of refolding cycle—generally ~20-40 min for GroEL/ES, and ~40-60 min for HSP60/10). Next, the assay was quenched by addition of 10 μL of the EDTA to final concentration of 100 mM. Enzymatic activity of the refolded MDH was initiated by addition of 20 μL MDH enzymatic assay stock (20 mM sodium mesoxalate and 2.4 mM NADH in reaction buffer, 50 mM Tris pH 7.4, 50 mM KCl, 1 mM DTT), and followed by measuring the NADH absorbance in each well at 340 nm using a Molecular Devices SpectraMax Plus384 microplate reader (NADH absorbs at 340 nm, while $NAD^+$ does not). $A_{340\ nm}$ measurements were recorded at 0.5 minutes (start point) and at successive time points until the amount of NADH consumed reached ~90% (end point, generally between 20-35 minutes). The differences between the start and end point $A_{340}$ values were used to calculate the % inhibition of the GroEL/ES or HSP60/10 machinery by the compounds. $IC_{50}$ values for the test compounds were obtained by plotting the % inhibition results in GraphPad Prism 6 and analyzing by non-linear regression using the log (inhibitor) vs. response (variable slope) equation. Results presented represent the averages of $IC_{50}$ values obtained from at least quadriplicate (duplicate of duplicate) replicates. For results, see Tables 1, 2, and 3.

Example 77

Counter-Screening Compounds for Inhibition of Native MDH Enzymatic Activity.

Reagent Preparations & Assay Protocol: This assay was performed as described above for the GroEL/ES-dMDH refolding assay; however, the assay protocol differed in the sequence of compound addition to the assay plates. The refolding reactions were allowed to proceed for 45 min at 37° C. in the absence of test compounds (complete refolding of MDH occurs), then quenched with the EDTA stock. Compounds were then pin-transferred into the plates after the EDTA quenching step; thus, compounds effects are only possible by inhibiting the fully-refolded MDH reporter substrate. Next enzymatic activity of the refolded MDH was initiated by addition of 20 μL MDH enzymatic assay stock (20 mM sodium mesoxalate and 2.4 mM NADH in reaction buffer, 50 mM Tris pH 7.4, 50 mM KCl, 1 mM DTT), and followed by measuring the NADH absorbance in each well at 340 nm using a Molecular Devices SpectraMax Plus384 microplate reader (NADH absorbs at 340 nm, while $NAD^+$ does not). $A_{340\ nm}$ measurements were recorded at 0.5 minutes (start point) and at successive time points until the amount of NADH consumed reached ~90% (end point, generally between 20-35 minutes). Compounds were tested in 8-point, 3-fold dilution series (62.5 μM to 29 nM during the reporter reaction) in clear, flat-bottom 384-well microtiter plates. DMSO was used as a negative control, and previously discovered native MDH inhibitors were used as positive controls. $IC_{50}$ values for the test compounds were obtained by plotting the % inhibition results in GraphPad Prism 6 and analyzing by non-linear regression using the log (inhibitor) vs. response (variable slope) equation. Results presented represent the averages of $IC_{50}$ values obtained from at least quadriplicate (duplicate of duplicate) replicates.

Example 78

Evaluation of Compounds for Inhibition of Bacterial Cell Proliferation.

Growth Media: *S. aureus* bacteria were grown in Brain Heart Infusion (BHI) broth/agar (Becton, Dickinson and Company). All liquid cultures were grown in BHI media supplemented with 25 mg/L $Ca^{2+}$ and 12.5 mg/L $Mg^{2+}$ to mimic free physiological concentrations of these cations. A 10 mg/mL $Ca^{2+}$ stock solution was prepared by dissolving 3.68 g of $CaCl_2 \cdot 2H_2O$ in 100 mL of deionized water, and a 10 mg/mL $Mg^{2+}$ stock solution was prepared by dissolving 8.36 g of $MgCl_2 \cdot 2H_2O$ in 100 mL deionized water. Both stock solutions were filter-sterilized using 0.2 μm pore size cellulose-acetate filters. 2.5 mL of the sterile 10 mg/mL $Ca^{2+}$ stock and 1.25 mL of the sterile 10 mg/mL $Mg^{2+}$ stock solutions were added per 1 L of autoclaved BHI medium to obtain 25 mg/L $Ca^{2+}$ and 12.5 mg/L $Mg^{2+}$ ions, respectively.

General Assay Protocol: Stock bacterial cultures were streaked onto BHI agar plates and grown overnight at 37° C. Fresh aliquots of broth were inoculated with single bacterial colonies and the cultures were grown overnight at 37° C. with shaking (240 rpm) in cation adjusted BHI media. The following morning, the overnight cultures were sub-cultured (1:5 dilution) into fresh aliquots of cation adjusted BHI media and grown at 37° C. for 1-2 hours with shaking. After 2 h, cultures were diluted into fresh media to achieve final $OD_{600}$ readings of 0.017. Aliquots of these diluted cultures (30 μL) were added to clear, flat-bottom, 384-well polystyrene plates that were stamped with 0.5 μL of test compounds in 20 μL media. Compounds were evaluated in dose-response format where the inhibitor concentration range during the proliferation assay was 100 μM to 46 nM (3-fold dilution series). Plates were sealed with "Breathe Easy" oxygen permeable membranes (Diversified Biotech) and left to incubate at 37° C. without shaking (stagnant assay). $OD_{600\ nm}$ readings were taken generally at 6-8 h, when bacteria had reached log-phase growth. A second set of baseline control plates were prepared analogously, but without any bacteria added, to correct for possible compound absorbance and/or precipitation. Plates were then read at 600 nm using a Molecular Devices SpectraMax Plus384 microplate reader. $EC_{50}$ values for the test compounds were obtained by plotting the $OD_{600}$ results in GraphPad Prism and analyzing by non-linear regression using the log(inhibitor) vs. response (variable slope) equation. For results, see Tables 1, 2, and 3.

Example 79

Evaluating Compound Effects on Kidney Cell Viability.

Evaluation of compound cytotoxicities to HEK 293 kidney cells was performed using an Alamar Blue-based viability assay. HEK 293 cells were maintained in MEM medium (Corning Cellgro, 10-009 CV) supplemented with 10% FBS (Sigma, F2242). All assays were carried out in 384-well plates (BRAND cell culture grade plates, 781980). Cells at 80% confluence were harvested and diluted in growth medium, then 45 μL of the HEK 293 cells (1,500 cells/well) were dispensed per well, and plates were sealed with "Breathe Easy" oxygen permeable membranes (Diversified Biotech) and incubated at 37° C., 5% $CO_2$, for 24 h. The following day, 1 μL aliquots of the compound stocks (10 mM to 4.6 μM, 3-fold dilutions in DMSO) were pre-diluted by pin-transfer into 25 μL of growth medium. Then, 15 μL aliquots of the diluted compounds were added to the cell assay plates to give inhibitor concentration ranges of 100 μM to 46 nM during the assay (final DMSO concentration of 1% was maintained during the assay). Plates were sealed with "Breathe Easy" oxygen permeable membranes and incubated for an additional 48 h at 37° C. and 5% $CO_2$. The Alamar Blue reporter reagents were then added to a final concentration of 10%, the plates incubated at 37° C. and 5% $CO_2$, and sample fluorescence (535 nm excitation, 590 nm emission) was read using a Molecular Devices FlexStation II 384-well plate reader (readings taken between 4-24 h of incubation so as to achieve signals in the 30-60% range for conversion of resazurin to resorufin). Cell viability was calculated as per vendor instructions (Thermo Fisher—Alamar Blue cell viability assay manual). Cytotoxicity $CC_{50}$ values for the test compounds were obtained by plotting the % resazurin reduction results in GraphPad Prism and analyzing by non-linear regression using the log(inhibitor) vs. response (variable slope) equation. See Tables 1, 2, and 3.

Example 80

Control Compounds, Calculation of $IC_{50}/EC_{50}/CC_{50}$ Values, and Statistical Considerations.

For all assays, DMSO was used as negative control. For the GroEL/ES and HSP60/10-mediated dMDH refolding assays, and native MDH enzymatic activity counter-screens, a panel of our previously discovered and reported chaperonin inhibitors were used as positive controls: e.g. suramin and compound 2 h-p from Abdeen et. al 2016; compounds 20R, 20L, and 28R from Abdeen et. al 2018; and closantel and rafoxanide from Kunkle et. al 2018. For the human cell viability assays, control compounds include the aforementioned compounds as well as other protein homeostasis inhibitors, such as bortezomib (proteasome inhibitor); VER-155008 (HSP70 inhibitor); and ganetespib and 17-DMAG (HSP90 inhibitors). See Table 1.

All $IC_{50}/EC_{50}/CC_{50}$ results reported are averages of values determined from individual dose-response curves in assay replicates as follows: 1) Individual $I/E/CC_{50}$ values from assay replicates were first log-transformed and the average $\log(I/E/CC_{50})$ values and standard deviations (SD) calculated; 2) Replicate $\log(I/E/CC_{50})$ values were evaluated for outliers using the ROUT method in GraphPad Prism (Q of 10%); and 3) Average $I/E/CC_{50}$ values were then back-calculated from the average $\log(I/E/CC_{50})$ values. For compounds where $\log(I/E/CC_{50})$ values were greater than the maximum compound concentrations tested (i.e. >1.8, >2.0, and >2.4—or >63, >100, and >250 μM, respectively), results were represented as 0.1 log units higher than the maximum concentrations tested (i.e., 1.9, 2.1, and 2.5—or 79, 126, and 316 μM, respectively) so as not to overly bias comparisons because of the unavailability of definitive values for these inactive compounds.

TABLE 1

Control Samples. Compilation of $IC_{50}$ / $EC_{50}$ / $CC_{50}$ results for compound 1 and purchased antibiotics tested in the GroEL/ES and HSP60/10-mediated dMDH refolding assays and the native MDH counter-screen; the *S. aureus* bacterial proliferation assay; and the HEK 293 kidney cell viability/cytotoxicity assay.

| | | Biochemical Assay $IC_{50}$ (μM) | | | | HEK 293 |
|---|---|---|---|---|---|---|
| | Compound Name | Native MDH Activity | GroEL/ ES-dMDH Refolding | HSP60/ 10-dMDH Refolding | *S. aureus* Proliferation $EC_{50}$ (μM) | Kidney Cell Viability $CC_{50}$ (μM) |
| 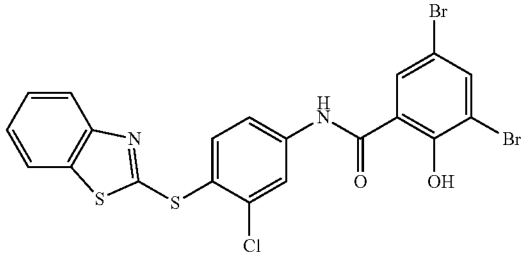 [SMILES: O=C(Nc1ccc(Sc2nc3ccccc3s2)c(Cl)c1)c1cc(Br)cc(Br)c1O] | 1 | 6.3 | 2.0 | 3.7 | 0.30 | 73 |
| 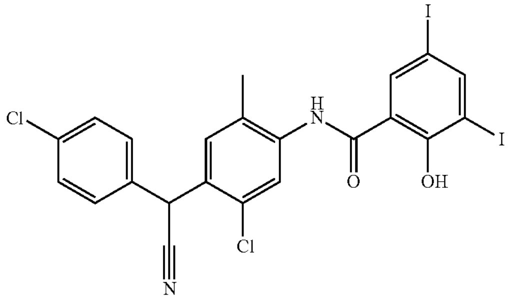 [SMILES: Cc1cc(C(C#N)c2ccc(Cl)cc2)c(Cl)cc1NC(=O)c1cc(I)cc(I)c1O] | Closantel | 6.0 | 2.2 | 3.0 | 0.48 | 79 |
| 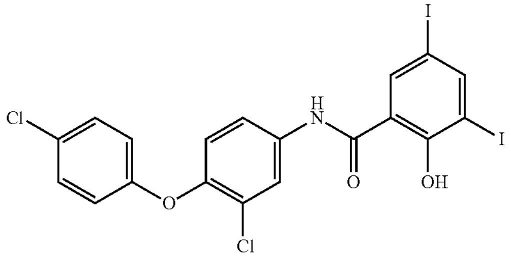 [SMILES: O=C(Nc1ccc(Oc2ccc(Cl)cc2)c(Cl)c1)c1cc(I)cc(I)c1O] | Rafoxanide | 17 | 3.8 | 2.7 | 0.30 | 82 |

TABLE 1-continued

Control Samples. Compilation of $IC_{50}$ / $EC_{50}$ / $CC_{50}$ results for compound 1 and purchased antibiotics tested in the GroEL/ES and HSP60/10-mediated dMDH refolding assays and the native MDH counter-screen; the *S. aureus* bacterial proliferation assay; and the HEK 293 kidney cell viability/cytotoxicity assay.

| | | Biochemical Assay $IC_{50}$ (μM) | | | | HEK 293 |
|---|---|---|---|---|---|---|
| | Compound Name | Native MDH Activity | GroEL/ ES-dMDH Refolding | HSP60/ 10-dMDH Refolding | *S. aureus* Proliferation $EC_{50}$ (μM) | Kidney Cell Viability $CC_{50}$ (μM) |
| 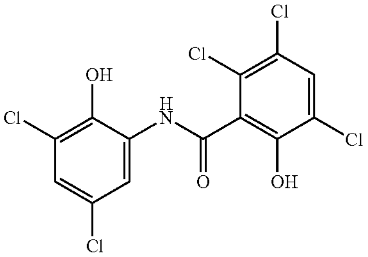 [SMILES: O=C(Nc1cc(Cl)cc(Cl)c1O)c1c(O)c(Cl)cc(Cl)c1Cl] | Oxyclosanide | 54 | 45 | 28 | 0.52 | 30 |
| 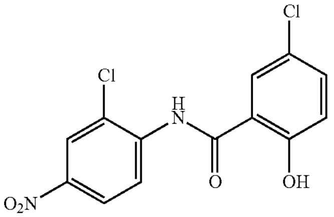 [SMILES: O=C(Nc1ccc([N+](=O)[O-])cc1Cl)c1cc(Cl)ccc1O] | Niclosamide | >63 | >100 | >100 | 0.074 | 1.7 |
| 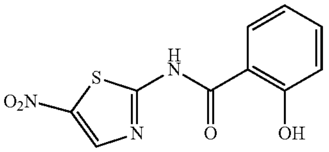 [SMILES: O=C(Nc1ncc([N+](=O)[O-])s1)c1ccccc1O] | Tizoxanide | >63 | >100 | >100 | 9.7 | 31 |
| 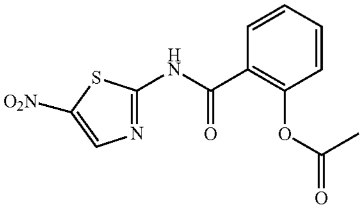 [SMILES: CC(=O)Oc1ccccc1C(=O)Nc1ncc([N+](=O)[O-])s1] | Nitazoxanide | >63 | >100 | >100 | 12 | 30 |

TABLE 2

Compounds related to formula I assay results. Compilation of $IC_{50}$ / $EC_{50}$ /$CC_{50}$ results for compounds 45-83 tested in the GroEL/ES and HSP60/10-mediated dMDH refolding assays and the native MDH counter-screen; the *S. aureus* bacterial proliferation assay, and the HEK 293 kidney cell viability/cytotoxicity assay.

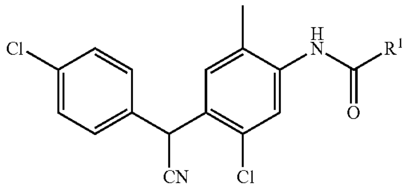

| $R^1$ | $R^2$ or Position | Compound # | Biochemical Assay IC50 (μM) Native MDH Activity | GroEL/ES-dMDH Refolding | HSP60/10-dMDH Refolding | *S. aureus* Proliferation $EC_{50}$ (μM) | HEK 293 Kidney Cell Viability $CC_{50}$ (μM) |
|---|---|---|---|---|---|---|---|
| 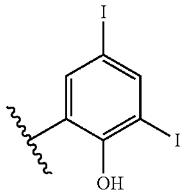 [SMILES: *c1cc(I)cc(I)c1O] | | Closantel | 6.0 | 2.2 | 3.0 | 0.48 | 79 |
| 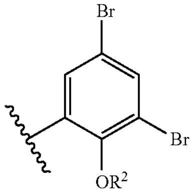 | —$CH_3$ | 45 | >63 | 30 | >100 | >100 | 66 |
| | —H | 46 | 2.3 | 1.9 | 2.4 | 0.22 | 58 |
| 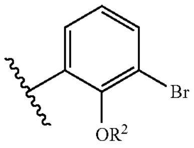 | —$CH_3$ | 47 | >63 | 49 | >100 | >100 | >100 |
| | —H | 48 | 48 | 12 | 7.7 | 0.58 | 43 |
| 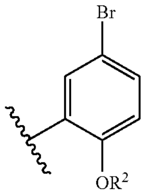 | —$CH_3$ | 49 | >63 | 71 | >100 | >100 | >100 |
| | —H | 50 | 55 | 23 | 20 | 0.11 | 3.4 |
| 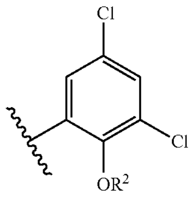 | —$CH_3$ | 51 | >63 | 38 | 86 | >100 | 83 |
| | —H | 52 | 5.5 | 3.7 | 5.2 | 0.27 | 44 |
| 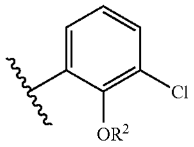 | —$CH_3$ | 53 | >63 | 81 | >100 | >100 | >100 |
| | —H | 54 | 57 | 14 | 6.4 | 0.56 | 88 |

TABLE 2-continued

Compounds related to formula I assay results. Compilation of $IC_{50}$ / $EC_{50}$ /$CC_{50}$ results for compounds 45-83 tested in the GroEL/ES and HSP60/10-mediated dMDH refolding assays and the native MDH counter-screen; the *S. aureus* bacterial proliferation assay, and the HEK 293 kidney cell viability/cytotoxicity assay.

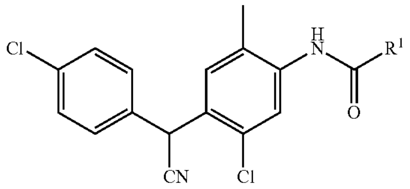

| $R^1$ | $R^2$ or Position | Compound # | Biochemical Assay IC50 (μM) Native MDH Activity | GroEL/ES-dMDH Refolding | HSP60/10-dMDH Refolding | *S. aureus* Proliferation $EC_{50}$ (μM) | HEK 293 Kidney Cell Viability $CC_{50}$ (μM) |
|---|---|---|---|---|---|---|---|
| 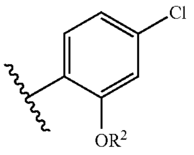 | —$CH_3$ | 55 | >63 | 59 | >100 | >100 | >100 |
| | —H | 56 | 59 | 57 | 17 | 0.13 | 16 |
| 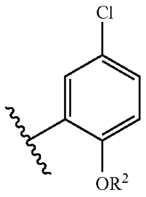 | —$CH_3$ | 57 | >63 | 59 | >100 | >100 | 28 |
| | —H | 58 | >63 | 24 | 40 | 0.14 | 11 |
| 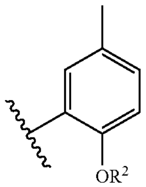 | —CH, | 59 | >63 | 86 | >100 | >100 | 32 |
| | —H | 60 | >63 | 41 | 85 | 1.3 | 49 |
| 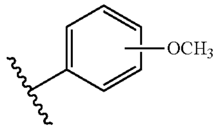 | ortho | 61 | >63 | 72 | >100 | >100 | >100 |
| | meta | 62 | >63 | 67 | >100 | >100 | 50 |
| | para | 63 | >63 | 65 | >100 | >100 | >100 |
| 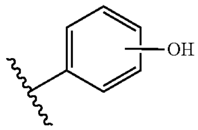 | ortho | 64 | >63 | 33 | 50 | 0.28 | 26 |
| | meta | 65 | >63 | 55 | 33 | 1.6 | 44 |
| | para | 66 | >63 | 47 | 35 | 4.9 | 65 |
| 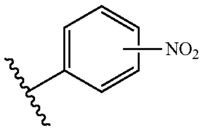 | ortho | 67 | >63 | 43 | >100 | >100 | >100 |
| | meta | 68 | >63 | 43 | >100 | >100 | >100 |
| | para | 69 | >63 | 37 | >100 | >100 | >100 |
| 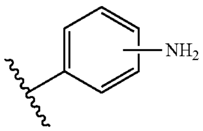 | ortho | 70 | >63 | 44 | >100 | >100 | 32 |
| | meta | 71 | >63 | 51 | >100 | >100 | 35 |
| | para | 72 | >63 | 47 | 73 | >100 | 53 |

TABLE 2-continued

Compounds related to formula I assay results. Compilation of $IC_{50}$ / $EC_{50}$ /$CC_{50}$ results for compounds 45-83 tested in the GroEL/ES and HSP60/10-mediated dMDH refolding assays and the native MDH counter-screen; the *S. aureus* bacterial proliferation assay, and the HEK 293 kidney cell viability/cytotoxicity assay.

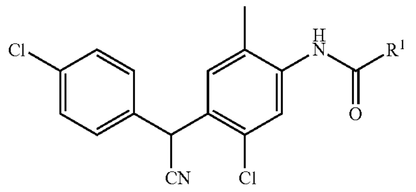

| | | | Biochemical Assay IC50 (μM) | | | | |
|---|---|---|---|---|---|---|---|
| $R^1$ | $R^2$ or Position | Compound # | Native MDH Activity | GroEL/ES-dMDH Refolding | HSP60/10-dMDH Refolding | *S. aureus* Proliferation $EC_{50}$ (μM) | HEK 293 Kidney Cell Viability $CC_{50}$ (μM) |
| 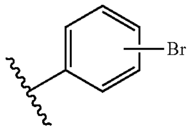 | ortho | 73 | >63 | 53 | >100 | >100 | >100 |
| | meta | 74 | >63 | 50 | >100 | >100 | >100 |
| | para | 75 | >63 | 58 | >100 | >100 | 33 |
| 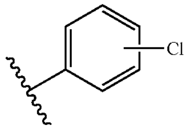 | ortho | 76 | >63 | 54 | >100 | >100 | >100 |
| | meta | 77 | >63 | 63 | >100 | >100 | >100 |
| | para | 78 | >63 | 63 | >100 | >100 | 50 |
| 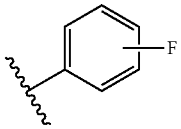 | ortho | 79 | >63 | 89 | >100 | >100 | 85 |
| | meta | 80 | >63 | 78 | >100 | >100 | 70 |
| | para | 81 | >63 | 77 | >100 | >100 | 78 |
| 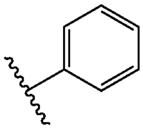 [SMILES: *c1ccccc1] | | 82 | >63 | 74 | >100 | >100 | 47 |
| 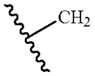 | | 83 | >63 | >100 | 69 | >100 | 83 |

TABLE 3

Compounds related to formula II assay results. Compilation of $IC_{50}$ / $EC_{50}$ /$CC_{50}$ results for compounds 57-117 tested in the GroEL/ES and HSP60/10-mediated dMDH refolding assays and the native MDH counter-screen; the *S. aureus* bacterial proliferation assay; and the HEK 293 kidney cell viability/cytotoxicity assay.

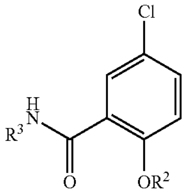

| | | | Biochemical Assay IC50 (μM) | | | | |
|---|---|---|---|---|---|---|---|
| $R^3$ Groups | R2 Groups | Compound # | Native MDH Activity | GroEL/ES-dMDH Refolding | HSP60/10-dMDH Refolding | *S. aureus* Proliferation $EC_{50}$ (μM) | HEK 293 Kidney Cell Viability $CC_{50}$ (μM) |
| 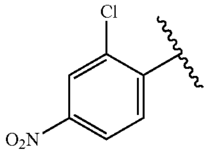 [SMILES: *c1ccc([N+](=O)[O-])cc1Cl] | | Niclosamide | >63 | >100 | >100 | 0.074 | 1.7 |
| 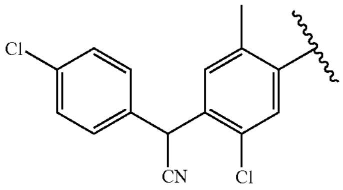 [SMILES: *c1cc(Cl)c(C(C#N)c2ccc(Cl)cc2)cc1C] | —$CH_3$ | 57 | >63 | 59 | >100 | >100 | 28 |
| | —H | 58 | >63 | 24 | 40 | 0.14 | 11 |
| 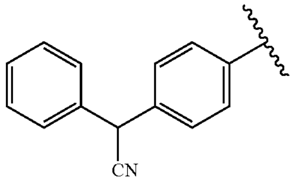 [SMILES: *c1ccc(C(C#N)c2ccccc2)cc1] | —$CH_3$ | 84 | >63 | 94 | >100 | >100 | >100 |
| | —H | 85 | >63 | 56 | 75 | 1.1 | 29 |
| 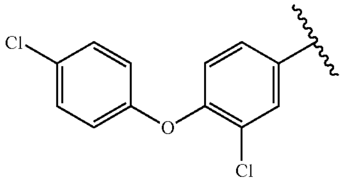 [SMILES: *c1ccc(Oc2ccc(Cl)cc2)c(Cl)c1] | —$CH_3$ | 86 | >63 | >100 | >100 | >100 | >100 |
| | —H | 87 | >63 | 30 | 9.5 | 0.17 | 10 |
| 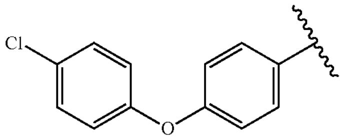 [SMILES: *c1ccc(Oc2ccc(Cl)cc2)cc1] | —$CH_3$ | 88 | >63 | >100 | >100 | >100 | >100 |
| | —H | 89 | >63 | 46 | 45 | 0.36 | 15 |
| 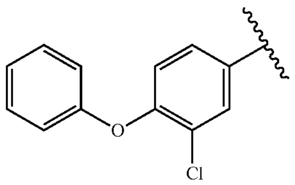 [SMILES: *c1ccc(Oc2ccccc2)c(Cl)c1] | —$CH_3$ | 90 | >63 | >100 | >100 | >100 | >100 |
| | —H | 91 | >63 | 51 | 22 | 0.21 | 4.7 |
| 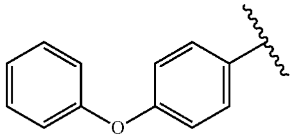 [SMILES: *c1ccc(Oc2ccccc2)cc1] | —$CH_3$ | 92 | >63 | >100 | >100 | >100 | >100 |
| | —H | 93 | >63 | 68 | >100 | 0.36 | 20 |

TABLE 3-continued

Compounds related to formula II assay results. Compilation of $IC_{50}$ / $EC_{50}$ /$CC_{50}$ results for compounds 57-117 tested in the GroEL/ES and HSP60/10-mediated dMDH refolding assays and the native MDH counter-screen; the *S. aureus* bacterial proliferation assay; and the HEK 293 kidney cell viability/cytotoxicity assay.

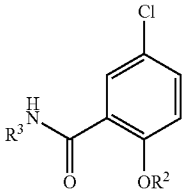

| | | | Biochemical Assay IC50 (μM) | | | | |
|---|---|---|---|---|---|---|---|
| $R^3$ Groups | R2 Groups | Compound # | Native MDH Activity | GroEL/ES-dMDH Refolding | HSP60/10-dMDH Refolding | *S. aureus* Proliferation $EC_{50}$ (μM) | HEK 293 Kidney Cell Viability $CC_{50}$ (μM) |
| 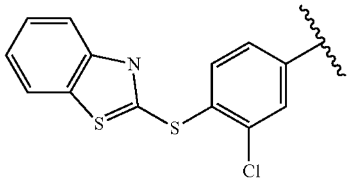 | —$CH_3$ | 94 | >63 | 61 | >100 | >100 | >100 |
| | —H | 95 | >63 | 21 | 39 | 0.14 | 83 |
| 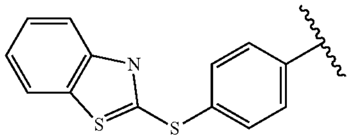 | —$CH_3$ | 96 | >63 | 59 | >100 | >100 | 56 |
| | —H | 97 | >63 | 24 | 59 | 0.10 | 26 |
| 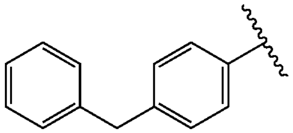 [SMILES: *c1ccc(Cc2ccccc2)cc1] | —$CH_3$ | 98 | >63 | >100 | >100 | >100 | >100 |
| | —H | 99 | >63 | 77 | >100 | >100 | 19 |
| 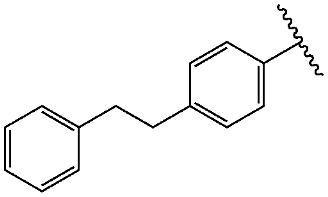 [SMILES: *c1ccc(CCc2ccccc2)cc1] | —$CH_3$ | 100 | >63 | >100 | >100 | >100 | >100 |
| | —H | 101 | >63 | 54 | 81 | 33 | 4.3 |
| 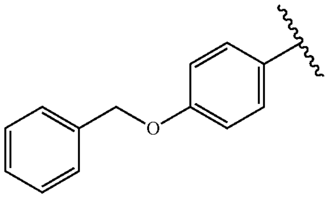 [SMILES: *c1ccc(OCc2ccccc2)cc1] | —$CH_3$ | 102 | >63 | >100 | >100 | >100 | >100 |
| | —H | 103 | >63 | 44 | >100 | >100 | >100 |
| 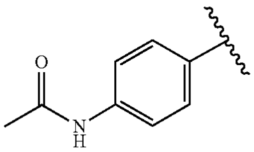 [SMILES: *c1ccc(NC(C)=O)cc1] | —$CH_3$ | 104 | >63 | >100 | >100 | >100 | >100 |
| | —H | 105 | >63 | >100 | >100 | >100 | 69 |
| 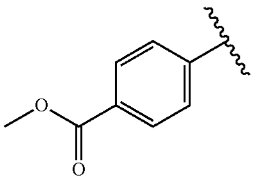 [SMILES: *c1ccc(C(=O)OC)cc1] | —$CH_3$ | 106 | >63 | 46 | >100 | >100 | 24 |
| | —H | 107 | >63 | 83 | >100 | 0.94 | 11 |

TABLE 3-continued

Compounds related to formula II assay results. Compilation of $IC_{50}$ / $EC_{50}$ /$CC_{50}$ results for compounds 57-117 tested in the GroEL/ES and HSP60/10-mediated dMDH refolding assays and the native MDH counter-screen; the *S. aureus* bacterial proliferation assay; and the HEK 293 kidney cell viability/cytotoxicity assay.

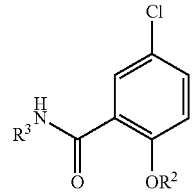

| $R^3$ Groups | R2 Groups | Compound # | Biochemical Assay IC50 (μM) Native MDH Activity | GroEL/ES-dMDH Refolding | HSP60/10-dMDH Refolding | *S. aureus* Proliferation $EC_{50}$ (μM) | HEK 293 Kidney Cell Viability $CC_{50}$ (μM) |
|---|---|---|---|---|---|---|---|
| 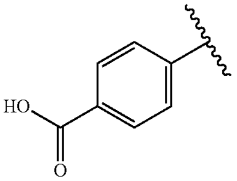 [SMILES: *c1ccc(C(=O)O)cc1] | —$CH_3$ | 108 | >63 | >100 | >100 | >100 | >100 |
| | —H | 109 | | >100 | >100 | >100 | >100 |
| 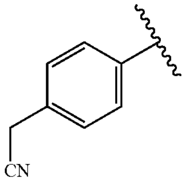 [SMILES: *c1ccc(CC#N)cc1] | —$CH_3$ | 110 | >63 | 54 | >100 | >100 | >100 |
| | —H | 111 | >63 | >100 | >100 | >100 | 19 |
| 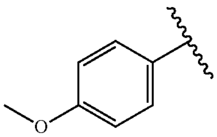 [SMILES: *c1ccc(OC)cc1] | —$CH_3$ | 112 | >63 | >100 | >100 | >100 | >100 |
| | —H | 113 | >63 | >100 | >100 | 31 | 19 |
| 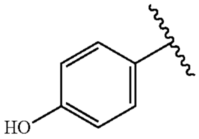 [SMILES: *c1ccc(O)cc1] | —$CH_3$ | 114 | >63 | >100 | >100 | >100 | >100 |
| | —H | 115 | >63 | >100 | >100 | >100 | >100 |
| 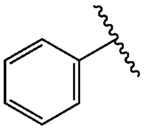 [SMILES: *c1ccccc1] | —$CH_3$ | 116 | >63 | >100 | >100 | >100 | >100 |
| | —H | 117 | >63 | >100 | >100 | 2.2 | 13 |

What is claimed is:

1. A compound of formula Ia (Ia)

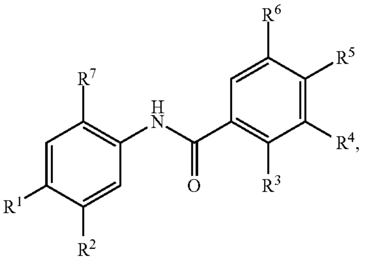

wherein $R^1$ is —OH, —$OC_1$—$C_6$ alkyl, —NHC(O)$C_1$-$C_6$ alkyl, —C(O)$OC_1$—$C_6$ alkyl, —C(O)OH, $C_1$-$C_6$ alkyl, or

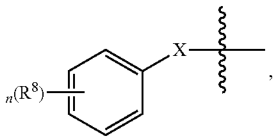, wherein each hydrogen atom in $C_1$-$C_6$ alkyl is optionally substituted by —CN, $R^2$ is H or halo, each of $R^3$, $R^4$, $R^5$, and $R^6$ is independently H, —OH, halo, $C_1$-$C_6$ alkyl, —O—$C_1$-$C_6$ alkyl, —$NO_2$, or —$NH_2$, $R^7$ is H or $C_1$-$C_6$ alkyl, X is —O—, —S—, —$C(R^9)(R^{10})_m$—, or —$C(R^9)(R^{10})_m$O;

$R^8$ is halo, $R^9$ is H or —CN, $R^{10}$ is H or —CN, m is 1 or 2, and n is 0, 1, or 2;

or a pharmaceutically acceptable salt thereof, provided the compound is not

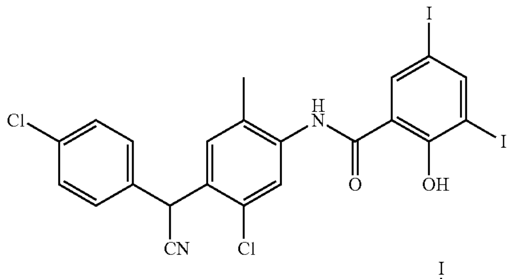

or

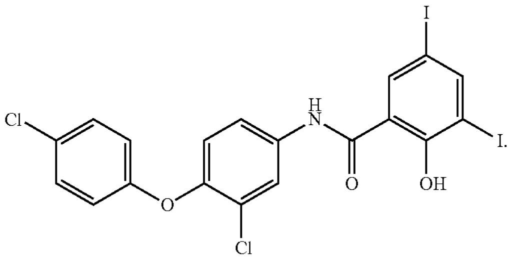

2. The compound or pharmaceutically acceptable salt of claim 1, wherein $R^3$ is —OH or —O—$C_1$-$C_6$ alkyl; and each of $R^4$, $R^5$, and $R^6$ is independently H or halo.

3. A compound of formula Ia (Ia)

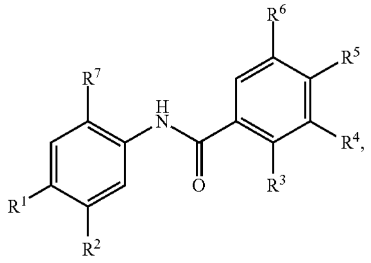

wherein $R^1$ is

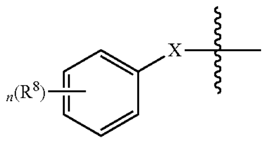

;

$R^2$ is halo, $R^3$ is —OH or —O—$C_1$-$C_6$ alkyl;

$R^4$ is halo;

$R^5$ is H, —OH, halo, $C_1$-$C_6$ alkyl, —O—$C_1$-$C_6$ alkyl, —$NO_2$, or —$NH_2$;

$R^6$ is halo;

$R^7$ is $C_1$-$C_6$ alkyl;

$R^8$ is chloro;

X is —C(H)(CN)—; and n is 0, 1, or 2;

or a pharmaceutically acceptable salt thereof, provided the compound is not

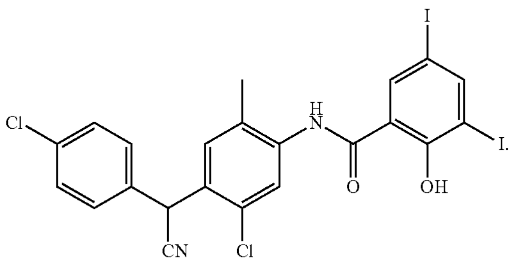 [SMILES: Cc1cc(C(C#N)c2ccc(Cl)cc2)c(Cl)cc1NC(=O)c1cc(I)cc(I)c1O]

4. The compound or pharmaceutically acceptable salt of claim 3, wherein $R^2$ is chloro.

5. A method of killing or inhibiting the growth of bacteria, said method comprising contacting the bacteria with a compound of the formula Ia (Ia)

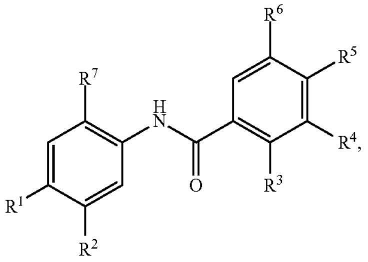

wherein $R^1$ is —OH, —$OC_1$—$C_6$ alkyl, —NHC(O)$C_1$-$C_6$ alkyl, —C(O)$OC_1$—$C_6$ alkyl, —C(O)OH, $C_1$-$C_6$ alkyl, or

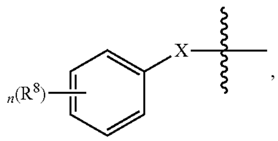

, wherein each hydrogen atom in $C_1$-$C_6$ alkyl is optionally substituted by —CN, $R^2$ is H or halo, each of $R^3$, $R^4$, $R^5$, and $R^6$ is independently H, —OH, halo, —O—$C_1$-$C_6$ alkyl, —$NO_2$, or —$NH_2$, $R^7$ is H or $C_1$-$C_6$ alkyl, X is —O—, —S—, —$C(R^9)(R^{10})_m$—, or —$C(R^9)(R^{10})_m$O—, $R^8$ is halo, $R^9$ is H or —CN, $R^{10}$ is H or —CN, m is 1 or 2, and n is 0, 1, or 2;

or a pharmaceutically acceptable salt thereof, provided the compound is not

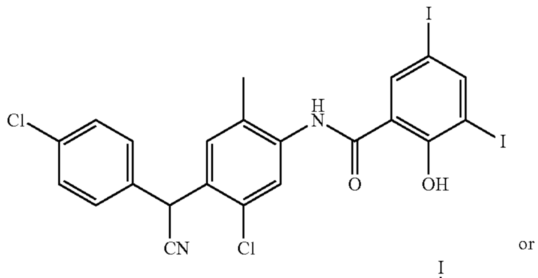

or

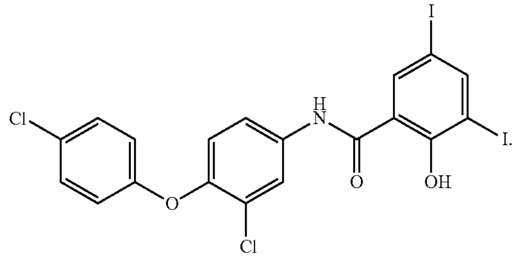

6. The method of claim 5, wherein $R^3$ is —OH or —O—$C_1$-$C_6$ alkyl; and each of $R^4$, $R^5$, and $R^6$ is independently H or halo.

7. The method of claim 6, wherein $R^6$ is chloro.

8. The method of claim 6, wherein $R^2$ is chloro.

9. The method of claim 5, wherein the genus of bacteria are selected from a group consisting of *Enterococcus, Staphylococcus, Klebsiella, Acinetobacter, Pseudomonas*, and *Enterobacter* or a combination thereof.

10. The method of claim 9, wherein the bacteria are *Enterococcus faecium, Staphylococcus aureus*, methicillin-resistant *Staphylococcus aureus* (MRSA), *Klebsiella pneumoniae, Acinetobacter baumannii, Pseudomonas aeruginosa, Enterobacter cloacae*, or a combination thereof.

11. A pharmaceutical composition comprising a therapeutically effective amount of a compound according to claim 1.

12. A method of killing bacteria in a biofilm comprising contacting the biofilm with a compound of claim 1.

13. A method of preventing bacteria from forming a biofilm comprising contacting the bacteria with a compound of claim 1.

14. The method of claim 12, wherein the bacteria is from the genus *Staphylococcus*.

15. The method of claim 5, wherein $R^1$ is

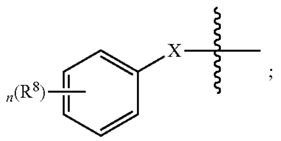

and X is —O—, —S—, —$CH_2$—, —$CH_2CH_2$—, —$CH_2O$—, or —C(H)(CN).

16. The method of claim 15, wherein X is —O— or —C(H)(CN).

17. The compound or pharmaceutically acceptable salt of claim 1, wherein $R^1$ is

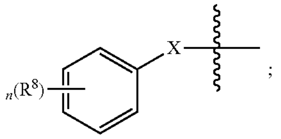

and X is —O—, —S—, —$CH_2$—, —$CH_2CH_2$—, —$CH_2O$—, or —C(H)(CN).

18. The compound or pharmaceutically acceptable salt of claim 17, wherein X is —O— or —C(H)(CN).

19. The compound of claim 1, wherein the compound is selected from the group consisting of

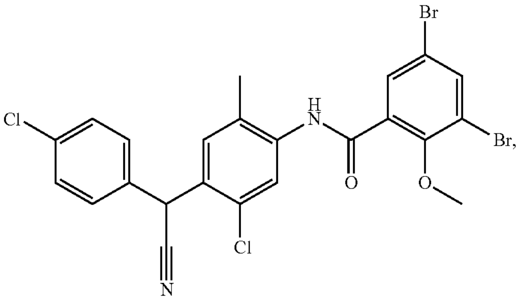

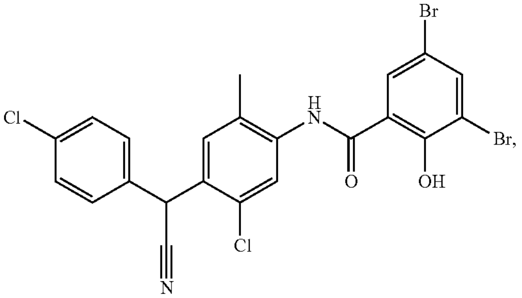

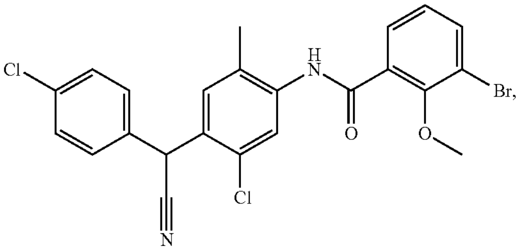

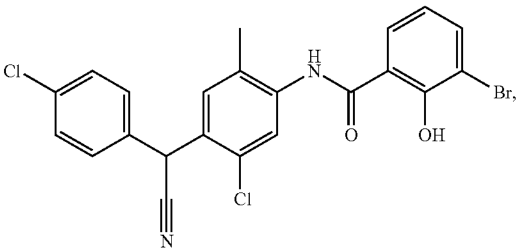

-continued
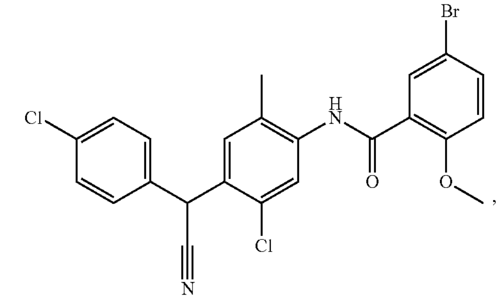
,
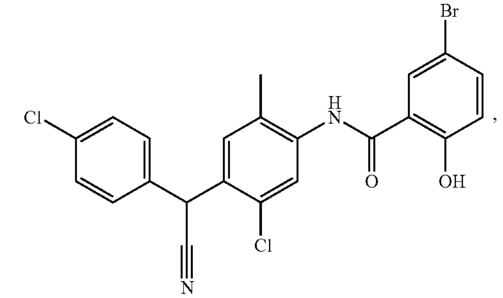
,
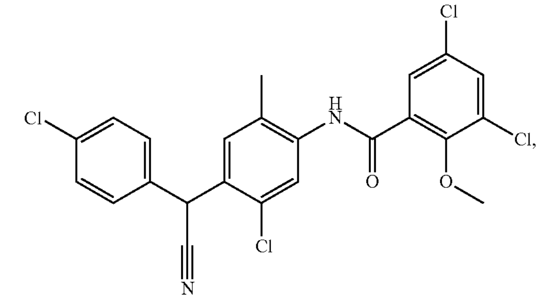
,
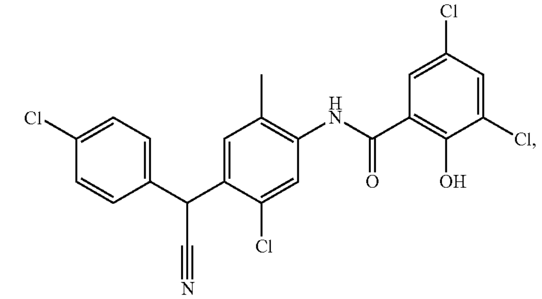
,
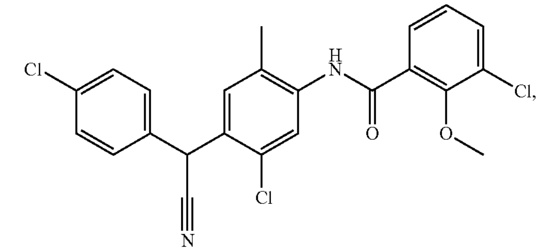
,
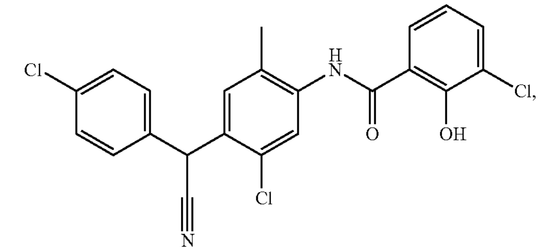
,
-continued
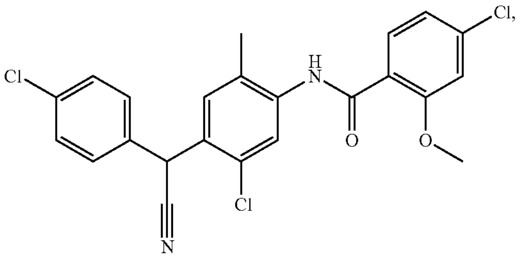
,
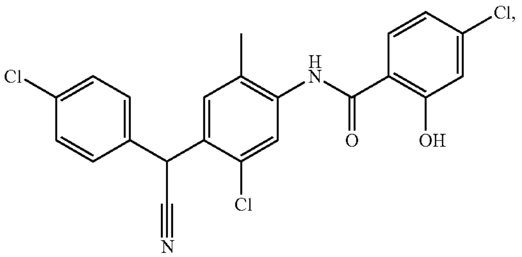
,
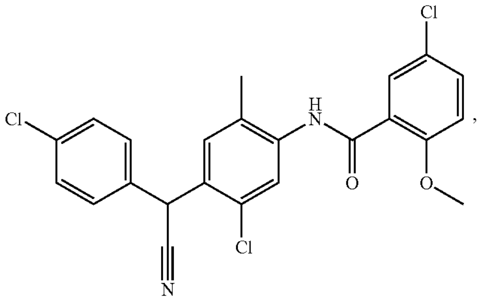
,
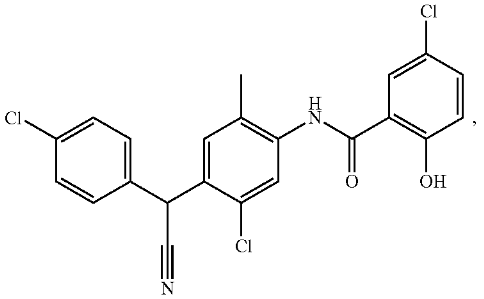
,
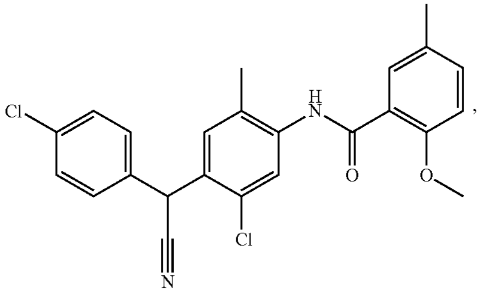
,
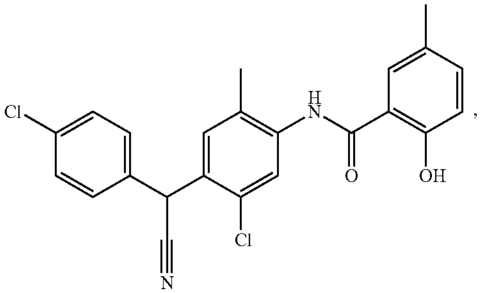
, -continued
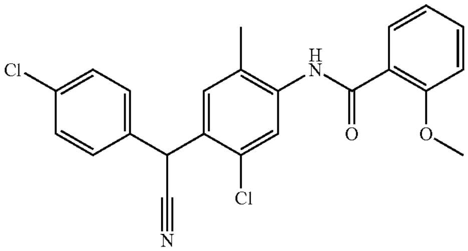
,
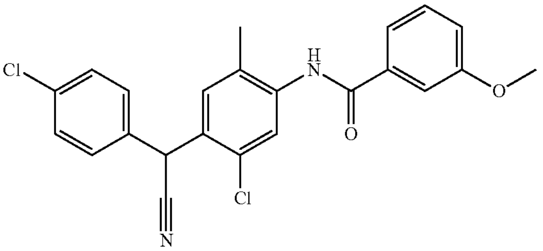
,
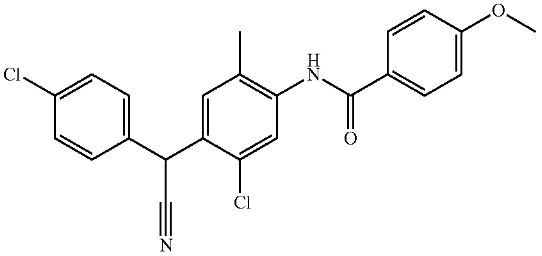
,
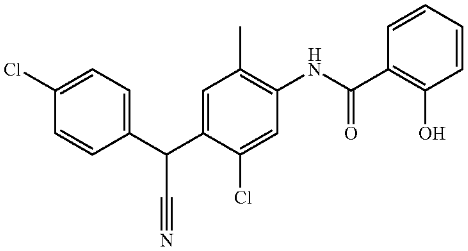
,
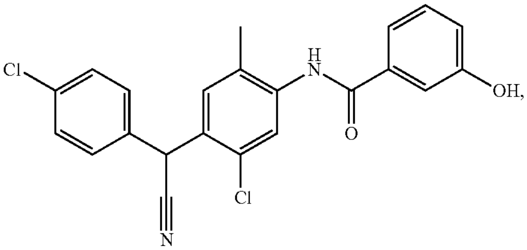
,
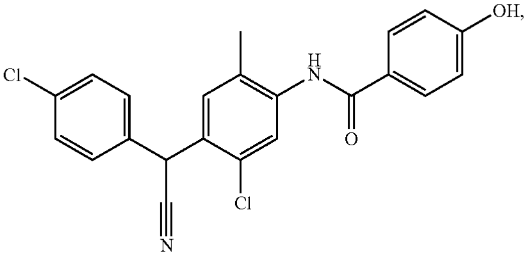
,
-continued
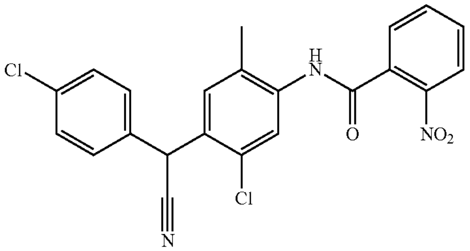
,
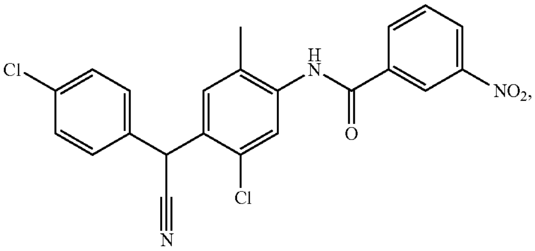
,
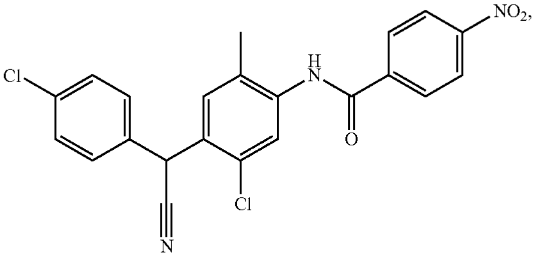
,
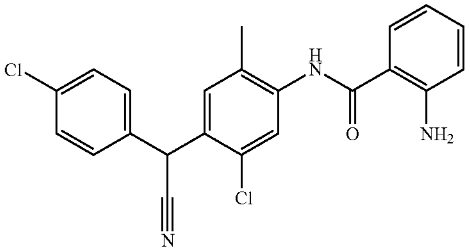
,
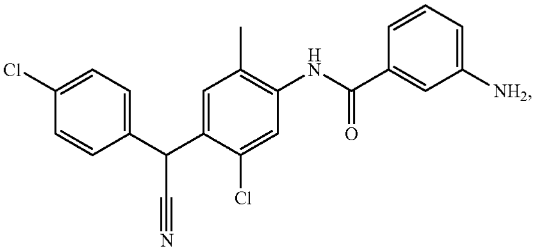
,
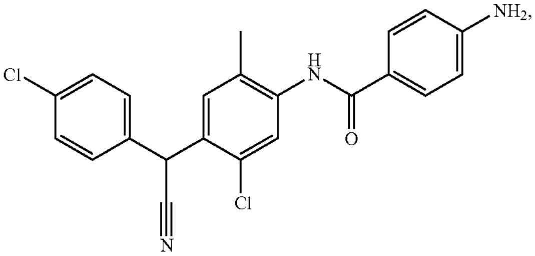
, -continued
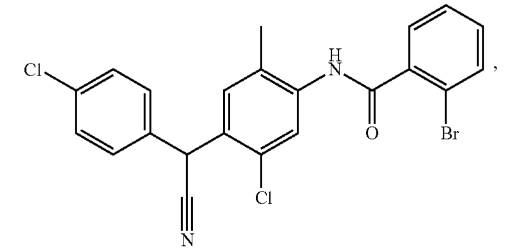
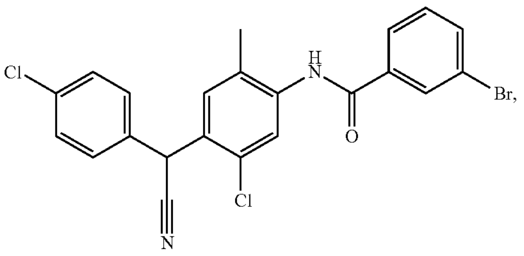
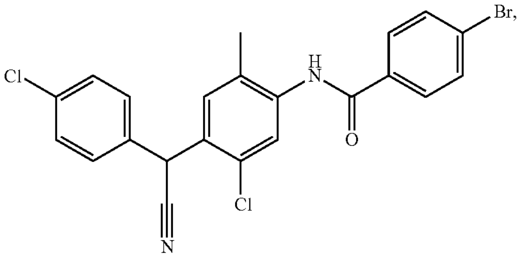
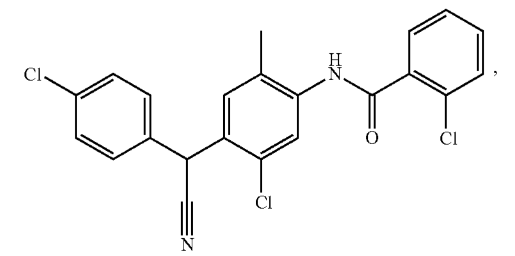
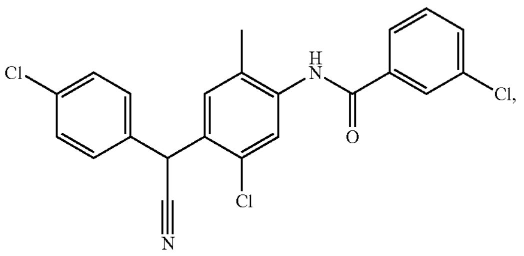
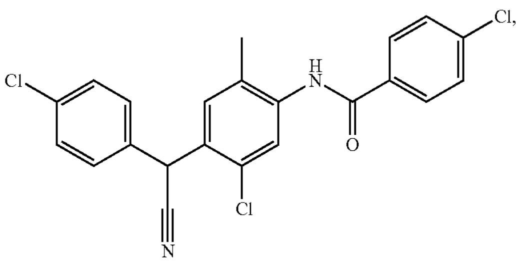
-continued
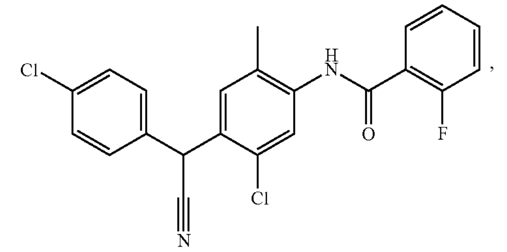
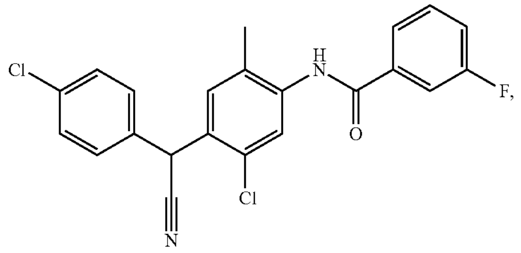
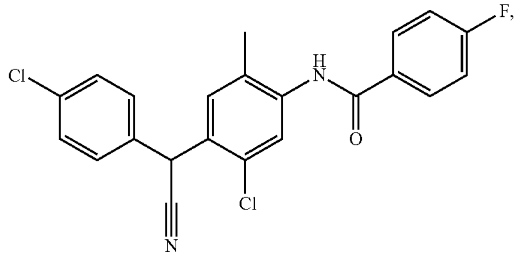
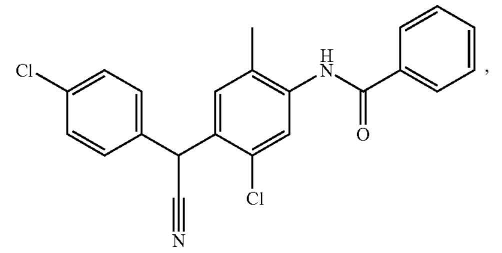
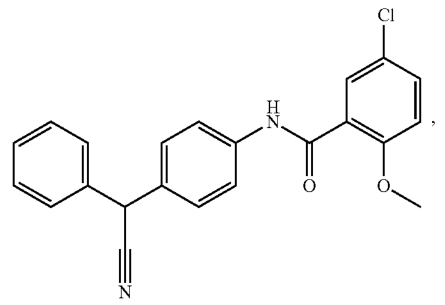
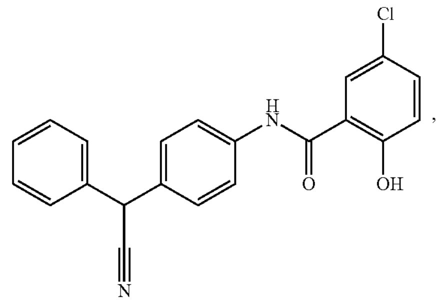

-continued
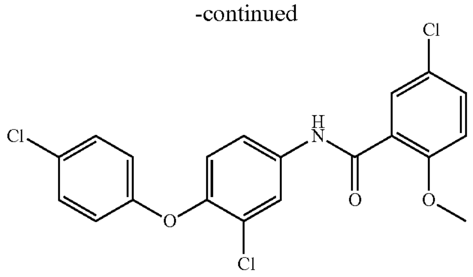,
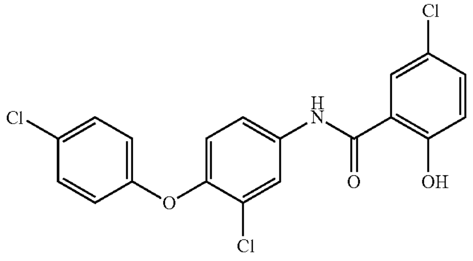,
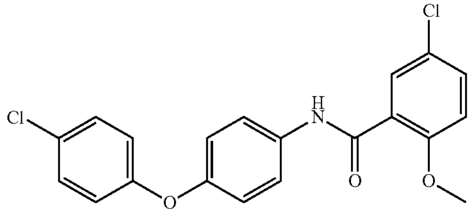,
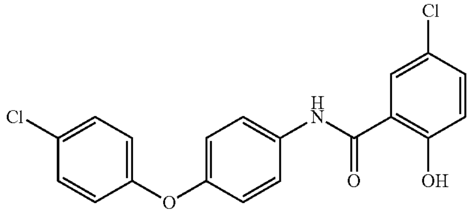,
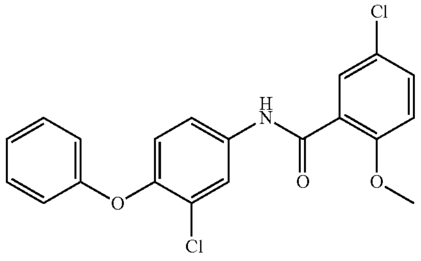,
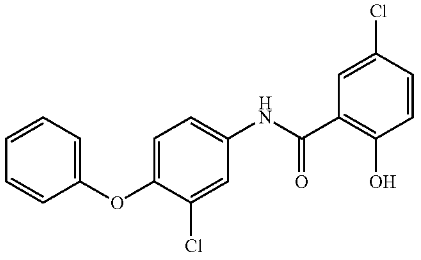,
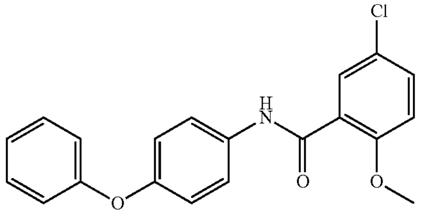,
-continued
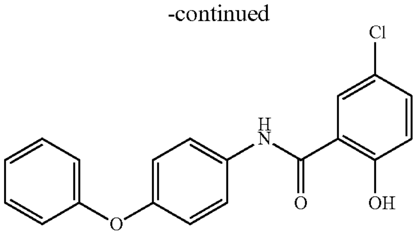,
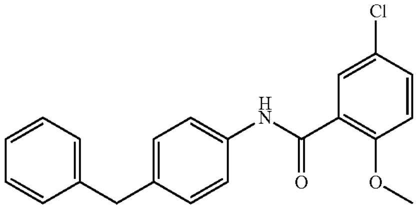,
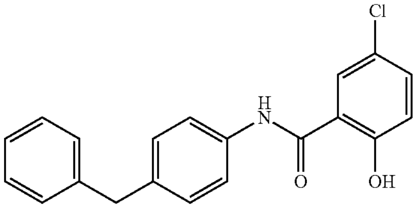,
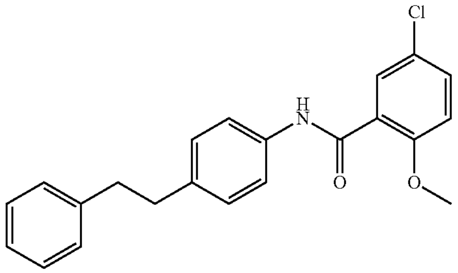,
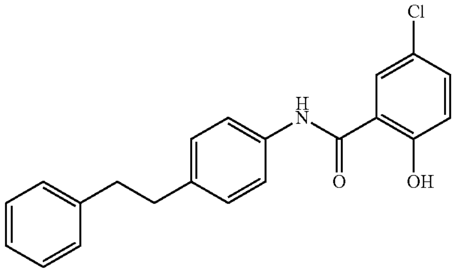,
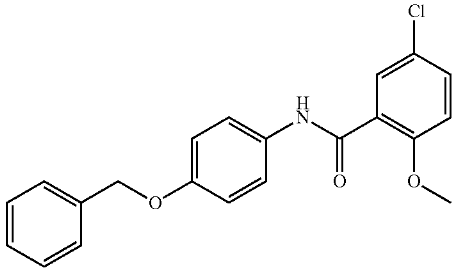,
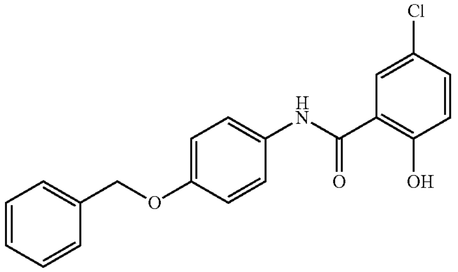, -continued
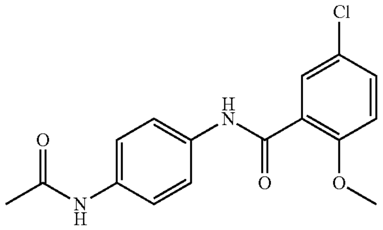,
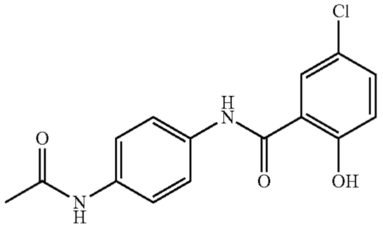,
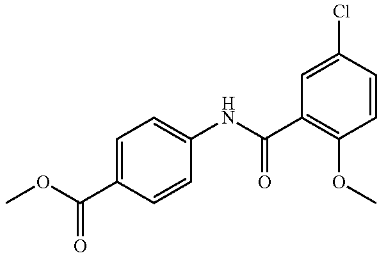,
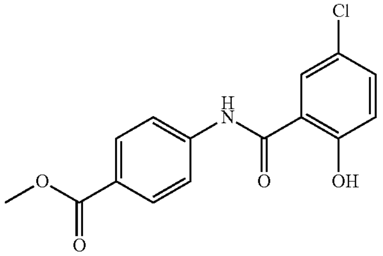,
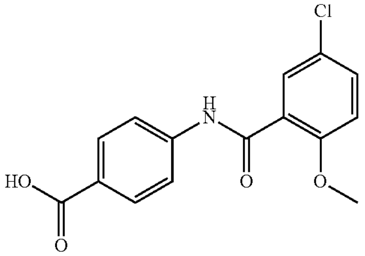,
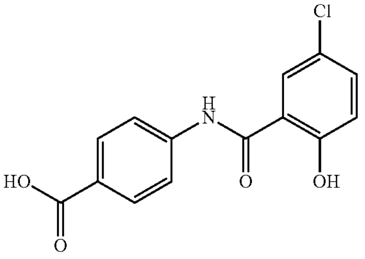,
-continued
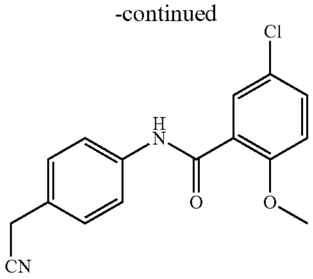,
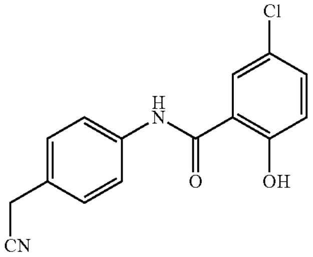,
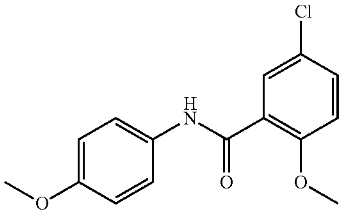,
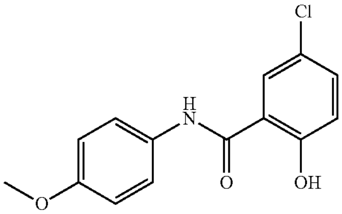,
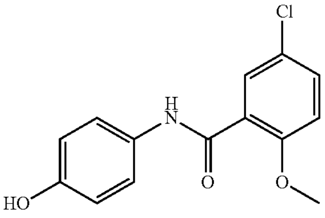, and
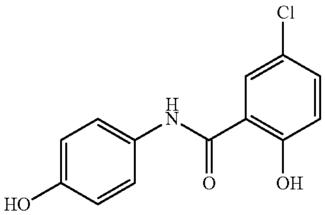;
or a pharmaceutically acceptable salt thereof.
20. The compound of claim 3, wherein the compound is selected from the group consisting of -continued
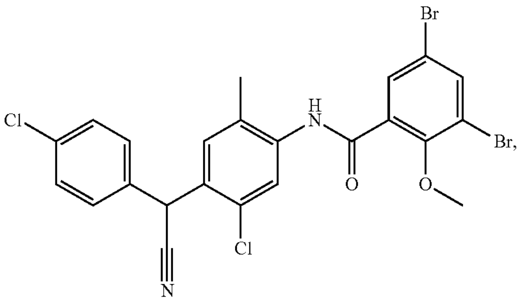
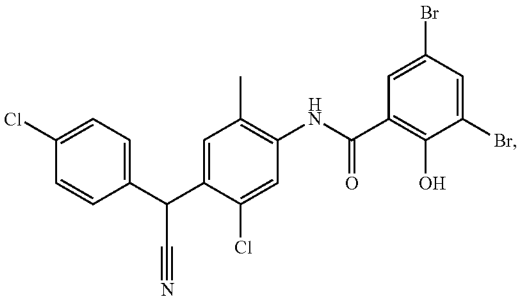
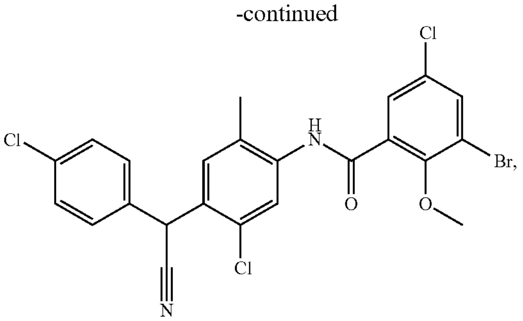
Br, and
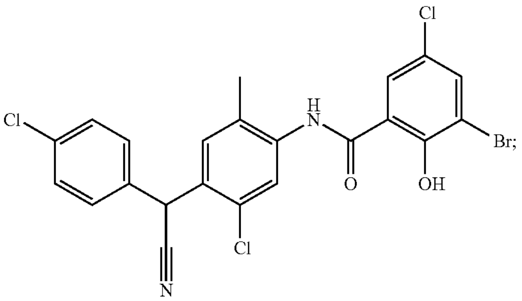
or a pharmaceutically acceptable salt thereof.
* * * * *